(12) United States Patent
Siegwart et al.

(10) Patent No.: US 9,801,944 B2
(45) Date of Patent: *Oct. 31, 2017

(54) LIPOCATIONIC POLYMERS AND USES THEREOF

(71) Applicant: The Board of Regents of the University of Texas System, Austin, TX (US)

(72) Inventors: Daniel J. Siegwart, Dallas, TX (US); Jing Hao, Newburg, OR (US); Kejin Zhou, Dallas, TX (US); Jason Miller, Dallas, TX (US); Petra Kos, Dallas, TX (US); Lian Xue, Dallas, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/261,245

(22) Filed: Sep. 9, 2016

(65) Prior Publication Data
US 2017/0100482 A1 Apr. 13, 2017

Related U.S. Application Data

(63) Continuation of application No. 14/962,422, filed on Dec. 8, 2015, now Pat. No. 9,517,270.

(60) Provisional application No. 62/089,066, filed on Dec. 8, 2014.

(51) Int. Cl.
| | |
|---|---|
| *A61K 47/34* | (2017.01) |
| *C07H 21/02* | (2006.01) |
| *C07H 21/04* | (2006.01) |
| *A61K 47/28* | (2006.01) |
| *A61K 47/22* | (2006.01) |
| *C08G 65/48* | (2006.01) |
| *C08G 63/91* | (2006.01) |
| *A61K 31/713* | (2006.01) |
| *A61K 9/00* | (2006.01) |
| *A61K 47/24* | (2006.01) |
| *C08G 63/688* | (2006.01) |
| *C12N 15/113* | (2010.01) |
| *A61K 9/51* | (2006.01) |

(52) U.S. Cl.
CPC ............ *A61K 47/34* (2013.01); *A61K 9/0019* (2013.01); *A61K 9/5153* (2013.01); *A61K 31/713* (2013.01); *A61K 47/24* (2013.01); *A61K 47/28* (2013.01); *C08G 63/688* (2013.01); *C12N 15/113* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 6,998,115 B2 | 2/2006 | Langer et al. | |
| 7,427,394 B2 | 9/2008 | Anderson et al. | |
| 8,071,082 B2 | 12/2011 | Zugates et al. | |
| 8,163,861 B2 | 4/2012 | Puerta et al. | |
| RE43,612 E | 8/2012 | Anderson et al. | |
| 8,287,849 B2 | 10/2012 | Langer et al. | |
| 8,362,175 B2 | 1/2013 | Puerta et al. | |
| 8,557,231 B2 | 10/2013 | Langer et al. | |
| 8,562,966 B2 | 10/2013 | Zugates et al. | |
| 8,748,551 B2 | 6/2014 | Puerta et al. | |
| 9,101,666 B2 | 8/2015 | Langer et al. | |
| 9,175,114 B2 | 11/2015 | Puerta et al. | |
| 9,517,270 B2* | 12/2016 | Siegwart | A61K 31/713 |
| 2008/0311040 A1 | 12/2008 | Berry et al. | |
| 2009/0012033 A1 | 1/2009 | Demattei et al. | |
| 2011/0129921 A1 | 6/2011 | Johnson et al. | |
| 2013/0253038 A1 | 9/2013 | Koizumi et al. | |
| 2014/0235872 A1 | 8/2014 | Budzik et al. | |

FOREIGN PATENT DOCUMENTS

| | | |
|---|---|---|
| WO | WO 2008/134276 | 11/2008 |
| WO | WO 2012/156058 | 11/2012 |
| WO | WO 2014/066811 | 5/2014 |

OTHER PUBLICATIONS

Akinc et al., "A combinatorial library of lipid-like materials for delivery of RNAi therapeutics," *Nat Biotechnol*, 26(5):561-569, 2008.
Albertsson and Varma, "Aliphatic polyesters: synthesis, properties and applications," *Adv Polym Sci*, 157:1-40, 2002.
Coelho et al., "Safety and efficacy of RNAi therapy for transthyretin amyloidosis," *New Engl J Med*, 369(9)819-829, 2013.
Dahlman et al., "In vivo endothelial siRNA delivery using polymeric nanoparticles with low molecular weight, " *Nat Nanotechnol*, 9(8):648-655, 2014.
Davis et al., "Evidence of RNAi in humans from systemically administered siRNA via targeted nanoparticles, " *Nature* (London, U. K.), 464(7291):1067-1070, 2010.
Green et al., "A combinatorial polymer library approach yields insight into nonviral gene delivery," *Acc Chem Res.*, 41(6):749-759, 2008.
Hao et al., "Rapid synthesis of a lipocationic polyester library via ring-opening polymerization of functional valerolactones for efficacious siRNA delivery," *J. Am. Chem. Soc.*, 137:9206-9209, 2015.
Hao et al., "Synthesis of Functionalized Poly(caprolactone)s and Their Application as Micellar Drug Delivery Systems," *Current Organic Chemistry*, 17:930-942, 2013.
Jayaraman et al., "Maximizing the potency of siRNA lipid nanoparticles for hepatic gene silencing in vivo," *Angew Chem Int Ed Engl.*, 51:8529-8533, 2012.
Jérôme and Lecomte, "Recent advances in the synthesis of aliphatic polyesters by ring-opening polymerization," *Advanced Drug Delivery Reviews*, 60:1056-1076, 2008.

(Continued)

*Primary Examiner* — Richard Schnizer
(74) *Attorney, Agent, or Firm* — Parker Highlander PLLC

(57) ABSTRACT

Polymers produced by ring opening polymerization which comprises an amino group that can be used in compositions to deliver a nucleic acid such as a miRNA or a siRNA. In some embodiments, compositions which comprise the polymers described herein and a nucleic acid are also provided herein. In some embodiments, these compositions are used to silence one or more genes in vivo or treat a disease or disorder.

20 Claims, 23 Drawing Sheets
(15 of 23 Drawing Sheet(s) Filed in Color)

(56) References Cited

OTHER PUBLICATIONS

Kanasty et al., "Delivery materials for siRNA therapeutics," *Nat Mater*, 12(11):967-977, 2013.
Kim et al., "Facile Synthesis of Functionalized Lactones and Organocatalytic Ring-Opening Polymerization," *ACS Macro Letters*, 1:845-847, 2012.
Kuiper et al., "Vitamin C supplementation lowers urinary levels of 4-hydroperoxy-2-nonenal metabolites in humans," *Free Radical Biology & Medicine*, 50:848-853, 2011.
Lee et al., "Self-assembled siRNA-PLGA conjugate micelles for gene silencing,"*Journal of Controlled Release*, 152:152-158, 2011.
Love et al., "Lipid-like materials for low-dose, in vivo gene silencing," *PNAS*, 107:1864-1869, 2010.
Lynn and Langer, "Degradable Poly(β-amino esters): Synthesis, Characterization, and Self-Assembly with Plasmid DNA," *Journal of the American Chemical Society*, 122:10761-10768, 2000.
Nelson et al., "Balancing cationic and hydrophobic content of PEGylated siRNA polyplexes enhances endosome escape, stability, blood circulation time, and bioactivity in vivo," *ACS Nano*, 7:8870-8880, 2013.
Parmar et al., "Novel endosomolytic poly(amido amine) polymer conjugates for systemic delivery of siRNA to hepatocytes in rodents and nonhuman primates,"*Bioconjugate Chem*, 25:896-906, 2014.
PCT International Search Report and Written Opinion issued in International Application No. PCT/US2015/064380, dated Feb. 19, 2016.
Philipp et al., "Hydrophobically modified oligoethylenimines as highly efficient transfection agents for siRNA delivery," *Bioconjugate Chem*, 20:2055-2061, 2009.
Pounder and Dove, "Towards poly(ester) nanoparticles: recent advances in the synthesis of functional poly(ester)s by ring-opening polymerization," *Polym Chem*, 1:260-271, 2010.
Scholz and Wagner, "Therapeutic plasmid DNA versus siRNA delivery: Common and different tasks for synthetic carriers," *Journal of Controlled Release*, 161:554-565, 2012.
Schroeder et al., "Alkane-modified short polyethyleneimine for siRNA delivery," *Journal of Controlled Release*, 160(2):172-176, 2012.
Semple et al., "Rational design of cationic lipids for siRNA delivery," *Nat Biotechnol*, 28(2)172-176, 2010.
Siegwart et al., "Combinatorial synthesis of chemically diverse core-shell nanoparticles for intracellular delivery," *PNAS*, 108:12996-13001, 2011.
Tan et al., "Engineering Nanocarriers for siRNA Delivery," *Small*, 7:841, 2011.
Tian et al., "Biodegradable synthetic polymers: preparation, functionalization and biomedical application," *Prog Polym Sci*, 37:237-280, 2012.
Whitehead et al., "Knocking down barriers: advances in siRNA delivery," *Nat Rev Drug Discov.*, 8(2):129-138, 2009.
Zimmermann et al., "RNAi-mediated gene silencing in non-human primates," *Nature*, 441(7089):111-114, 2006.
Zugates et al., "Synthesis of poly(beta-amino ester)s with thiol-reactive side chains for DNA delivery," *Journal of the American Chemical Society*, 128(39):12726-12734, 2006.

\* cited by examiner

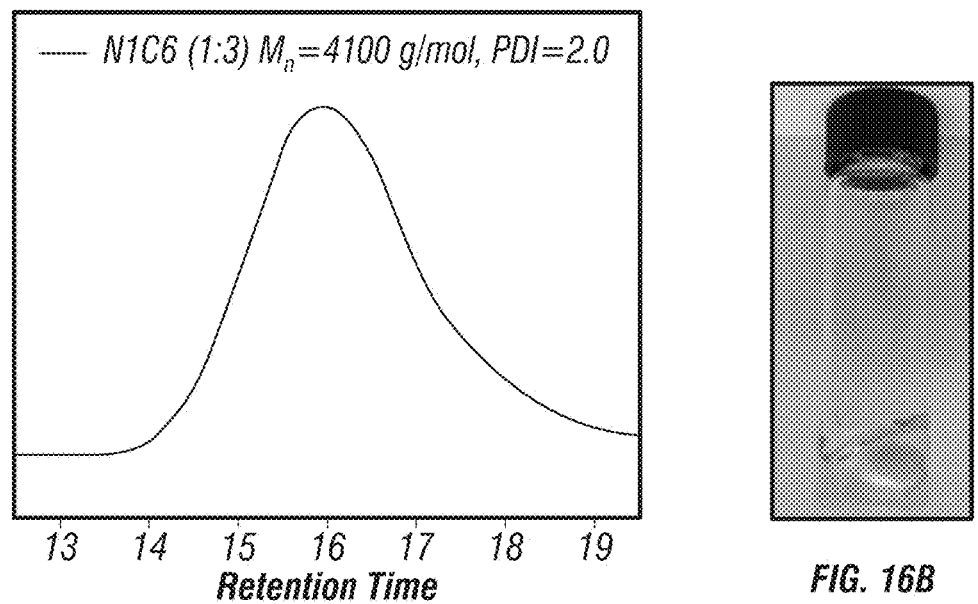
FIG. 16A
FIG. 16B
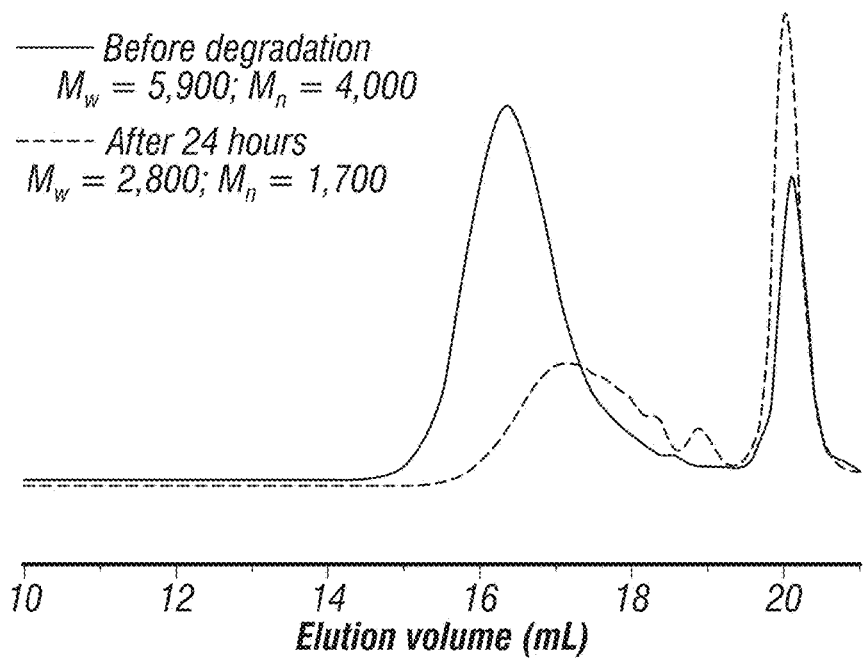
FIG. 17

SEQUENCE LISTING

<160> NUMBER OF SEQ ID NOS: 2

<210> SEQ ID NO 1
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 1
gauuaugucc gguuaugua          19

<210> SEQ ID NO 2
<211> LENGTH: 19
<212> TYPE: RNA

```
<213> ORGANISM: Artificial sequence
<220> FEATURE:
<223> OTHER INFORMATION: Synthetic oligonucleotide

<400> SEQUENCE: 2
uacauaaccg gacauaauc                                              19
```

LIPOCATIONIC POLYMERS AND USES THEREOF

This application is a continuation of U.S. application Ser. No. 14/962,422, filed Dec. 8, 2015, which claims benefit of priority to U.S. Provisional Application Ser. No. 62/089,066, filed Dec. 8, 2014, the entire contents of each of which are hereby incorporated by reference.

BACKGROUND

1. Field

The present disclosure relates generally to the fields of polymers and nanoparticles. In particular, it relates to a polymer composition which comprises a nucleic acid. More particularly, it relates to polymers produced through ring opening polymerization for the delivery of the nucleic acid.

2. Description of Related Art

Gene silencing via the RNA Interference (RNAi) mechanism is a promising strategy to treat major diseases including cancer, genetic disorders, and viral infections. However, the success of siRNA-based therapies has been limited by the difficulty of delivering these highly anionic biomacromolecular drugs into cells (Whitehead et al., 2009). Polymers are an important class of materials for drug and nucleic acid delivery due to the versatility in constructing different nanostructures including micelles, polyplexes, dendrimers, and polymer-siRNA conjugates (Lee et al., 2011 and Parmar et al., 2014). The ability to control chemical functionality is an exciting feature of modern polymer science that enables precise design of drug delivery systems. Compared to lipid-based systems, the chemical and physical properties can be more extensively and precisely engineered (Tan et al., 2011). Aliphatic polyesters synthesized by ring-opening polymerization including polyglycolide, polylactide, polycaprolactone, and their copolymers have been approved by the FDA in a number of products (Albertsson and Varma, 2002). But since they lack the required functional groups for siRNA binding and release, new synthetic strategies are required to prepare functionalized polyesters. To date, functionalized lactones have generally been accessed via low-yielding, multi-step synthetic pathways that often involve protecting groups, thereby limiting the scale of monomer and polymer production. As a direct consequence, it is challenging to sufficiently modulate polymer functionality to achieve effective delivery. Thus, the present disclosure employs a strategy to prepare functional lactone monomers in one step from commercially available starting materials. Furthermore, the polymerization is scalable and rapid with high monomer conversion that enabled the synthesis and screening of a variety of copolymer compositions and led to the discovery of optimal delivery materials.

Ring-opening polymerization of functional monomers has emerged as the most versatile method to prepare clinically translatable degradable polyesters (Jerome and Lecomte, 2008, Pounder and Dove, 2010 and Tian et al., 2012). A variety of functional groups have been introduced into lactones; however, the direct polymerization of tertiary amine functionalized cyclic esters has remained elusive. Numerous studies of lipids and non-degradable polymers have implicated tertiary amines and alkyl chains as key functional groups for effective siRNA delivery (Akincw et al., 2008, Love et al., 2010, Siegwart et al., 2011, Jayaraman et al., 2012., Scholz and Wagner, 2012 and Nelson et al., 2013). Yet, their potential incapability with esters has made direct synthesis of degradable polymers with amino groups challenging. One strategy to overcome this issue has been to utilize step-growth polymerization. For example, poly(β-amino ester)s, (Lynn and Langer, 2000, Zugates et al., 2006 and Green et al., 2008) poly(4-hydroxy-L-proline ester), poly(D-glucaramidoamine), and cationic cyclodextrin-based polymers (Davis et al., 2010) have been synthesized either directly or by post-polymerization modification. Additional polymers are known in the literature (Jerome and Lecomte, 2008, Pounder and Dove, 2010, Tian et al., 2012, Tan et al., 2011, Albertsson and Varma, 2002, Green et al., 2008, Kanasty et al., 2013 and Hao et al., 2013). However, these methods do not offer control over molecular weight and molecular weight distribution. Direct synthesis using controlled chain growth polymerization methods offers greater control over polymer composition and the ability to make block copolymers. Other cationic polymers, such as polyethyleneimine (Philipp et al., 2009, Schroeder et al., 2012, Dahlman et al., 2014) and polylysine, have been widely used as nucleic acid carriers; however, application of these materials to in vivo disease models is often limited by their cytotoxicity and non-degradability. Since incorporating biodegradability will improve biocompatibility and facilitate elimination of materials used in biomedical applications, the development of degradable polymer-based siRNA delivery systems represents an important goal. As such, the development of a polymer containing the desired functional groups such as tertiary amines and alkyl groups is of particular interest.

SUMMARY

In some aspects, the present disclosure provides a polymer of the formula:

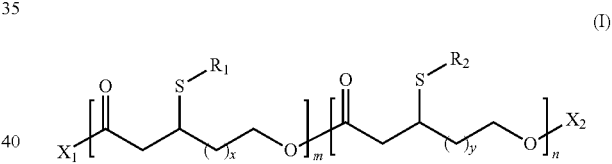

(I)

wherein: $X_1$ is alkyl$_{(C \le 18)}$ or substituted alkyl$_{(C \le 18)}$; $X_2$ is hydrogen, alkyl$_{(C \le 18)}$, or substituted alkyl$_{(C \le 18)}$; $R_1$ is -A-Z; wherein: A is an alkanediyl$_{(C \le 18)}$ or substituted alkanediyl$_{(C \le 18)}$; Z is —$NR_3R_4$; wherein: $R_3$ and $R_4$ are each independently selected from hydrogen, alkyl$_{(C \le 18)}$, substituted alkyl$_{(C \le 18)}$; or $R_3$ and $R_4$ are taken together and are alkanediyl$_{(C \le 18)}$ or substituted alkanediyl$_{(C \le 18)}$; $R_2$ is alkyl$_{(C \le 24)}$, alkenyl$_{(C \le 24)}$, substituted alkyl$_{(C \le 24)}$, or substituted alkenyl$_{(C \le 24)}$; x and y are each independently 0, 1, 2, 3, 4, or 5; m and n are each independently an integer between 0 and 250, provided that at least one of m and n is greater than 1; and the repeating unit defined by m and n are randomly distributed throughout the polymer; or a pharmaceutically acceptable salt thereof. In some embodiments, A is —$CH_2CH_2$—. In some embodiments, Z is —$NR_3R_4$; wherein: $R_3$ and $R_4$ are each independently alkyl$_{(C \le 18)}$ or substituted alkyl$_{(C \le 18)}$. In some embodiments, $R_3$ is alkyl$_{(C \le 18)}$. In some embodiments, $R_3$ is methyl, ethyl, propyl, or butyl. In some embodiments, $R_4$ is alkyl$_{(C \le 18)}$. In some embodiments, $R_4$ is methyl, ethyl, propyl, or butyl. In some embodiments, Z is —$NR_3R_4$; wherein: $R_3$ and $R_4$ are taken together and are alkanediyl$_{(C \le 18)}$ or substituted alkanediyl$_{(C \le 18)}$. In some embodiments, $R_3$ and $R_4$ are taken together and are —$CH_2CH_2CH_2CH_2$—, —$CH_2CH_2CH_2CH_2CH_2$—, or —CH$_2$CH$_2$CH$_2$CH$_2$CH$_2$CH$_2$—. In some embodiments, X$_1$ is alkyl$_{(C≤18)}$ or substituted alkyl$_{(C≤18)}$. In some embodiments, X$_1$ is alkyl$_{(C≤6)}$ or substituted alkyl$_{(C≤6)}$. In some embodiments, X$_1$ is methyl. In some embodiments, X$_2$ is hydrogen. In some embodiments, R$_2$ is alkyl$_{(C≤24)}$. In some embodiments, R$_2$ is butyl, hexyl, octyl, decyl, dodecyl, tetradecyl, hexadecyl, or octadecyl. In some embodiments, x is 1. In some embodiments, y is 1. In some embodiments, m is an integer between 1 and 100. In some embodiments, m is an integer between 1 and 50. In some embodiments, m is 1, 2, 3, 4, 5, 6, 7, 8, 9, 10, 11, 12, 13, 14, 15, 16, 17, 18, 19, or 20. In some embodiments, n is an integer between 1 and 100. In some embodiments, n is an integer between 1 and 50. In some embodiments, n is 1, 2, 3, 4, 5, 6, 7, 8, 9, 10, 11, 12, 13, 14, 15, 16, 17, 18, 19, or 20. In some embodiments, the polymer comprises a molar ratio of the m repeating unit and the n repeating unit between about 10:1 to about 1:10. In some embodiments, the molar ratio between the m repeating unit and the n repeating unit is between about 5:1 to about 1:5. In some embodiments, the molar ratio is 3:1, 1:1, or 1:3. In some embodiments, the polymer has an average molecular weight from about 1,000 to about 100,000 as measured by gel permeation chromatography. In some embodiments, the average molecular weight is about 2,000 to about 10,000.

In yet another aspect, the present disclosure provides a nanoparticle composition comprising:

(A) a polymer of the present disclosure; and
(B) a nucleic acid.

In some embodiments, the nucleic acid is a short (small) interfering RNA (siRNA), a microRNA (miRNA), a messenger RNA (mRNA), a cluster regularly interspaced short palindromic repeats (CRISPR), a plasmid DNA (pDNA), a double stranded DNA (dsDNA), a single stranded DNA (ssDNA), a single stranded RNA (ssRNA), a double stranded RNA (dsRNA), a locked nucleic acid (LNA), a peptide nucleic acid (PNA), a miRNA mimic, or a anti-miRNA. In some embodiments, the nucleic acid is a siRNA. In some embodiments, the siRNA is a siRNA against Factor VII. In some embodiments, the composition further comprises a steroid or steroid derivative. In some embodiments, steroid derivative is a sterol. In some embodiments, the sterol is cholesterol. In some embodiments, the composition further comprises a phospholipid. In some embodiments, the phospholipid is a phosphatidylcholine. In some embodiments, the phospholipid is distearoylphosphatidylcholine. In some embodiments, the composition further comprises a PEG lipid. In some embodiments, the PEG lipid is a PEGylated diacylglycerol. In some embodiments, the PEG lipid is PEGylated dimyristoyl-sn-glycerol. In some embodiments, the PEG lipid is:

wherein: n$_1$ is an integer from 1 to 250; and n$_2$ and n$_3$ are each independently selected from 5, 6, 7, 8, 9, 10, 11, 12, 13, 14, 15, 16, 17, 18, 19, 20, 21, 22, or 23. In some embodiments, n$_1$ is 5 to 100. In some embodiments, n$_1$ is 45. In some embodiments, n$_2$ is 11, 12, 13, 14, 15, 16, or 17. In some embodiments, n$_2$ is 15. In some embodiments, n$_3$ is 11, 12, 13, 14, 15, 16, or 17. In some embodiments, n$_3$ is 15. In some embodiments, the composition comprises a ratio of polymer to steroid to phospholipid to PEG lipid from about 25:15:57:3 to about 75:5:19:1. In some embodiments, the ratio of polymer to steroid to phospholipid to PEG lipid is from about 50:10:30:10 to about 50:10:39.9:0.1. In some embodiments, the composition comprises a ratio of polymer to nucleic acid from about 5:1 to about 500:1. In some embodiments, the composition comprises a ratio from about 10:1 to about 100:1. In some embodiments, the composition comprises a ratio of about 23:1 or about 100:1.

In yet another aspect, the present disclosure provides a method of preparing a nanoparticle composition comprising:

(A) admixing a polymer of the present disclosure in an alcohol$_{(C≤12)}$ to form a nanoparticle; and
(B) admixing a nucleic acid in a buffer to the nanoparticle of step (A) to form a nanoparticle composition.

In some embodiments, the buffer has a pH less than 6. In some embodiments, the buffer has a pH less than 5. In some embodiments, the buffer has a pH of 4.2. In some embodiments, the method further comprises diluting the nanoparticle composition with a second buffer to increase the pH. In some embodiments, the pH is increased to physiological pH. In some embodiments, the second buffer is phosphate buffered saline. In some embodiments, the nucleic acid is a short (small) interfering RNA (siRNA), a microRNA (miRNA), a messenger RNA (mRNA), a cluster regularly interspaced short palindromic repeats (CRISPR), a plasmid DNA (pDNA), a double stranded DNA (dsDNA), a single stranded DNA (ssDNA), a single stranded RNA (ssRNA), a double stranded RNA (dsRNA), a locked nucleic acid (LNA), a peptide nucleic acid (PNA), a miRNA mimic, or a anti-miRNA. In some embodiments, the nucleic acid is a siRNA. In some embodiments, the siRNA is a siRNA against Factor VII. In some embodiments, the composition further comprises a steroid or steroid derivative. In some embodiments, the steroid derivative is a sterol. In some embodiments, the sterol is cholesterol. In some embodiments, the composition further comprises a phospholipid. In some embodiments, the phospholipid is a phosphatidylcholine containing lipid. In some embodiments, the phospholipid is distearoylphosphatidylcholine. In some embodiments, the composition further comprises a PEG lipid. In some embodiments, the PEG lipid is a PEGylated diacyl-

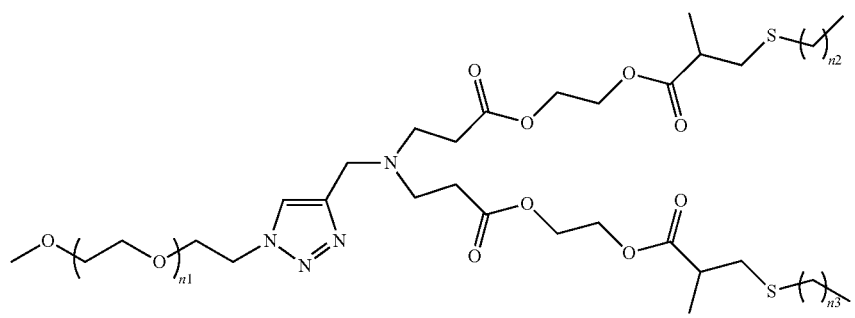

glycerol. In some embodiments, the PEG lipid is PEGylated dimyristoyl-sn-glycerol. In some embodiments, the PEG lipid is:

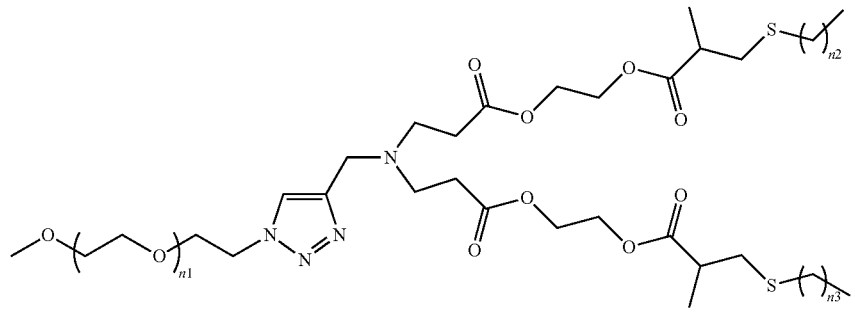

wherein: $n_1$ is an integer from 1 to 250; and $n_2$ and $n_3$ are each independently selected from 5, 6, 7, 8, 9, 10, 11, 12, 13, 14, 15, 16, 17, 18, 19, 20, 21, 22, or 23. In some embodiments, $n_1$ is 5 to 100. In some embodiments, $n_1$ is 45. In some embodiments, $n_2$ is 11, 12, 13, 14, 15, 16, or 17. In some embodiments, $n_2$ is 15. In some embodiments, $n_3$ is 11, 12, 13, 14, 15, 16, or 17. In some embodiments, $n_3$ is 15. In some embodiments, the composition comprises a ratio of polymer to steroid to phospholipid to PEG lipid from about 25:15:57:3 to about 75:5:19:1. In some embodiments, the ratio of polymer to steroid to phospholipid to PEG lipid is from about 50:10:30:10 to about 50:10:39.9:0.1. In some embodiments, the nanoparticle composition comprises a ratio of polymer to nucleic acid from about 5:1 to about 500:1. In some embodiments, the nanoparticle composition comprises a ratio from about 10:1 to about 100:1. In some embodiments, the nanoparticle composition comprises a ratio of about 23:1 or about 100:1.

In yet another aspect, the present disclosure provides a nanoparticle composition prepared by the methods of the present disclosure.

In another aspect, the present disclosure provides a pharmaceutical composition composing a polymer or composition of the present disclosure and an excipient. In some embodiments, the composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularly, intravitreally, liposomally, locally, mucosally, parenterally, rectally, subconjunctival, subcutaneously, sublingually, topically, transbuccally, transdermally, vaginally, in crèmes, in lipid compositions, via a catheter, via a lavage, via continuous infusion, via infusion, via inhalation, via injection, via local delivery, or via localized perfusion.

In still another aspect, the present disclosure provides a method of silencing gene expression comprising contacting a composition comprising a nucleic acid of the present disclosure with a cell comprising said gene. In some embodiments, the nucleic acid is a siRNA. In some embodiments, the cell is contacted in vitro. In some embodiments, the cell is contacted in vivo.

In yet another aspect, the present disclosure provides a method of treating or preventing a disease or disorder comprising administering to a patient in need thereof a therapeutically effective amount of a composition of the present disclosure. The disease or disorder is a disease or disorder associated with an overexpression of one or more genes. In some embodiments, the composition is administered once. In some embodiments, the composition is administered two or more times. In some embodiments, the composition is administered intravenously. In some embodiments, the disease or disorder is associated with overexpression of the genes for Factor VII.

In still another aspect, the present disclosure provides a method of preparing a polymer of the formula:

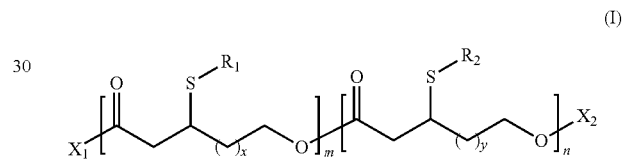

wherein: $X_1$ and $X_2$ are independently selected from hydrogen, alkyl$_{(C \leq 12)}$, or substituted alkyl$_{(C \leq 12)}$; $R_1$ is -A-Z; wherein: A is an alkanediyl$_{(C \leq 12)}$ or substituted alkanediyl$_{(C \leq 12)}$; Z is —NR$_3$R$_4$; wherein: R$_3$ and R$_4$ are each independently selected from hydrogen, alkyl$_{(C \leq 12)}$, substituted alkyl$_{(C \leq 12)}$; or R$_3$ and R$_4$ are taken together and are alkanediyl$_{(C \leq 12)}$ or substituted alkanediyl$_{(C \leq 12)}$; R$_2$ is alkyl$_{(C \leq 24)}$, alkenyl$_{(C \leq 24)}$, substituted alkyl$_{(C \leq 24)}$, or substituted alkenyl$_{(C \leq 24)}$; x and y are each independently 0, 1, 2, 3, 4, or 5; and m and n are each independently an integer between 0 and 250, provided that at least one of m and n is greater than 1; and the repeating unit defined by m and n are randomly distributed throughout the polymer; comprising reacting a first monomer of the formula:

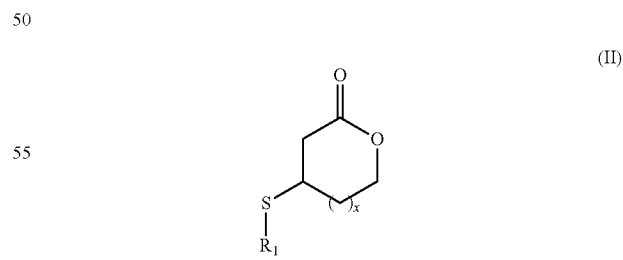

wherein: R$_1$ is -A-Z; wherein: A is an alkanediyl$_{(C \leq 12)}$ or substituted alkanediyl$_{(C \leq 12)}$; Z is —NR$_3$R$_4$; wherein: R$_3$ and R$_4$ are each independently selected from hydrogen, alkyl$_{(C \leq 12)}$, substituted alkyl$_{(C \leq 12)}$; or R$_3$ and R$_4$ are taken together and are alkanediyl$_{(C \leq 12)}$ or substituted alkanediyl$_{(C \leq 12)}$; x is 0, 1, 2, 3, 4, or 5; with a second monomer of the formula:

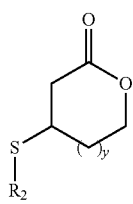

(III)

wherein: $R_2$ is alkyl$_{(C \leq 24)}$, alkenyl$_{(C \leq 24)}$, substituted alkyl$_{(C \leq 24)}$, or substituted alkenyl$_{(C \leq 24)}$; and y is 0, 1, 2, 3, 4, or 5; in the presence of a base. In some embodiments, the base is an alkyllithium reagent. In some embodiments, the base is methyl lithium. In some embodiments, the base is a Grignard reagent. In some embodiments, the base is methyl Grignard. In some embodiments, the method comprises running the reaction in bulk reactant and no solvent. In some embodiments, the method further comprises a solvent. In some embodiments, the solvent is toluene, anisole, dimethyl formamide, dimethyl sulfoxide, chloroform, dichloromethane, dichloroethane, and tetrahydrofuran. In some embodiments, the method comprises reacting for a time period from about 30 seconds to about 1 hour. In some embodiments, the time period is about 2 minutes. In some embodiments, the method comprises a conversion rate greater than 50%. In some embodiments, the conversion rate is greater than 80%. In some embodiments, the polymer has a purity of greater than 80%. In some embodiments, the purity is greater than 95%.

In still another aspect, the present disclosure provides a method of preparing a polymer of the formula:

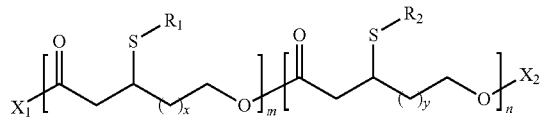

(I)

wherein: $X_1$ and $X_2$ are independently selected from hydrogen, alkyl$_{(C \leq 12)}$, or substituted alkyl$_{(C \leq 12)}$; $R_1$ is -A-Z; wherein: A is an alkanediyl$_{(C \leq 12)}$ or substituted alkanediyl$_{(C \leq 12)}$; Z is —NR$_3$R$_4$; wherein: R$_3$ and R$_4$ are each independently selected from hydrogen, alkyl$_{(C \leq 12)}$, substituted alkyl$_{(C \leq 12)}$; or R$_3$ and R$_4$ are taken together and are alkanediyl$_{(C \leq 12)}$ or substituted alkanediyl$_{(C \leq 12)}$; $R_2$ is alkyl$_{(C \leq 24)}$, alkenyl$_{(C \leq 24)}$, substituted alkyl$_{(C \leq 24)}$, or substituted alkenyl$_{(C \leq 24)}$; x and y are each independently 0, 1, 2, 3, 4, or 5; and m and n are each independently an integer between 0 and 250; provided that either m or n is 0; and the repeating unit defined by m and n are randomly distributed throughout the polymer; comprising reacting a monomer of the formula:

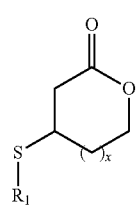

(II)

wherein: $R_1$ is -A-Z; wherein: A is an alkanediyl$_{(C \leq 12)}$ or substituted alkanediyl$_{(C \leq 12)}$; Z is —NR$_3$R$_4$; wherein: R$_3$ and R$_4$ are each independently selected from hydrogen, alkyl$_{(C \leq 12)}$, substituted alkyl$_{(C \leq 12)}$; or R$_3$ and R$_4$ are taken together and are alkanediyl$_{(C \leq 12)}$ or substituted alkanediyl$_{(C \leq 12)}$; x is 0, 1, 2, 3, 4, or 5; or a monomer of the formula:

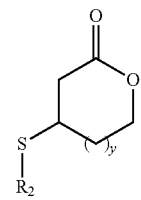

(III)

wherein: $R_2$ is alkyl$_{(C \leq 24)}$, alkenyl$_{(C \leq 24)}$, substituted alkyl$_{(C \leq 24)}$, or substituted alkenyl$_{(C \leq 24)}$; and y is 0, 1, 2, 3, 4, or 5; in the presence of a base.

In still another aspect, the present disclosure provides a composition consisting essentially of:
(A) a polymer of the present disclosure; and
(B) a nucleic acid.

In still another aspect, the present disclosure provides a composition consisting essentially of:
(A) a polymer of the present disclosure;
(B) a PEG lipid; and
(C) a nucleic acid.

In still another aspect, the present disclosure provides a composition consisting essentially of:
(A) a polymer of the present disclosure;
(B) a PEG lipid;
(C) a steroid or steroid derivative; and
(D) a nucleic acid.

In still another aspect, the present disclosure provides a composition consisting essentially of:
(A) a polymer of the present disclosure;
(B) a PEG lipid;
(C) a steroid or steroid derivative;
(D) a phospholipid; and
(E) a nucleic acid.

It is contemplated that any method or composition described herein can be implemented with respect to any other method or composition described herein.

The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, a method, composition, kit, or system that "comprises," "has," "contains," or "includes" one or more recited steps or elements possesses those recited steps or elements, but is not limited to possessing only those steps or elements; it may possess (i.e., cover) elements or steps that are not recited. Likewise, an element of a method, composition, kit, or system that "comprises," "has," "contains," or "includes" one or more recited features possesses those features, but is not limited to possessing only those features; it may possess features that are not recited.

Any embodiment of any of the present methods, composition, kit, and systems may consist of or consist essentially of—rather than comprise/include/contain/have—the described steps and/or features. Thus, in any of the claims, the term "consisting of" or "consisting essentially of" may be substituted for any of the open-ended linking verbs recited above, in order to change the scope of a given claim from what it would otherwise be using the open-ended linking verb.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

As used in this application, the term "average molecular weight" refers to the relationship between the number of moles of each polymer species and the molar mass of that species. In particular, each polymer molecule may have different levels of polymerization and thus a different molar mass. The average molecular weight can be used to represent the molecular weight of a plurality of polymer molecules. Average molecular weight is typically synonymous with average molar mass. In particular, there are three major types of average molecular weight: number average molar mass, weight (mass) average molar mass, and Z-average molar mass. In the context of this application, unless otherwise specified, the average molecular weight represents either the number average molar mass or weight average molar mass of the formula. In some embodiments, the average molecular weight is the number average molar mass. In some embodiments, the average molecular weight may be used to describe a PEG component present in a lipid.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present disclosure. The disclosure may be better understood by reference to one or more of these drawings in combination with the detailed description of specific embodiments presented herein.

(FIG. 4B) Cellular internalization of Cy5.5-siRNA loaded A7 NPs (red) after 3 hr of incubation in HeLa-Luc cells. The cell membrane was stained with CellMask (green). (FIG. 4C) Particle size distribution measured by DLS and (FIG. 4D) TEM image obtained for formulated NP A7.

cholesterol:DSPC:PEG-lipid=50:35:10:5; polymer: siRNA=20:1 (weight); aqueous:EtOH=3:1 (volume)).

Figure 15:
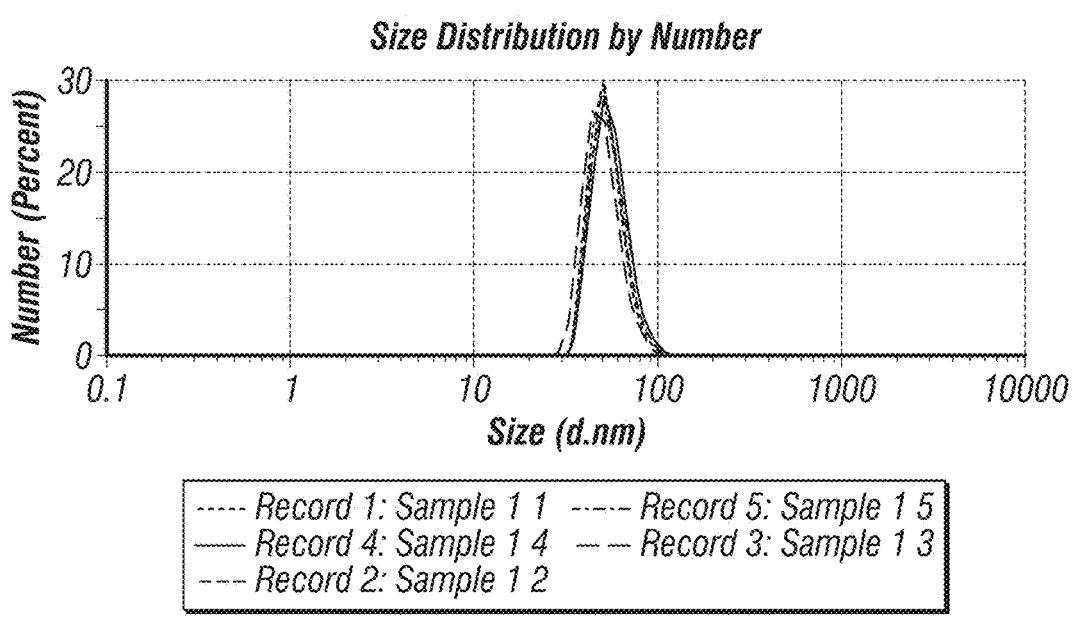

FIG. 15 shows the siRNA NP DLS sizing result. 5 runs of the same sample were performed and overlaid. A1 NPs (A1:cholesterol:DSPC:PEG-lipid=50:35:10:5; polymer: siRNA=20:1 (weight); aqueous:EtOH=3:1 (volume)).

FIGS. 16A & 16B show the GPC trace (FIG. 16A) and photograph of polymerization mixture of viscous polymer A6 synthesized on 1+ gram scale (FIG. 16B).

FIG. 17 shows the degradation study on C7 to confirm hydrolysis of ester bonds in polymer backbone. MW was measured before degradation and after 24 hours.

Figure 18:
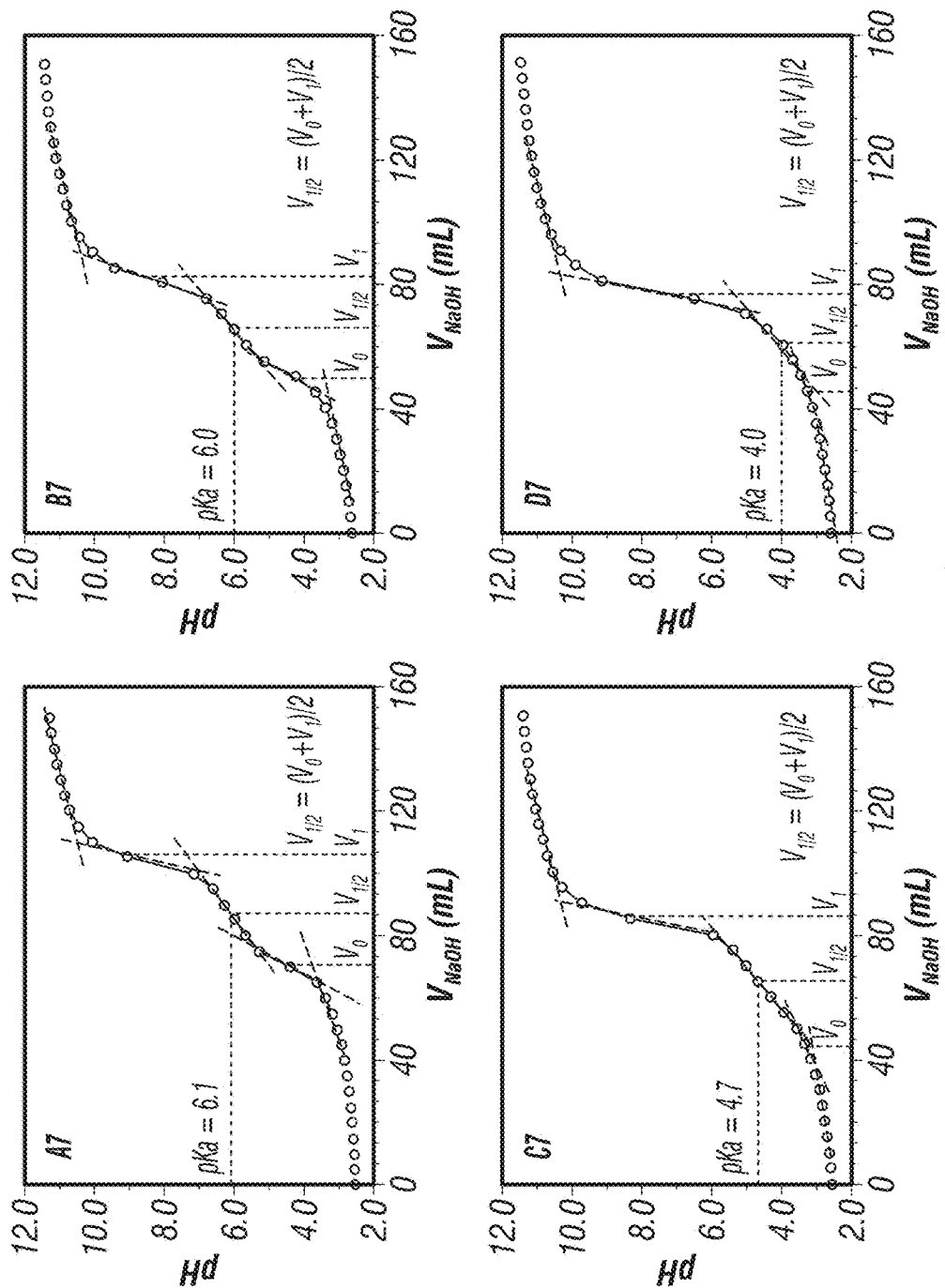

FIG. 18 shows the pH titrations were performed to measure the pKa of a polymer series (A7, B7, C7, and D7).

Figure 19A:
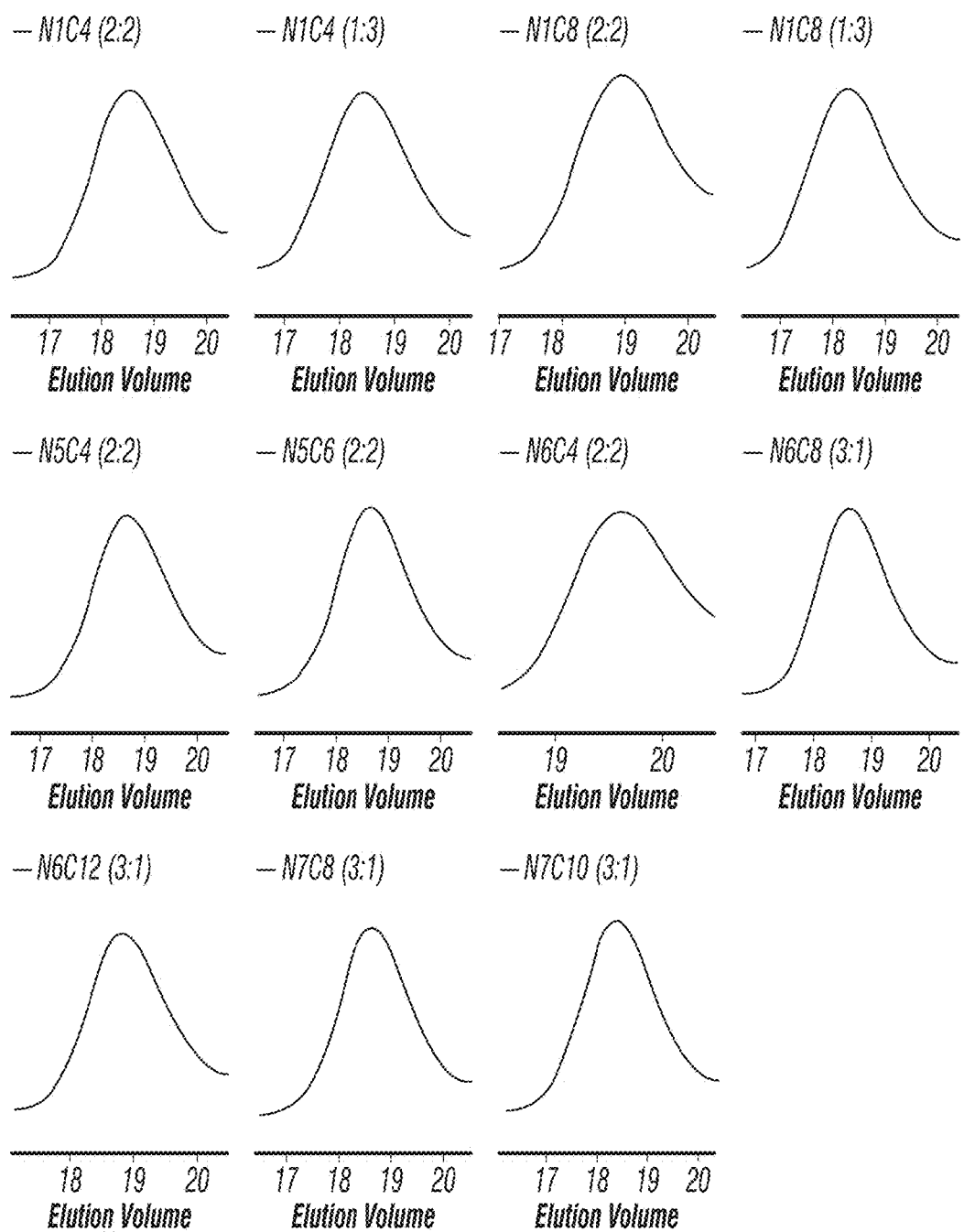
Figure 19B:
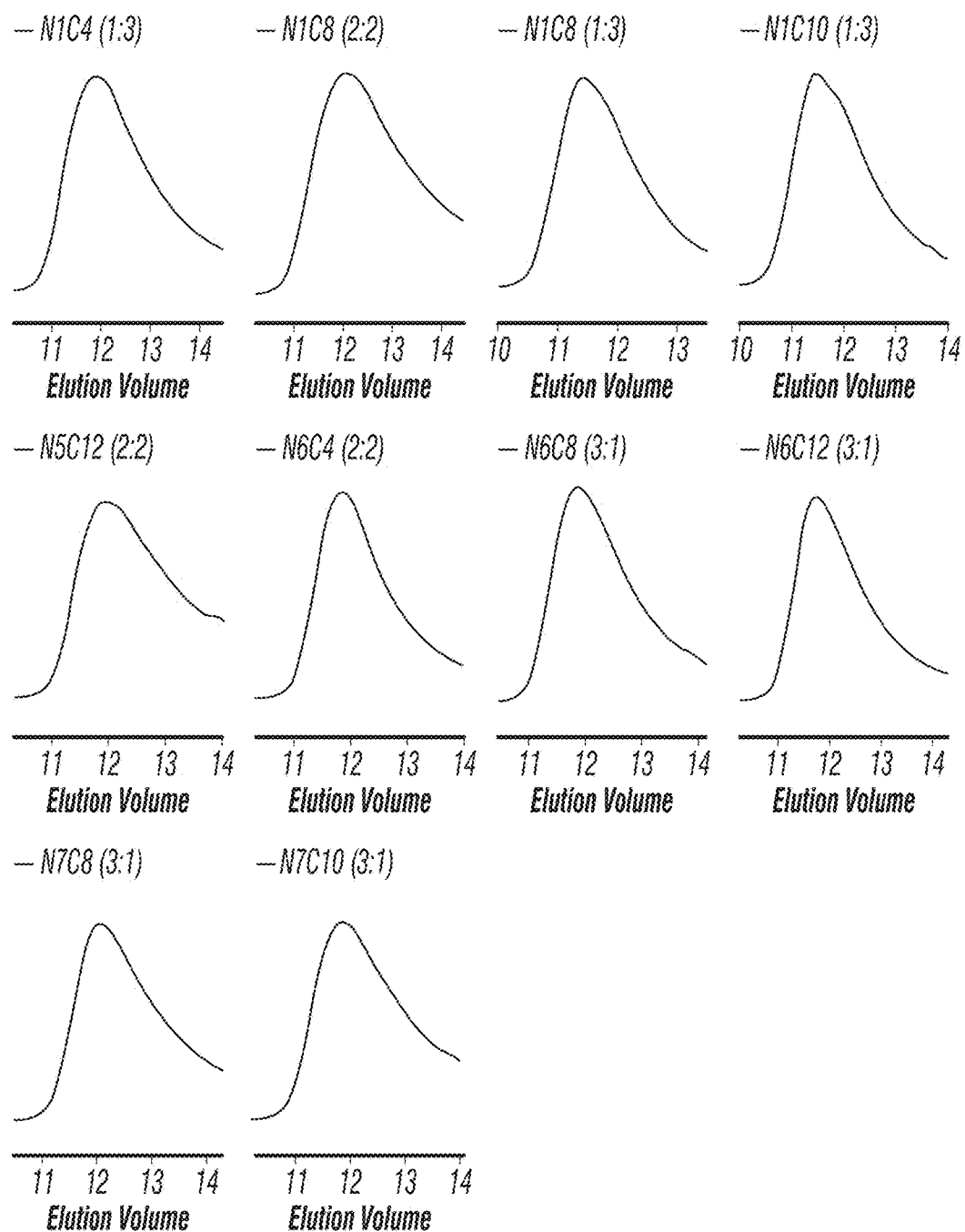

FIGS. 19A & 19B show GPC traces of top performing polymers using DMF line (FIG. 19A) and the THF line (FIG. 19B). Tailing at low MW side is due to amine interactions with the column (no base was added to the THF mobile phase).

DESCRIPTION OF ILLUSTRATIVE EMBODIMENTS

The present disclosure provides a series of lipocationic polyester polymers prepared by a method which allows rapid access to the polymers without a complicated synthetic pathway and the use of protecting groups. In some aspects, these polymers may be used for highly effective short interfering RNA (siRNA) delivery in vitro and in vivo at low doses.

In one aspect, the present disclosure provides degradable lipocationic polyesters that are directly synthesized from tertiary amine bearing valerolactone and alkylated valerolactone monomers via ring-opening polymerization. Using this methodology, thiol modified monomers may be used to create a library of polymers. In this methodology, in some embodiments, initiation with an alkyllithium reagent, such as methyl lithium, promoted rapid polymerization with high monomer conversion (>90%) and decent control over molecular weight. Furthermore, in some embodiments, because functional monomers were polymerized directly, fully functional polymers could be synthesized with quantifiable monomer incorporation. Thus, in some embodiments, cationic and hydrophobic moieties were incorporated at precise ratios, which allows the material composition to be finely tuned and structures correlated with siRNA delivery activity. In another aspect, the present disclosure provides a siRNA-containing nanoparticles that could be stable and active in vivo and methods of preparing these nanoparticles. In some embodiments, formulated polymer nanoparticles exhibited high delivery efficiencies in vitro, enabling >95% knockdown for the top performing material at an siRNA dose of 10 nM. Additionally, in some embodiments, lipocationic polyester NPs also mediate potent gene knockdown in liver hepatocytes after IV administration to mice with siRNA $EC_{50}$ values as low as 1 mg/kg. In some embodiments, high throughput screening of the library reveals a strong correlation between delivery efficiency and chemical structure.

A. CHEMICAL DEFINITIONS

The polymers provided by the present disclosure are shown, for example, above in the summary section and in the claims below. They may be made using the methods outlined in the Examples section. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

Polymers described herein may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the polymers of the present disclosure can have the S or the R configuration.

Polymers of the invention may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the polymer of the present disclosure are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

It should be recognized that the particular anion or cation forming a part of any salt form of a polymer provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means=NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means=S; "sulfonyl" means —S(O)$_2$—; and "sulfinyl" means —S(O)—.

In the context of chemical formulas, the symbol "—" means a single bond, "=" means a double bond, and "≡" means triple bond. The symbol " - - - -" represents an optional bond, which if present is either single or double. The symbol "⩵" represents a single bond or a double bond. Thus, for example, the formula

includes

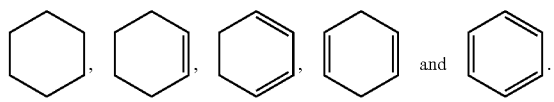

And it is understood that no one such ring atom forms part of more than one double bond. Furthermore, it is noted that the covalent bond symbol "—", when connecting one or two stereogenic atoms, does not indicate any preferred stereochemistry. Instead, it cover all stereoisomers as well as mixtures thereof. The symbol "⌇", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◀" means a single bond where the group attached to the thick end of the wedge is "out of the page." The symbol "◀∥∥" means a single bond where the group attached to the thick end of the wedge is "into the page". The symbol "⌇" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

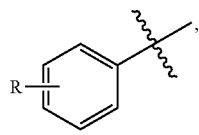

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

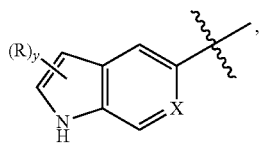

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the number of carbon atoms in the group is as indicated as follows: "Cn" defines the exact number (n) of carbon atoms in the group/class. "C≤n" defines the maximum number (n) of carbon atoms that can be in the group/class, with the minimum number as small as possible for the group in question, e.g., it is understood that the minimum number of carbon atoms in the group "alkenyl$_{(C \leq 8)}$" or the class "alkene$_{(C \leq 8)}$" is two. Compare with "alkoxy$_{(C \leq 10)}$", which designates alkoxy groups having from 1 to 10 carbon atoms. Also compare "phosphine$_{(C \leq 10)}$", which designates phosphine groups having from 0 to 10 carbon atoms. "Cn-n'" defines both the minimum (n) and maximum number (n') of carbon atoms in the group. Thus, "alkyl$_{(C2-10)}$" designates those alkyl groups having from 2 to 10 carbon atoms. Typically the carbon number indicator follows the group it modifies, is enclosed with parentheses, and is written entirely in subscript; however, the indicator may also precede the group, or be written without parentheses, without signifying any change in meaning. Thus, the terms "C5 olefin", "C5-olefin", "olefin$_{(C5)}$", and "olefin$_{C5}$" are all synonymous.

The term "saturated" as used herein means the compound or group so modified has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl).

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "alkenyl" when used without the "substituted" modifier refers to an monovalent unsaturated aliphatic group with a carbon atom as the point of attachment, a linear or branched acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" or "olefin" are synonymous and refer to a compound having the formula H—R, wherein R is alkenyl as this term is defined above. A "terminal alkene" refers to an alkene having just one carbon-carbon double bond, wherein that bond forms a vinyl group at one end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —S(O)$_2$OH, or —S(O)$_2$NH$_2$. The groups —CH=CHF, —CH=CHCl and —CH=CHBr are non-limiting examples of substituted alkenyl groups.

A "base" in the context of this application is a compound which has a lone pair of electron that can accept a proton or a highly polarized bond such that the electron density of the bond is preferentially located on one atom. Non-limiting examples of a base can include triethylamine, a metal hydroxide, a metal alkoxide, a metal hydride, or an organometallic compound such as, but not limited to, an alkyllithium or a Grignard reagent. An alkyllithium is a compound of the formula alkyl$_{(C \leq 12)}$-Li. A metal alkoxide is an alkoxy group wherein the oxygen atom, which was the point of connectivity, has an extra electron and thus a negative charge which is charged balanced by the metal ion. For example, a metal alkoxide could be a sodium tert-butoxide or potassium methoxide.

A "repeat unit" is the simplest structural entity of certain materials, for example, frameworks and/or polymers, whether organic, inorganic or metal-organic. In the case of a polymer chain, repeat units are linked together successively along the chain, like the beads of a necklace. For example, in polyethylene, -[—CH$_2$CH$_2$—]$_n$-, the repeat unit is —CH$_2$CH$_2$—. The subscript "n" denotes the degree of polymerization, that is, the number of repeat units linked together. When the value for "n" is left undefined or where "n" is absent, it simply designates repetition of the formula within the brackets as well as the polymeric nature of the material. The concept of a repeat unit applies equally to where the connectivity between the repeat units extends three dimensionally, such as in metal organic frameworks, modified polymers, thermosetting polymers, etc.

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

B. POLYESTERS AND RING OPENING POLYMERIZATION

The present disclosure provides polymers comprising monomers joined together by esters wherein the alcohol of one monomer is linked together with a carboxylic acid from the other monomer. In some aspects, the polyester polymer of the present disclosure is produced through a step growth methodology. In some embodiments, the polymerization method allows for control of the length and distribution of the monomers with the polymer. In other embodiments, the polymerization method produces a random distribution of monomers within the polymers. One polymerization method that may be used to produce the instant polymers is ring opening polymerization wherein a lactone is hydrolyzed to produce the two polymerization components (e.g. the alcohol and the carboxylic acid). Some non-limiting examples of other ring opening polymerizations to form polyesters are shown below:

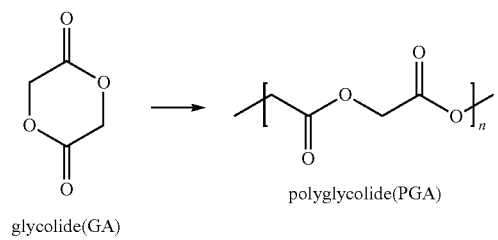

glycolide(GA) → polyglycolide(PGA)

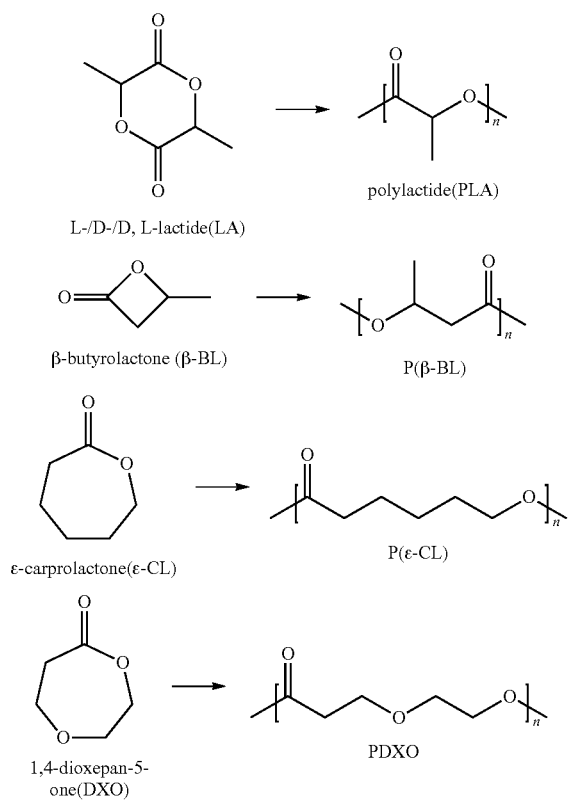

In some embodiments, the ring opening polymerization requires the use of a promoter and/or an initiator. Without being bound by any theory, the promoter facilitates the addition of the hydroxy group to the carboxylic acid. In some embodiments, the initiator faciliates the opening of the lactone ring to produce the reactive intermediates. Furthermore, in some embodiments, a catalyst may be used to promote the ring opening polymerization. In some non-limiting examples, the polymerization may be catalyzed with cationicly, anionicly, or with a metal. In some embodiments, the polymerization methods used to produce the instant polymers are catalyzed with an anion. In some embodiments, the anion is a base with a pKa greater than 15. In some embodiments, the pKa is greater than 20. In some embodiments, the polymerization is catalyzed with an organometallic compound. In some embodiments, the organometallic compound is a Grignard reagent or an alkyl lithium. In some embodiments, the organometallic compound is a methyl lithium or methyl Grignard.

Figure 1A:
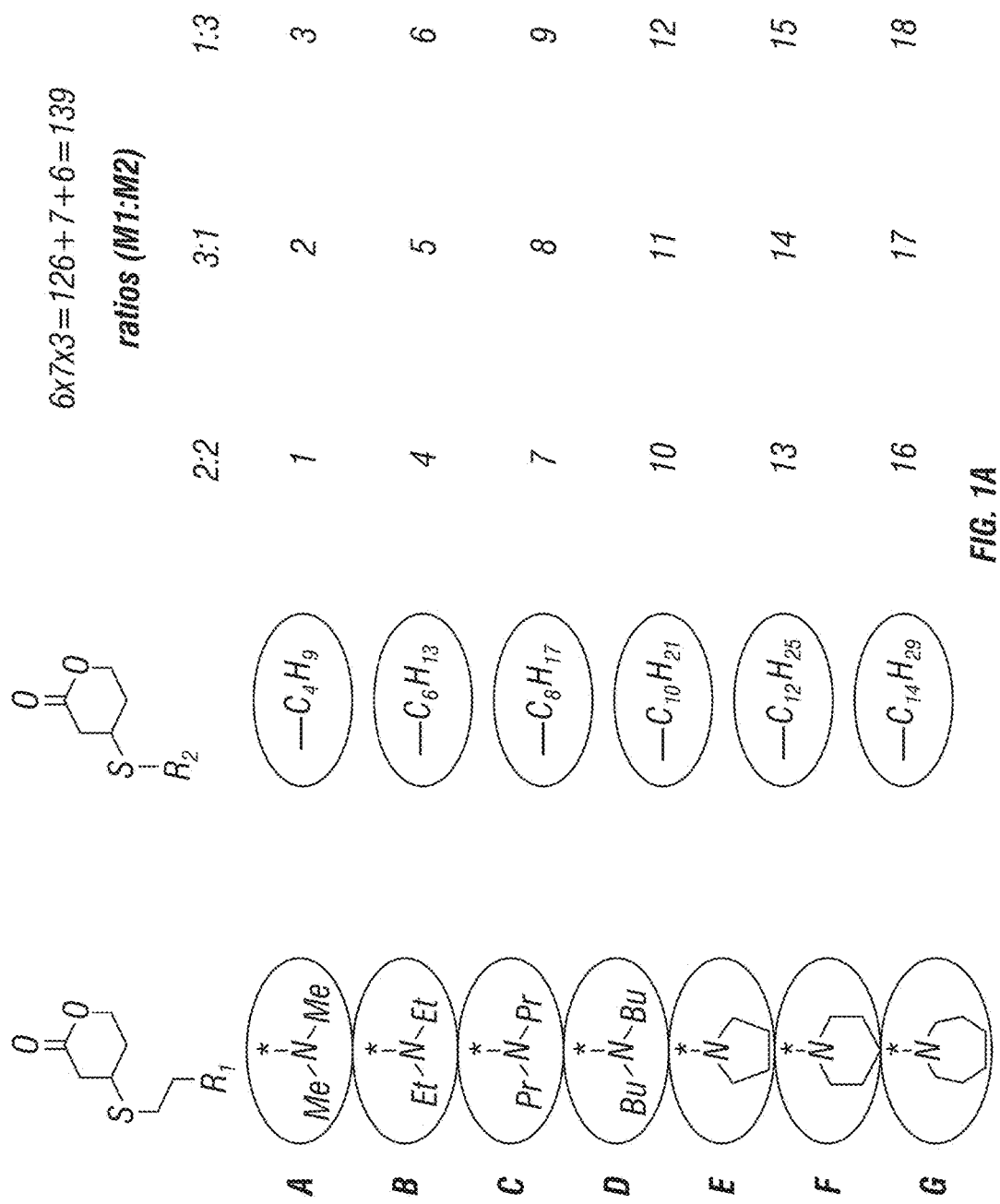
FIGS. 1A-B show the different monomers and ratios of the amino containing monomer and alkyl containing monomer components in the polymer. As used herein, the amino containing monomer is identified by a letter as noted on the left side of the figure and the identity of the alkyl containing monomer and the ratio of the two monomers is identified by a number. The number "0" which is not shown indicates a homopolymer of either the alkyl or amino containing monomer.
Figure 1B:
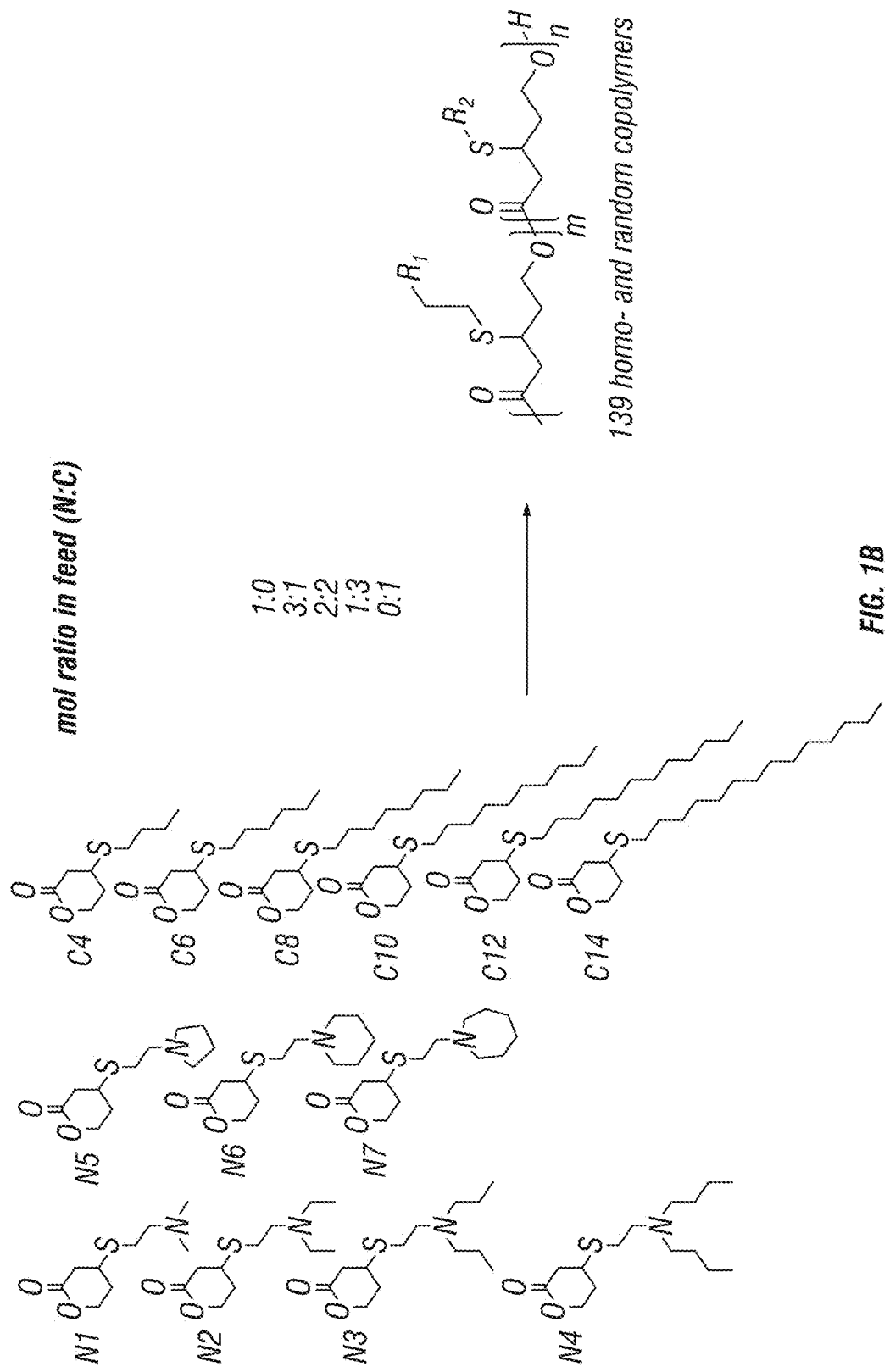

The polymers described herein may be named by a letter corresponding to one of the amine-functionalized valerolactones (A, B, C, D, E, F, G) followed by a number that signifies a combination with an alkyl-functionalized valerolactone. The number signifies the alkyl length and the composition in the feed of the copolymerization. The library consists of different combinations of the two monomer types at three different mole ratios in the feed (3:1, 2:2, and 1:3). See FIG. 1A for details. Alternatively, amine-functionalized valerolactones may be named by the letter N followed by a number (N1, N2, N3, N4, N5, N6, N7)) and alkyl-functionalized valerolactones are named by the letter C followed by a number that corresponds to the carbon length (C4, C6, C8, C10, C12, C14). The resulting copolymers are named by a combination of the two letter codes and brackets that include the monomer feed ratio (mol:mol). For example, A1 can also be termed N1C4 (2:2). G18 can be termed N7C14 (1:3). See FIG. 1B for details. These are the same polymers, with alternative short hand coding nomenclature.

C. LIPIDS

In some aspects of the present disclosure, one or more lipids are mixed with the polymers of the instant disclosure to create a nanoparticle composition. In some embodiments, the polymers are mixed with 1, 2, 3, 4, or 5 different types of lipids. It is contemplated that the polymers can be mixed with multiple different lipids of a single type. In some embodiments, the lipid could be a steroid or a steroid derivative. In other embodiments, the lipid is a PEG lipid. In other embodiments, the lipid is a phospholipid. In other embodiments, the nanoparticle composition comprises a steroid or a steroid derivative, a PEG lipid, and a phospholipid.

1. Steroids and Steroid Derivatives

In some aspects of the present disclosure, the polymers are mixed with one or more steroid or a steroid derivative to create a nanoparticle composition. In some embodiments, the steroid or steroid derivative comprises any steroid or steroid derivative. As used herein, in some embodiments, the term "steroid" is a class of compounds with a four ring 17 carbon cyclic structure which can further comprises one or more substitutions including alkyl groups, alkoxy groups, hydroxy groups, oxo groups, acyl groups, or a double bond between two or more carbon atoms. In one aspect, the ring structure of a steroid comprises three fused cyclohexyl rings and a fused cyclopentyl ring as shown in the formula below:

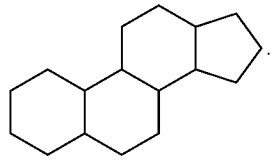 [SMILES: C1CCC2C(C1)CCC1C3CCCC3CCC21]

In some embodiments, a steroid derivative comprises the ring structure above with one or more non-alkyl substitutions. In some embodiments, the steroid or steroid derivative is a sterol wherein the formula is further defined as:

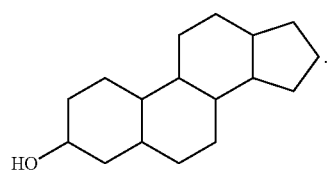 [SMILES: OC1CCC2C(CCC3C4CCCC4CCC23)C1]

In some embodiments of the present disclosure, the steroid or steroid derivative is a cholestane or cholestane derivative. In a cholestane, the ring structure is further defined by the formula:

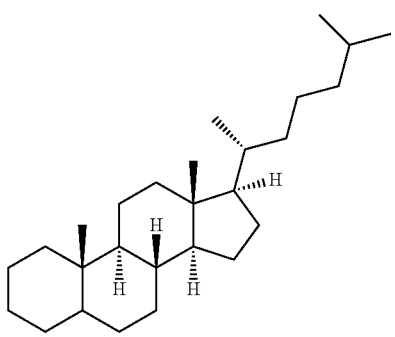

As described above, a cholestane derivative includes one or more non-alkyl substitution of the above ring system. In some embodiments, the cholestane or cholestane derivative is a cholestane or cholestane derivative or a sterol or a sterol derivative. In other embodiments, the cholestane or cholestane derivative is both a cholestere and a sterol or a derivative thereof.

2. PEG or PEGylated Lipid

In some aspects of the present disclosure, the polymers are mixed with one or more PEGylated lipids (or PEG lipid) to create a nanoparticle composition. In some embodiments, the present disclosure comprises using any lipid to which a PEG group has been attached. In some embodiments, the PEG lipid is a diglyceride which also comprises a PEG chain attached to the glycerol group. In other embodiments, the PEG lipid is a compound which contains one or more C6-C24 long chain alkyl or alkenyl group or a C6-C24 fatty acid group attached to a linker group with a PEG chain. Some non-limiting examples of a PEG lipid includes a PEG modified phosphatidylethanolamine and phosphatidic acid, a PEG ceramide conjugated, PEG modified dialkylamines and PEG modified 1,2-diacyloxypropan-3-amines, PEG modified diacylglycerols and dialkylglycerols. In some embodiments, PEG modified diastearoylphosphatidylethanolamine or PEG modified dimyristoyl-sn-glycerol. In some embodiments, the PEG modification is measured by the molecular weight of PEG component of the lipid. In some embodiments, the PEG modification has a molecular weight from about 100 to about 5,000. In some embodiments, the molecular weight is from about 200 to about 500 or from about 1,200 to about 3,000. Some non-limiting examples of lipids that may be used in the present disclosure are taught by U.S. Pat. No. 5,820,873, WO 2010/141069, or U.S. Pat. No. 8,450,298, which is incorporated herein by reference.

In another aspect, the PEG lipid has the formula:

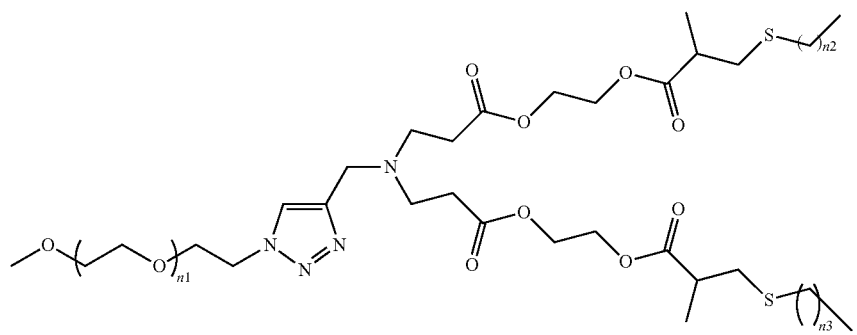

wherein: $n_1$ is an integer between 1 and 100 and $n_2$ and $n_3$ are each independently selected from an integer between 1 and 29. In some embodiments, $n_1$ is 5, 10, 15, 20, 25, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100, or any range derivable therein. In some embodiments, $n_1$ is from about 30 to about 50. In some embodiments, $n_2$ is from 5 to 23. In some embodiments, $n_2$ is 11 to about 17. In some embodiments, $n_3$ is from 5 to 23. In some embodiments, $n_3$ is 11 to about 17.

3. Phospholipid

In some aspects of the present disclosure, the polymers are mixed with one or more phospholipids to create a nanoparticle composition. In some embodiments, any lipid which also comprises a phosphate group. In some embodiments, the phospholipid is a structure which contains one or two long chain C6-C24 alkyl or alkenyl groups, a glycerol or a sphingosine, one or two phosphate groups, and, optionally, a small organic molecule. In some embodiments, the small organic molecule is an amino acid, a sugar, or an amino substituted alkoxy group, such as choline or ethanolamine. In some embodiments, the phospholipid is a phosphatidylcholine. In some embodiments, the phospholipid is distearoylphosphatidylcholine.

D. NUCLEIC ACIDS AND NUCLEIC ACID BASED THERAPEUTIC AGENTS

1. Nucleic Acids

In some aspects of the present disclosure, the nanoparticle compositions comprise one or more nucleic acids. In addition, it should be clear that the present disclosure is not limited to the specific nucleic acids disclosed herein. The present disclosure is not limited in scope to any particular source, sequence, or type of nucleic acid, however, as one of ordinary skill in the art could readily identify related homologs in various other sources of the nucleic acid including nucleic acids from non-human species (e.g., mouse, rat, rabbit, dog, monkey, gibbon, chimp, ape, baboon, cow, pig, horse, sheep, cat and other species). It is contemplated that the nucleic acid used in the present disclosure can comprises a sequence based upon a naturally-occurring sequence. Allowing for the degeneracy of the genetic code, sequences that have at least about 50%, usually at least about 60%, more usually about 70%, most usually about 80%, preferably at least about 90% and most preferably about 95% of nucleotides that are identical to the nucleotide sequence of the naturally-occurring sequence. In another embodiment, the nucleic acid is a complementary sequence to a naturally occurring sequence, or complementary to 75%, 80%, 85%, 90%, 95% and 100%.

In some aspects, the nucleic acid is a sequence which silences, is complimentary to, or replaces another sequence present in vivo. Sequences of 17 bases in length should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100 or more base pairs will be used, although others are contemplated. Longer polynucleotides encoding 250, 500, 1000, 1212, 1500, 2000, 2500, 3000 or longer are contemplated as well.

The nucleic acid used herein may be derived from genomic DNA, i.e., cloned directly from the genome of a particular organism. In preferred embodiments, however, the nucleic acid would comprise complementary DNA (cDNA). Also contemplated is a cDNA plus a natural intron or an intron derived from another gene; such engineered molecules are sometime referred to as "mini-genes." At a minimum, these and other nucleic acids of the present disclosure may be used as molecular weight standards in, for example, gel electrophoresis.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

In some embodiments, the nucleic acid comprises one or more antisense segments which inhibits expression of a gene or gene product. Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

It may be advantageous to combine portions of genomic DNA with cDNA or synthetic sequences to form a siRNA or to generate specific constructs. For example, where an intron is desired in the ultimate construct, a genomic clone will need to be used. The cDNA, siRNA, or a synthesized polynucleotide may provide more convenient restriction sites for the remaining portion of the construct and, therefore, would be used for the rest of the sequence. Other embodiments include dsRNA or ssRNA, which may be used to target genomic sequences or coding/non-coding transcripts.

In other embodiments, the nanoparticles may comprise a nucleic acid which comprises one or more expression vectors are used in a gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al. (1989) and Ausubel et al. (1994), both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

2. siRNA

As mentioned above, the present disclosure contemplates the use of one or more inhibitory nucleic acid for reducing expression and/or activation of a gene or gene product. Examples of an inhibitory nucleic acid include but are not limited to molecules targeted to an nucleic acid sequence, such as an siRNA (small interfering RNA), short hairpin RNA (shRNA), double-stranded RNA, an antisense oligonucleotide, a ribozyme and molecules targeted to a gene or gene product such as an aptamer.

An inhibitory nucleic acid may inhibit the transcription of a gene or prevent the translation of the gene transcript in a cell. An inhibitory nucleic acid may be from 16 to 1000 nucleotides long, and in certain embodiments from 18 to 100 nucleotides long.

Inhibitory nucleic acids are well known in the art. For example, siRNA, shRNA and double-stranded RNA have been described in U.S. Pat. Nos. 6,506,559 and 6,573,099, as well as in U.S. Patent Publications 2003/0051263, 2003/0055020, 2004/0265839, 2002/0168707, 2003/0159161, and 2004/0064842, all of which are herein incorporated by reference in their entirety.

Since the discovery of RNAi by Fire and colleagues in 1998, the biochemical mechanisms have been rapidly characterized. Double stranded RNA (dsRNA) is cleaved by Dicer, which is an RNAase III family ribonuclease. This process yields siRNAs of ~21 nucleotides in length. These siRNAs are incorporated into a multiprotein RNA-induced silencing complex (RISC) that is guided to target mRNA. RISC cleaves the target mRNA in the middle of the complementary region. In mammalian cells, the related microRNAs (miRNAs) are found that are short RNA fragments (~22 nucleotides). miRNAs are generated after Dicer-mediated cleavage of longer (~70 nucleotide) precursors with imperfect hairpin RNA structures. The miRNA is incorporated into a miRNA-protein complex (miRNP), which leads to translational repression of target mRNA.

In designing a nucleic acid capable of generating an RNAi effect, there are several factors that need to be considered such as the nature of the siRNA, the durability of the silencing effect, and the choice of delivery system. To produce an RNAi effect, the siRNA that is introduced into the organism will typically contain exonic sequences. Furthermore, the RNAi process is homology dependent, so the sequences must be carefully selected so as to maximize gene specificity, while minimizing the possibility of cross-interference between homologous, but not gene-specific sequences. Particularly the siRNA exhibits greater than 80, 85, 90, 95, 98% or even 100% identity between the sequence of the siRNA and a portion of a EphA nucleotide sequence. Sequences less than about 80% identical to the target gene are substantially less effective. Thus, the greater identity between the siRNA and the gene to be inhibited, the less likely expression of unrelated genes will be affected.

In addition, the size of the siRNA is an important consideration. In some embodiments, the present disclosure relates to siRNA molecules that include at least about 19-25 nucleotides, and are able to modulate gene expression. In the context of the present disclosure, the siRNA is particularly less than 500, 200, 100, 50, 25, or 20 nucleotides in length. In some embodiments, the siRNA is from about 25 nucleotides to about 35 nucleotides or from about 19 nucleotides to about 25 nucleotides in length.

To improve the effectiveness of siRNA-mediated gene silencing, guidelines for selection of target sites on mRNA have been developed for optimal design of siRNA (Soutschek et al., 2004; Wadhwa et al., 2004). These strategies may allow for rational approaches for selecting siRNA sequences to achieve maximal gene knockdown. To facilitate the entry of siRNA into cells and tissues, a variety of vectors including plasmids and viral vectors such as adenovirus, lentivirus, and retrovirus have been used (Wadhwa et al., 2004).

Within an inhibitory nucleic acid, the components of a nucleic acid need not be of the same type or homogenous throughout (e.g., an inhibitory nucleic acid may comprise a nucleotide and a nucleic acid or nucleotide analog). Typically, an inhibitory nucleic acid form a double-stranded structure; the double-stranded structure may result from two separate nucleic acids that are partially or completely complementary. In certain embodiments of the present disclosure, the inhibitory nucleic acid may comprise only a single nucleic acid (polynucleotide) or nucleic acid analog and form a double-stranded structure by complementing with itself (e.g., forming a hairpin loop). The double-stranded structure of the inhibitory nucleic acid may comprise 16-500 or more contiguous nucleobases, including all ranges derivable thereof. The inhibitory nucleic acid may comprise 17 to 35 contiguous nucleobases, more particularly 18 to 30 contiguous nucleobases, more particularly 19 to 25 nucleobases, more particularly 20 to 23 contiguous nucleobases, or 20 to 22 contiguous nucleobases, or 21 contiguous nucleobases that hybridize with a complementary nucleic acid (which may be another part of the same nucleic acid or a separate complementary nucleic acid) to form a double-stranded structure.

siRNA can be obtained from commercial sources, natural sources, or can be synthesized using any of a number of techniques well-known to those of ordinary skill in the art. For example, commercial sources of predesigned siRNA include Invitrogen's Stealth™ Select technology (Carlsbad, Calif.), Ambion® (Austin, Tex.), and Qiagen® (Valencia, Calif.). An inhibitory nucleic acid that can be applied in the compositions and methods of the present disclosure may be any nucleic acid sequence that has been found by any source to be a validated downregulator of the gene or gene product.

In some embodiments, the disclosure features an isolated siRNA molecule of at least 19 nucleotides, having at least one strand that is substantially complementary to at least ten but no more than thirty consecutive nucleotides of a nucleic acid that encodes a gene, and that reduces the expression of a gene or gene product. In one embodiments of the present disclosure, the siRNA molecule has at least one strand that is substantially complementary to at least ten but no more than thirty consecutive nucleotides of the mRNA that encodes a gene or a gene product.

In one embodiments, the siRNA molecule is at least 75, 80, 85, or 90% homologous, particularly at least 95%, 99%, or 100% similar or identical, or any percentages in between the foregoing (e.g., the disclosure contemplates 75% and greater, 80% and greater, 85% and greater, and so on, and said ranges are intended to include all whole numbers in between), to at least 10 contiguous nucleotides of any of the nucleic acid sequences encoding a target therapeutic protein.

The siRNA may also comprise an alteration of one or more nucleotides. Such alterations can include the addition of non-nucleotide material, such as to the end(s) of the 19 to 25 nucleotide RNA or internally (at one or more nucleotides of the RNA). In certain aspects, the RNA molecule contains a 3'-hydroxyl group. Nucleotides in the RNA molecules of the present disclosure can also comprise non-standard nucleotides, including non-naturally occurring nucleotides or deoxyribonucleotides. The double-stranded oligonucleotide may contain a modified backbone, for example, phosphorothioate, phosphorodithioate, or other modified backbones known in the art, or may contain non-natural internucleoside linkages. Additional modifications of siRNAs (e.g., 2'-O-methyl ribonucleotides, 2'-deoxy-2'-fluoro ribonucleotides, "universal base" nucleotides, 5-C-methyl nucleotides, one or more phosphorothioate internucleotide linkages, and inverted deoxyabasic residue incorporation) can be found in U.S. Publication 2004/0019001 and U.S. Pat. No. 6,673,611 (each of which is incorporated by reference in its entirety). Collectively, all such altered nucleic acids or RNAs described above are referred to as modified siRNAs.

In one embodiment, siRNA is capable of decreasing the expression of a particular genetic product by at least 10%, at least 20%, at least 30%, or at least 40%, at least 50%, at least 60%, or at least 70%, at least 75%, at least 80%, at least 90%, at least 95% or more or any ranges in between the foregoing.

3. Modified Nucleobases

In some embodiments, the nucleic acids of the present disclosure comprise one or more modified nucleosides comprising a modified sugar moiety. Such compounds comprising one or more sugar-modified nucleosides may have desirable properties, such as enhanced nuclease stability or increased binding affinity with a target nucleic acid relative to an oligonucleotide comprising only nucleosides comprising naturally occurring sugar moieties. In some embodiments, modified sugar moieties are substituted sugar moieties. In some embodiments, modified sugar moieties are sugar surrogates. Such sugar surrogates may comprise one or more substitutions corresponding to those of substituted sugar moieties.

In some embodiments, modified sugar moieties are substituted sugar moieties comprising one or more non-bridging sugar substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position is selected from allyl, amino, azido, thio, O-allyl, O—C$_1$-C$_{10}$ alkyl, O—C$_1$-C$_{10}$ substituted alkyl; OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C$_1$-C$_{10}$ alkyl. Examples of sugar substituents at the 5'-position, include, but are not limited to: 5'-methyl (R or S); 5'-vinyl, and 5'-methoxy. In some embodiments, substituted sugars comprise more than one non-bridging sugar substituent, for example, T-F—5'-methyl sugar moieties (see, e.g., PCT International Application WO 2008/101157, for additional 5',2'-bis substituted sugar moieties and nucleosides).

Nucleosides comprising 2'-substituted sugar moieties are referred to as 2'-substituted nucleosides. In some embodiments, a 2'-substituted nucleoside comprises a 2'-substituent group selected from halo, allyl, amino, azido, SH, CN, OCN, CF$_3$, OCF$_3$, O, S, or N(R$_m$)-alkyl; O, S, or N(R$_m$)-alkenyl; O, S or N(R$_m$)-alkynyl; O-alkylenyl-O-alkyl, alkynyl, alkaryl, aralkyl, O-alkaryl, O-aralkyl, O(CH$_2$)$_2$SCH$_3$, O(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In some embodiments, a 2'-substituted nucleoside comprises a 2'-substituent group selected from F, NH$_2$, N$_3$, OCF$_3$, O—CH$_3$, O(CH$_2$)$_3$NH$_2$, CH$_2$—CH=CH$_2$, O—CH$_2$—CH=CH$_2$, OCH$_2$CH$_2$OCH$_3$, O(CH$_2$)$_2$SCH$_3$, O—(CH$_2$)$_2$—O—N(R$_m$)(R$_n$), O(CH$_2$)$_2$O(CH$_2$)$_2$N(CH$_3$)$_2$, and N-substituted acetamide (O—CH$_2$—C(=O)—N(R$_m$)(R$_n$)) where each R$_m$ and R$_n$ is, independently, H, an amino protecting group or substituted or unsubstituted C$_1$-C$_{10}$ alkyl.

In some embodiments, a 2'-substituted nucleoside comprises a sugar moiety comprising a 2'-substituent group selected from F, OCF$_3$, O—CH$_3$, OCH$_2$CH$_2$OCH$_3$, O(CH$_2$)$_2$ SCH$_3$, O(CH$_2$)$_2$—O—N(CH$_3$)$_2$, —O(CH$_2$)$_2$O (CH$_2$)$_2$N(CH$_3$)$_2$, and O—CH$_2$—C(=O)—N(H)CH$_3$.

In some embodiments, a 2'-substituted nucleoside comprises a sugar moiety comprising a 2'-substituent group selected from F, O—CH$_3$, and OCH$_2$CH$_2$OCH$_3$.

Certain modified sugar moieties comprise a bridging sugar substituent that forms a second ring resulting in a bicyclic sugar moiety. In some such embodiments, the bicyclic sugar moiety comprises a bridge between the 4' and the 2' furanose ring atoms. Examples of such 4' to 2' sugar substituents, include, but are not limited to: —[C(R$_a$)(R$_b$)]$_n$—, —[C(R$_a$)(R$_b$)]$_n$—O—, —C(R$_a$R$_b$)—N(R)—O— or, —C(R$_a$R$_b$)—O—N(R)—; 4'-CH$_2$-2', 4'-(CH$_2$)$_2$-2', 4'-(CH$_2$)—O—2' (LNA); 4'-(CH$_2$)—S-2'; 4'-(CH$_2$)$_2$—O-2' (ENA); 4'-CH(CH$_3$)—O-2' (cEt) and 4'-CH(CH$_2$OCH$_3$)—O-2', and analogs thereof (see, e.g., U.S. Pat. No. 7,399, 845); 4'-C(CH$_3$)(CH$_3$)—O-2' and analogs thereof, (see, e.g., WO 2009/006478); 4'-CH$_2$—N(OCH$_3$)-2' and analogs thereof (see, e.g., WO2008/150729); 4'-CH$_2$—O—N(CH$_3$)-2' (see, e.g., US2004/0171570, published Sep. 2, 2004); 4'-CH$_2$—O—N(R)-2', and 4'-CH$_2$—N(R)—O-2'-, wherein each R is, independently, H, a protecting group, or C$_1$-C$_{12}$ alkyl; 4'-CH$_2$—N(R)—O-2', wherein R is H, C$_1$-C$_{12}$ alkyl, or a protecting group (see, U.S. Pat. No. 7,427,672); 4'-CH$_2$—C(H)(CH$_3$)-2' (see, e.g., Chattopadhyaya et al., J. Org. Chem., 2009, 74, 118-134); and 4'-CH$_2$—C(=CH$_2$)-2' and analogs thereof (see, PCT International Application WO 2008/154401).

In some embodiments, such 4' to 2' bridges independently comprise from 1 to 4 linked groups independently selected from —[C(R$_a$)(R$_b$)]$_n$—, —C(R$_a$)=C(R$_b$)—, —C(R$_a$)

=N—, —C(=O)—, —C(=S)—, —Si($R_a$)$_2$—, —S(=O)$_x$—, and —N($R_a$)—; wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-$CH_2$—O—2') BNA, (B) β-D-Methyleneoxy (4'-$CH_2$—O-2') BNA (also referred to as locked nucleic acid or LNA), (C) Ethyleneoxy (4'-($CH_2$)$_2$—O-2') BNA, (D) Aminooxy (4'-$CH_2$—O—N(R)-2') BNA, (E) Oxyamino (4'-$CH_2$—N(R)—O-2') BNA, (F) Methyl(methyleneoxy) (4'-CH($CH_3$)—O-2') BNA (also referred to as constrained ethyl or cEt), (G) methylene-thio (4'-$CH_2$—S-2') BNA, (H) methylene-amino (4'-$CH_2$—N(R)-2') BNA, (I) methyl carbocyclic (4'-$CH_2$—CH($CH_3$)-2') BNA, (J) propylene carbocyclic (4'-($CH_2$)$_3$-2') BNA, and (K) Methoxy(ethyleneoxy) (4'-CH($CH_2$OMe)—O—2') BNA (also referred to as constrained MOE or cMOE).

Additional bicyclic sugar moieties are known in the art, for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 129(26) 8362-8379 (Jul. 4, 2007); Elayadi et al., Curr. Opinion Invens. Drugs, 2001, 2, 5561; Braasch et al., Chem. Biol., 2001, 8, 1-7; Orum et al., Curr. Opinion Mol. Ther., 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US 2004/0171570, US 2007/0287831, and US 2008/0039618; U.S. Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In some embodiments, bicyclic sugar moieties and nucleosides incorporating such bicyclic sugar moieties are further defined by isomeric configuration. For example, a nucleoside comprising a 4'-2' methylene-oxy bridge, may be in the .alpha.-L configuration or in the .beta.-D configuration. Previously, α-L-methyleneoxy (4'-$CH_2$—O-2') bicyclic nucleosides have been incorporated into antisense oligonucleotides that showed antisense activity (Frieden et al., Nucleic Acids Research, 2003, 21, 6365-6372).

In some embodiments, substituted sugar moieties comprise one or more non-bridging sugar substituent and one or more bridging sugar substituent (e.g., 5'-substituted and 4'-2' bridged sugars; PCT International Application WO 2007/134181, wherein LNA is substituted with, for example, a 5'-methyl or a 5'-vinyl group).

In some embodiments, modified sugar moieties are sugar surrogates. In some such embodiments, the oxygen atom of the naturally occurring sugar is substituted, e.g., with a sulfer, carbon or nitrogen atom. In some such embodiments, such modified sugar moiety also comprises bridging and/or non-bridging substituents as described above. For example, certain sugar surrogates comprise a 4'-sulfur atom and a substitution at the 2'-position (see, e.g., published U.S. Patent Application US 2005/0130923) and/or the 5' position. By way of additional example, carbocyclic bicyclic nucleosides having a 4'-2' bridge have been described (see, e.g., Freier et al., Nucleic Acids Research, 1997, 25(22), 4429-4443 and Albaek et al., J. Org. Chem., 2006, 71, 7731-7740).

In some embodiments, sugar surrogates comprise rings having other than 5-atoms. For example, in some embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. Bioorg. & Med. Chem. (2002) 10: 841-854), and fluoro HNA (F-HNA).

In some embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In some embodiments, at least one of $q_1$, $q_2$, $q_3$, $q_4$, $q_5$, $q_6$ and $q_7$ is methyl. In some embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclo and tricyclo sugar surrogate ring systems are also known in the art that can be used to modify nucleosides for incorporation into antisense compounds (see, e.g., review article: Leumann, J. C, Bioorganic & Medicinal Chemistry, 2002, 10, 841-854).

Combinations of modifications are also provided without limitation, such as 2'-F-5'-methyl substituted nucleosides (see PCT International Application WO 2008/101157 for other disclosed 5',2'-bis substituted nucleosides) and replacement of the ribosyl ring oxygen atom with S and further substitution at the 2'-position (see U.S. Patent Publication US 2005/0130923) or alternatively 5'-substitution of a bicyclic nucleic acid (see PCT International Application WO 2007/134181 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., J. Am. Chem. Soc. 2007, 129(26), 8362-8379).

In some embodiments, the present disclosure provides oligonucleotides comprising modified nucleosides. Those modified nucleotides may include modified sugars, modified nucleobases, and/or modified linkages. The specific modifications are selected such that the resulting oligonucleotides possess desirable characteristics. In some embodiments, oligonucleotides comprise one or more RNA-like nucleosides. In some embodiments, oligonucleotides comprise one or more DNA-like nucleotides.

In some embodiments, nucleosides of the present disclosure comprise one or more unmodified nucleobases. In certain embodiments, nucleosides of the present disclosure comprise one or more modified nucleobases.

In some embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl $CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine ([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g., 9-(2-aminoethoxy)-H-pyrimido[5,4-13][1,4]benzoxazin-2(3H)-one), carbazole cytidine ($^2$H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, Kroschwitz, J. I., Ed., John Wiley & Sons, 1990, 858-859; those disclosed by Englisch et al., Angewandte Chemie, International Edition, 1991, 30, 613; and those disclosed by Sanghvi, Y. S., Chapter 15, Antisense Research and Applications, Crooke, S. T. and Lebleu, B., Eds., CRC Press, 1993, 273-288.

Representative United States Patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, each of which is herein incorporated by reference in its entirety.

In some embodiments, the present disclosure provides oligonucleotides comprising linked nucleosides. In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino (—$CH_2$—N($CH_3$)—O—$CH_2$—), thiodiester (—O—C(O)—S—), thionocarbamate (—O—C(O)(NH)—S—); siloxane (—O—Si(H)$_2$—O—); and N,N'-dimethylhydrazine (—$CH_2$—N($CH_3$)—N($CH_3$)—). Modified linkages, compared to natural phosphodiester linkages, can be used to alter, typically increase, nuclease resistance of the oligonucleotide. In some embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-$CH_2$—N($CH_3$)—O-5'), amide-3 (3'-$CH_2$—C(=O)—N(H)-5'), amide-4 (3'-$CH_2$—N(H)—C(=O)-5'), formacetal (3'-O—$CH_2$—O-5'), and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

Additional modifications may also be made at other positions on the oligonucleotide, particularly the 3' position of the sugar on the 3' terminal nucleotide and the 5' position of 5' terminal nucleotide. For example, one additional modification of the ligand conjugated oligonucleotides of the present disclosure involves chemically linking to the oligonucleotide one or more additional non-ligand moieties or conjugates which enhance the activity, cellular distribution or cellular uptake of the oligonucleotide. Such moieties include but are not limited to lipid moieties such as a cholesterol moiety (Letsinger et al., Proc. Natl. Acad. Sci. USA, 1989, 86, 6553), cholic acid (Manoharan et al., Bioorg. Med. Chem. Lett., 1994, 4, 1053), a thioether, e.g., hexyl-5-tritylthiol (Manoharan et al., Ann. N.Y. Acad. Sci., 1992, 660, 306; Manoharan et al., Bioorg. Med. Chem. Lett., 1993, 3, 2765), a thiocholesterol (Oberhauser et al., Nucl. Acids Res., 1992, 20, 533), an aliphatic chain, e.g., dodecandiol or undecyl residues (Saison-Behmoaras et al., EMBO J., 1991, 10, 111; Kabanov et al., FEBS Lett., 1990, 259, 327; Svinarchuk et al., Biochimie, 1993, 75, 49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651; Shea et al., Nucl. Acids Res., 1990, 18, 3777), a polyamine or a polyethylene glycol chain (Manoharan et al., Nucleosides & Nucleotides, 1995, 14, 969), or adamantane acetic acid (Manoharan et al., Tetrahedron Lett., 1995, 36, 3651), a palmityl moiety (Mishra et al., Biochim. Biophys. Acta, 1995, 1264, 229), or an octadecylamine or hexylaminocarbonyl-oxycholesterol moiety (Crooke et al., J. Pharmacol. Exp. Ther., 1996, 277, 923).

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762, 779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

E. KITS

The present disclosure also provides kits. Any of the components disclosed herein may be combined in the form of a kit. In some embodiments, the kits comprise a polyester polymer or a composition as described above or in the claims.

The kits will generally include at least one vial, test tube, flask, bottle, syringe or other container, into which a component may be placed, and preferably, suitably aliquoted. Where there is more than one component in the kit, the kit also will generally contain a second, third or other additional containers into which the additional components may be separately placed. However, various combinations of components may be comprised in a container. In some embodiments, all of the siRNA delivery components are combined in a single container. In other embodiments, some or all of the siRNA delivery components with the instant polymers are provided in separate containers.

The kits of the present disclosure also will typically include packaging for containing the various containers in close confinement for commercial sale. Such packaging may include cardboard or injection or blow molded plastic packaging into which the desired containers are retained. A kit may also include instructions for employing the kit components. Instructions may include variations that can be implemented.

F. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1: Materials and Instrumentation

1. Materials
Ethylene sulfide, cholesterol, all thiols, all amines, and all otherwise unspecified chemicals were purchased from Sigma-Aldrich. 5,6-dihydro-2H-pyran-2-one (DPO) and luciferin (monosodium salt) were purchased from Fisher Scientific. DSPC was purchased from Avanti Lipids. siRNA against luciferase (sense strand: 5'-GAUUAUGUCCG-GUUAUGUA[dT][dT]-3' (SEQ ID NO: 1); anti-sense strand: 3'-UACAUAACCGGACAUAAUC[dT][dT]-5' (SEQ ID NO: 2)), Dulbecco's Modified Eagle Media (DMEM), and fetal bovine serum (FBS) were purchased from Sigma-Aldrich. Cy5.5-siLuc had the same sequence, but was labeled with the Cy5.5 dye at one end. PEG-lipid was chemically synthesized. OptiMEM was purchased from Life Technologies. RNAiMax was purchased from Invitrogen and used following the supplier's recommended protocols. Cell Mask Orange was purchased from Molecular Probes. ONE-Glo+Tox was purchased from Promega. All organic solvents were purchased from Fisher Scientific and purified with a solvent purification system (Innovative Technology).

2. Instrumentation
Robotic automation. Nanoparticle (NP) formulations and in vitro screening were performed on a Tecan Freedom EVO 200 fluid handling robot equipped with an 8-channel liquid handling arm (LiHa), multi-channel arm with 96-channel head (MCA), robotic manipulator arm (RoMa), and an integrated InfiniTe F/M200 Pro microplate reader (Tecan). Two integrated custom heating and stirring chemical reaction stations (V&P Scientific 710E-3HM Series Tumble Stirrers) provided reaction and mixing support. All operations were programmed in EVOware Standard software (Tecan).

Nuclear magnetic resonance (NMR) spectroscopy. $^1$H and $^{13}$C NMR were performed on a Varian® 500 MHz spectrometer.

Molecular weight analysis. For polymers soluble in DMF, the molecular weight was measured by Gel Permeation Chromatography (GPC) (Viscotek) equipped with RI detection and ViscoGEL I-series columns (Viscoteck I-MBLMW-3078) using DMF as the eluent at 0.75 mL/min and 45° C. For polymers not soluble in DMF, the molecular weight were measured by GPC with THF as the eluent at 1 mL/min and 35° C. (Malvern/Viscotek) equipped with an RI detector (Malvern/Viscotek). The instruments were calibrated with a series of 10 narrow polydispersity polystyrene standards (500 to 200,000 g/mol).

Flash chromatography. Flash chromatography was performed on a Teledyne Isco CombiFlash® Rf-200i chromatography system equipped with UV-vis and evaporative light scattering detectors (ELSD).

Transmission Electron Microscopy (TEM) was performed on a FEI Tecnai G2 Spirit Biotwin at an accelerated voltage of 120 kW. For sample preparation, a drop of formulated NP was placed on a carbon film covered TEM grid, excess liquid was then wicked by filter paper. The copper grid was then dried under vacuum for one hour.

NP size analysis. Particle sizes were measured by Dynamic Light Scattering (DLS) using a Malvern Zetasizer Nano ZS (He—Ne laser, λ=632 nm).

Nanoparticle formulation for in vivo studies. Formulated polymeric nanoparticles for in vivo studies were prepared using a microfluidic mixing instrument with herringbone rapid mixing features (Precision Nanosystems NanoAssemblr). Ethanol solutions of polymers, DSPC, cholesterol, and PEG lipid were rapidly combined with acidic solutions of siRNA as described below. The typical ratio of aqueous: EtOH was 3:1 (volume) and the typical flow rate was 12 mL/minute.

3. In Vitro siRNA Transfection Assay
HeLa cells stably expressing luciferase (HeLa-Luc) were derived from HeLa cells (ATCC) by stable transfection of the Firefly Luciferase gene using Lentiviral infection followed by clonal selection. HeLa-Luc cells were seeded (10,000 cells/well) into each well of an opaque white 96-well plate (Corning) and allowed to attach overnight in phenol red-free DMEM supplemented with 5% FBS. Polymer stock solutions were diluted to 1 mM in ethanol. 58.45 μL DSPC/Cholesterol/PEG lipid mixture in EtOH (DPSC=211.14 μM, Chol=802.33 μM, PEG Lipid=42.228

μM) was mixed with 61.55 μL polymer (1 mM stock solution in EtOH). This was mixed thoroughly by pipette mixing. 33 μL of this ethanol lipid mixture was added to 55 μL siRNA stock solution in citrate buffer (40 ng/μL siRNA) (citrate buffer pH=4.2) and rapidly mixed. It was allowed to complex for 20 minutes at room temperature. 132 μL sterile PBS was added to complete the preparation of formulated NPs. 20, 10, 5, 2.5, and 1.5 μL were added to growing cells (n=4) depending on desired dose.

Figure 6:
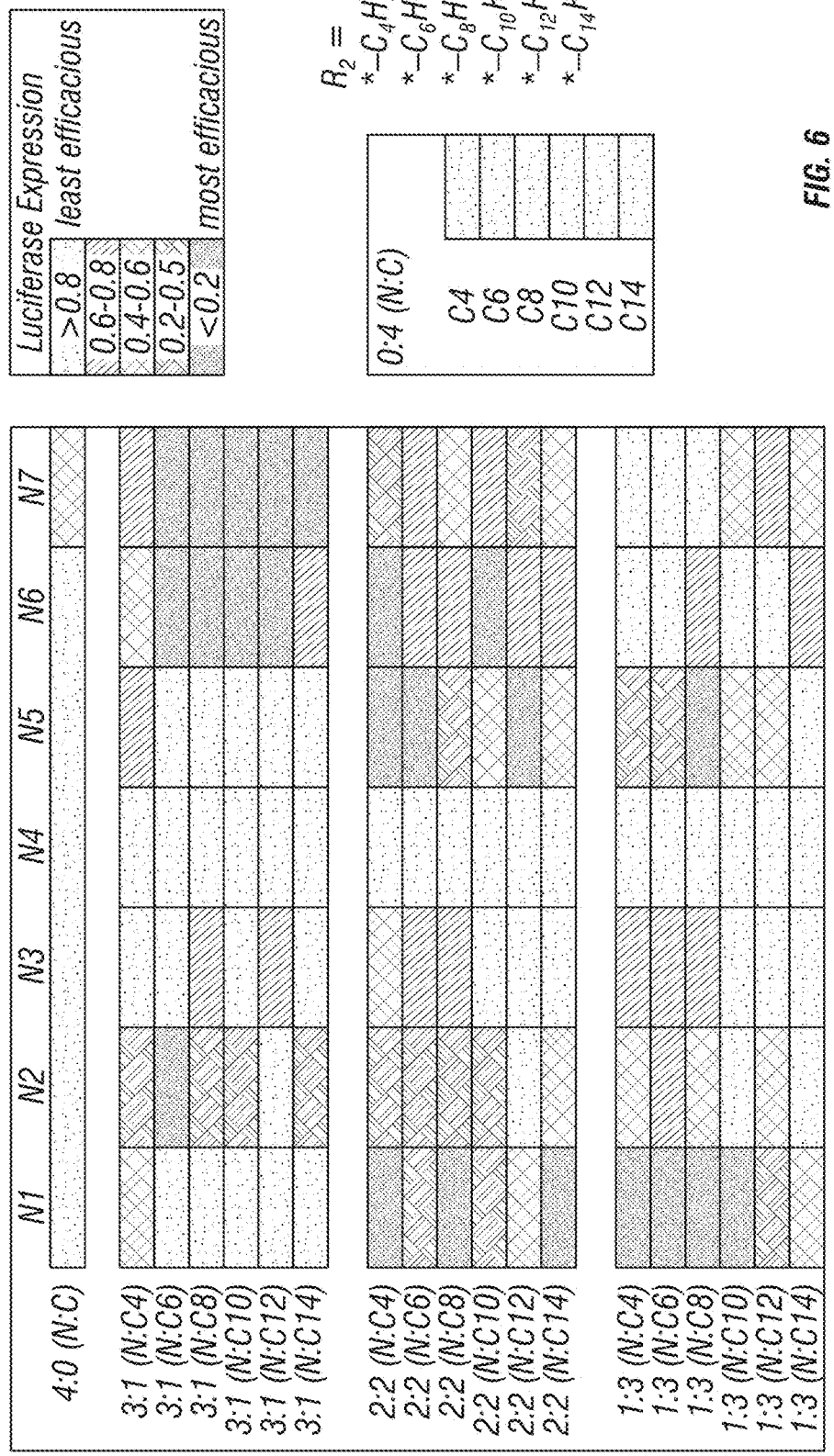
FIG. 6 shows a heat map relating the polymer's monomer composition to the efficacy of the nanoparticle in inhibiting in vitro luciferase expression in HeLa cells.
Figure 7:
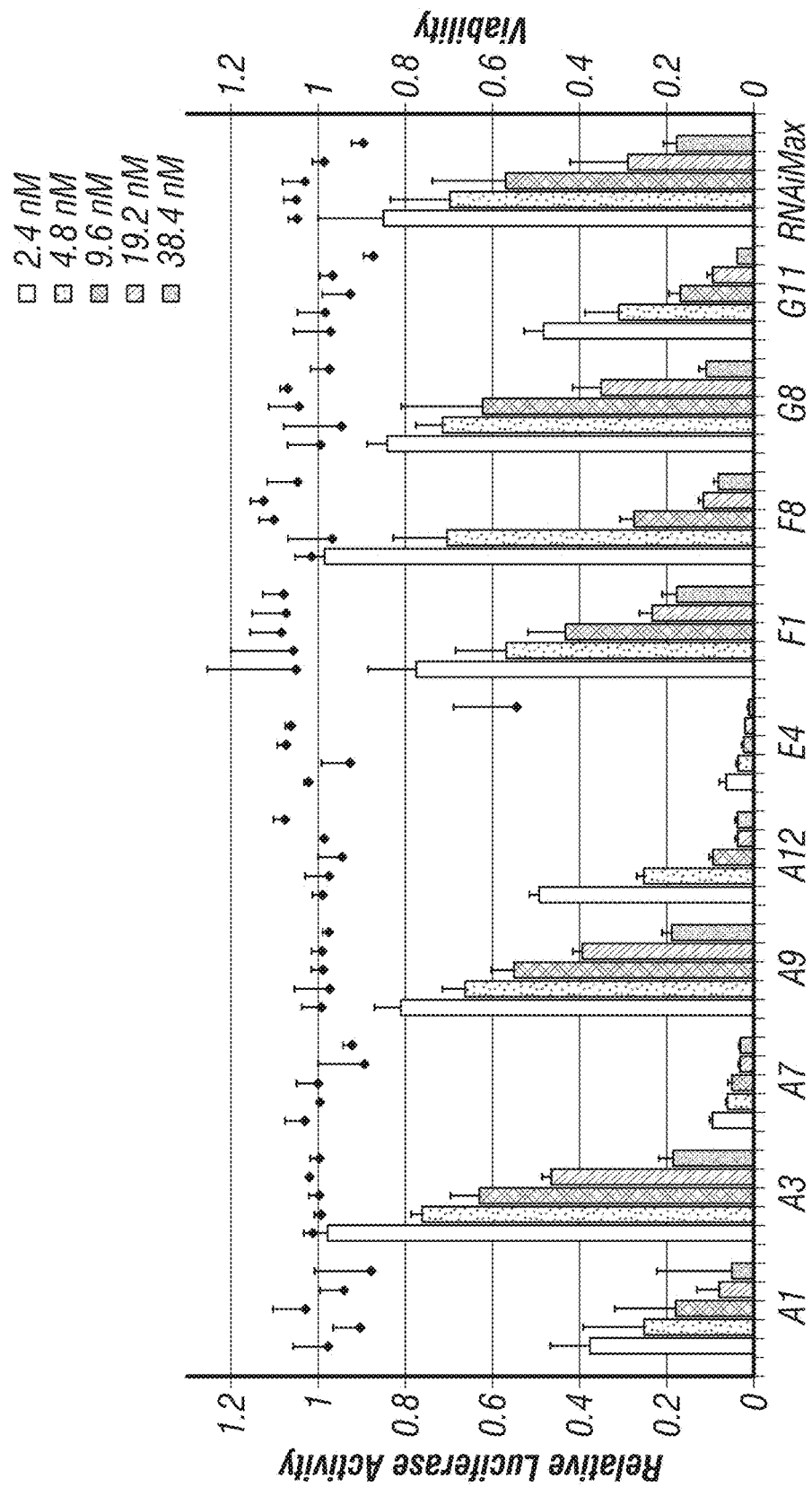
FIG. 7 shows a dose-response of silencing in Hela-Luc cells for several polymers as a function of luciferase activity. The dose scale is 6.25 ng (2.4 nM), 12.5 ng (4.8 nM), 25 ng (9.6 nM), 50 ng (19.2 nM), and 100 ng (38.4 nM) going from left to right. Bars represent relative luciferase activity, while dots represent cell viability. Results were normalized to untreated cells (n=4). A7 (2:2) vs. RNAiMax: * * * * $P<0.0001$.
Figure 8:
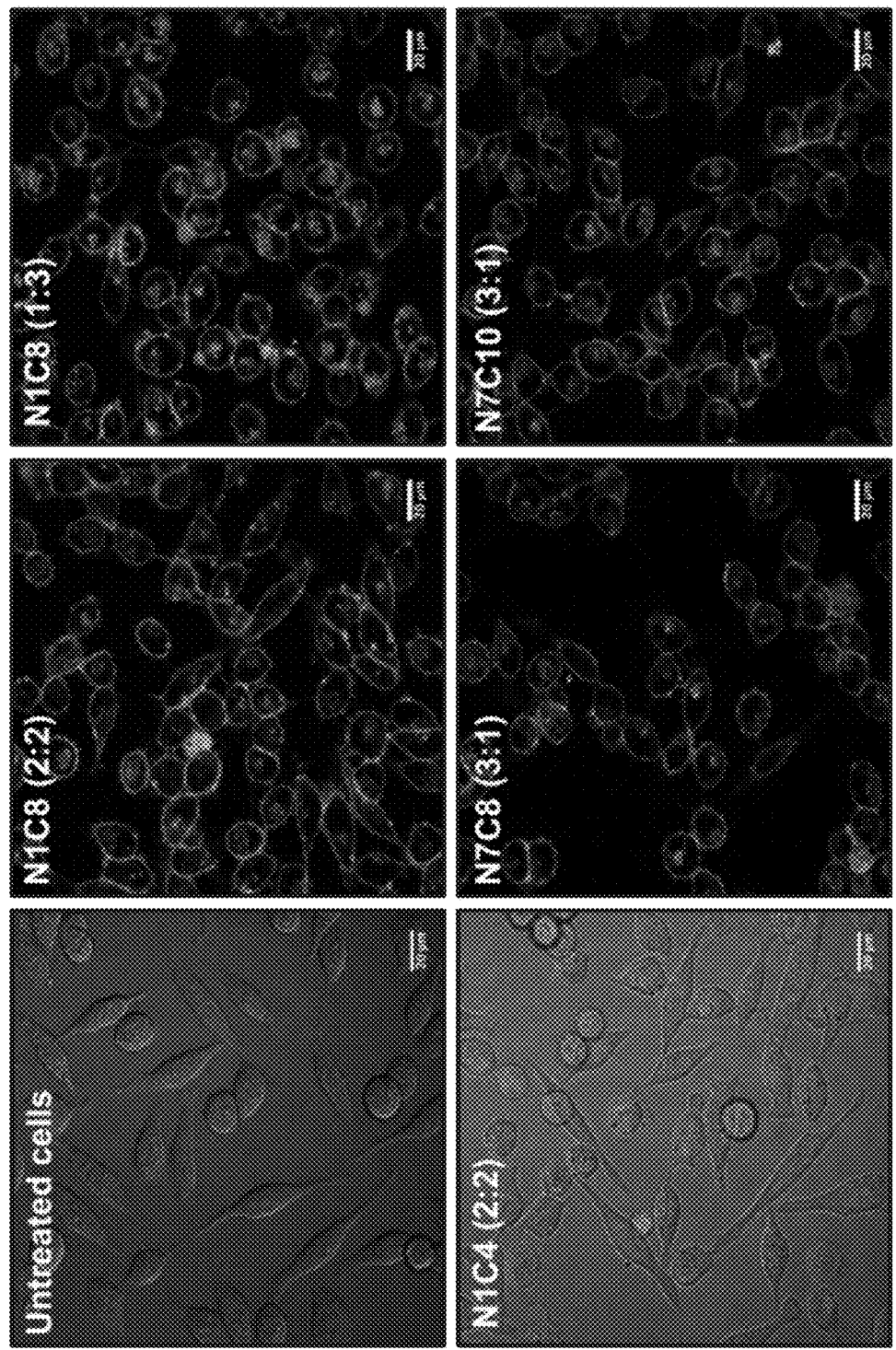
FIG. 8 shows the cellular uptake of formulated Cy5.5-siLuc containing nanoparticles. The NPs are red and the cell membrane is green (Cell Mask Orange).

For the high-throughput screen (FIGS. 5-6), cells were transfected with 100 ng (38.4 nM) of firefly-specific siLuc. Crude polymers were utilized in this phase to screen for hits. Subsequently, the inventors re-synthesized lead polymers and purified them by dialysis into THF. All polymers used in the dose response (FIGS. 7A & 7B) and animal experiments (FIGS. 10A-10C) were purified polymers free of all residual solvents and any unreacted monomers. For the dose response curves, 6.25 to 100 ng were added (2.4 to 38.4 nM). Cells were incubated for 36 h at 37° C., 5% $CO_2$ and then firefly luciferase activity and viability was analyzed using "One Glo+Tox" assay kits (Promega). RNAiMax control experiments used OptiMEM during the initial mixing stage according to the manufacturer's recommended protocol. All polymeric NP experiments were performed in full 5% serum-containing DMEM. Results were normalized to untreated cells (n=4). To evaluate statistical significance, two-tailed T tests with the 95% confidence level were conducted. As an example, A7 was compared to RNAiMax: * * * *, p<0.0001.

4. In Vivo Factor VII Silencing in Mice

All procedures used in animal studies were approved by the Institutional Animal Care and Use Committee and were consistent with local, state and federal regulations as applicable. C57BL/6 mice (Harlan) were used for siRNA silencing experiments. 2'-F sugar modified siRNAs (Sigma-Aldrich) were used to prevent activation of the Toll-like receptor 7 immune response and confer enzymatic resistance. Nanoparticles were purified by dialysis into sterile PBS. Prior to injection, complexes were diluted in PBS at siRNA concentrations such that each mouse was administered a dose of 0.01 mL/g body-weight. Formulations were administered intravenously via tail vein injection. After 48 h, body-weight gain/loss was measured and mice were anaesthetized by isofluorane inhalation for blood sample collection by retro-orbital eye bleed. Serum was isolated with serum separation tubes (Becton Dickinson) and Factor VII protein levels were analyzed by chromogenic assay (Biophen FVII, Aniara Corporation). A standard curve was constructed using samples from PBS-injected mice and relative Factor VII expression was determined by comparing treated groups to an untreated PBS control.

5. Microscopy

Cellular uptake studies were performed using the top performing materials from the polymer screen. HeLa-Luc cells were seeded at a density of 30,000 cells per well in 8-chambered coverglass slides (Nunc) and allowed to attached for 24 hours. NP formulations were prepared by manual mixing using a similar protocol to the in vitro transfection assays above using Cy5.5-labeled siRNA. The formulation was performed in 10 mM citrate buffer pH 4.3 at a final mole ratio of 100:1 polymer:siRNA, and the lipid mixture of the formulation consisted of molar ratios 50:38: 10:2 lipocationic polymer: cholesterol: DSPC: PEG-lipid. The nanoparticles were added to the cells at a final siRNA dose of 100 ng/well. After 3 h incubation, the medium was aspirated, washed with PBS, and cell membrane staining was performed (Cell Mask Orange, Molecular Probes) using the manufacturer's protocol. Confocal microscopy imaging was performed using a Nikon Eclipse TE2000-E and images were analyzed using ImageJ (NIH).

6. In Vivo Biodistribution and Luciferase Silencing in Mice

Animals Female athymic Nude-Foxn1$^{nu}$ mice were purchased from Harlan Laboratories (Indianapolis, Ind.). All experiments were approved by the Institutional Animal Care and Use Committees of The University of Texas Southwestern Medical Center and were consistent with local, state and federal regulations as applicable.

In vivo biodistribution MDA-MB-231-Luc tumor cells ($5 \times 10^6$) in 100 μL PBS were injected subcutaneously into each flank of the mice. After three weeks when the tumors reached the adequate size, A1 NPs (A1:cholesterol:DSPC: PEG-lipid=50:35:10:5; polymer:siRNA=20:1 (weight); aqueous:EtOH=3:1 (volume)) containing 50 μg siLuc (50% Cy5.5-labeled) in 200 μL were injected intravenously (2.5 mg/kg dose IV). After 2.5 h, mice were anesthetized with 2.5% isofluorane in oxygen and the whole body and ex vivo organs fluorescence imaging was performed on an IVIS Lumina System (Caliper Life Sciences).

In vivo bioluminescence imaging MDA-MB-231-Luc tumor-bearing mice (see above) were anesthetized with 2.5% isofluorane in oxygen. D-Luciferin, monosodium salt (Fisher Scientific) was dissolved in PBS (40 mg/mL) and administered intraperitoneally at a dose of 200 mg/kg body weight. Bioluminescence imaging was performed 10 min after luciferin administration on the IVIS Lumina System (Caliper Life Sciences). Mice were then injected intratumorally with the A1 NPs (A1:cholesterol:DSPC:PEG-lipid=50: 35:10:5; polymer:siRNA=20:1 (weight); aqueous: EtOH=3:1 (volume)) NPs with the siRNA concentration of 50 μg/100 μL (siLuc or control siGFP) in a total volume of 150 μL per mouse distributed between the two tumors on both flanks. Twenty-four hours after NP administration, luminescence imaging was performed again as described above. The BLI signal intensities from the tumors were quantified by the fixed regions of interest (ROI) as the total flux of photons per second and normalized against the initial values obtained prior to the first injection.

Figure 10A:
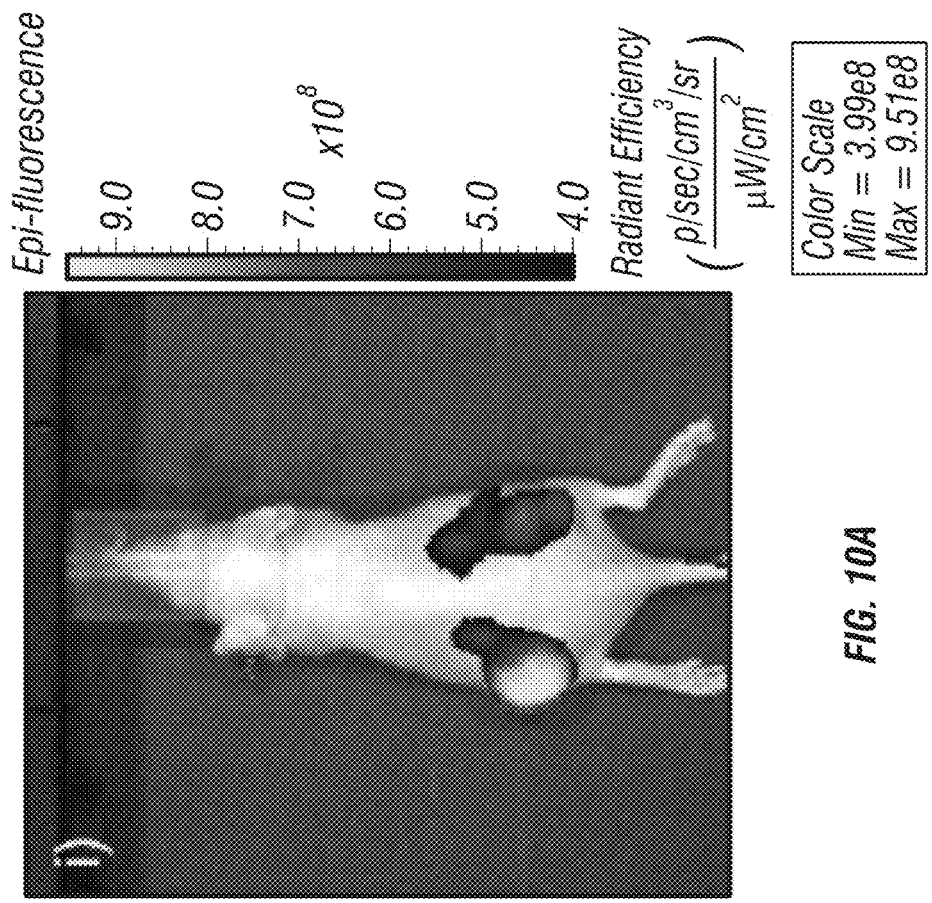
FIGS. 10A-10C show (FIG. 10A) A1 NPs provided effective accumulation in tumor xenografts after IV injection. A representative mouse is shown from three angles. Luciferase silencing was measured in tumors 24 hours after injection by (FIG. 10B) bioluminescence imaging or (FIG. 10C) in tissue lysates normalized against total protein level or total tissue amount (n=4; * $P<0.05$).
Figure 10A:
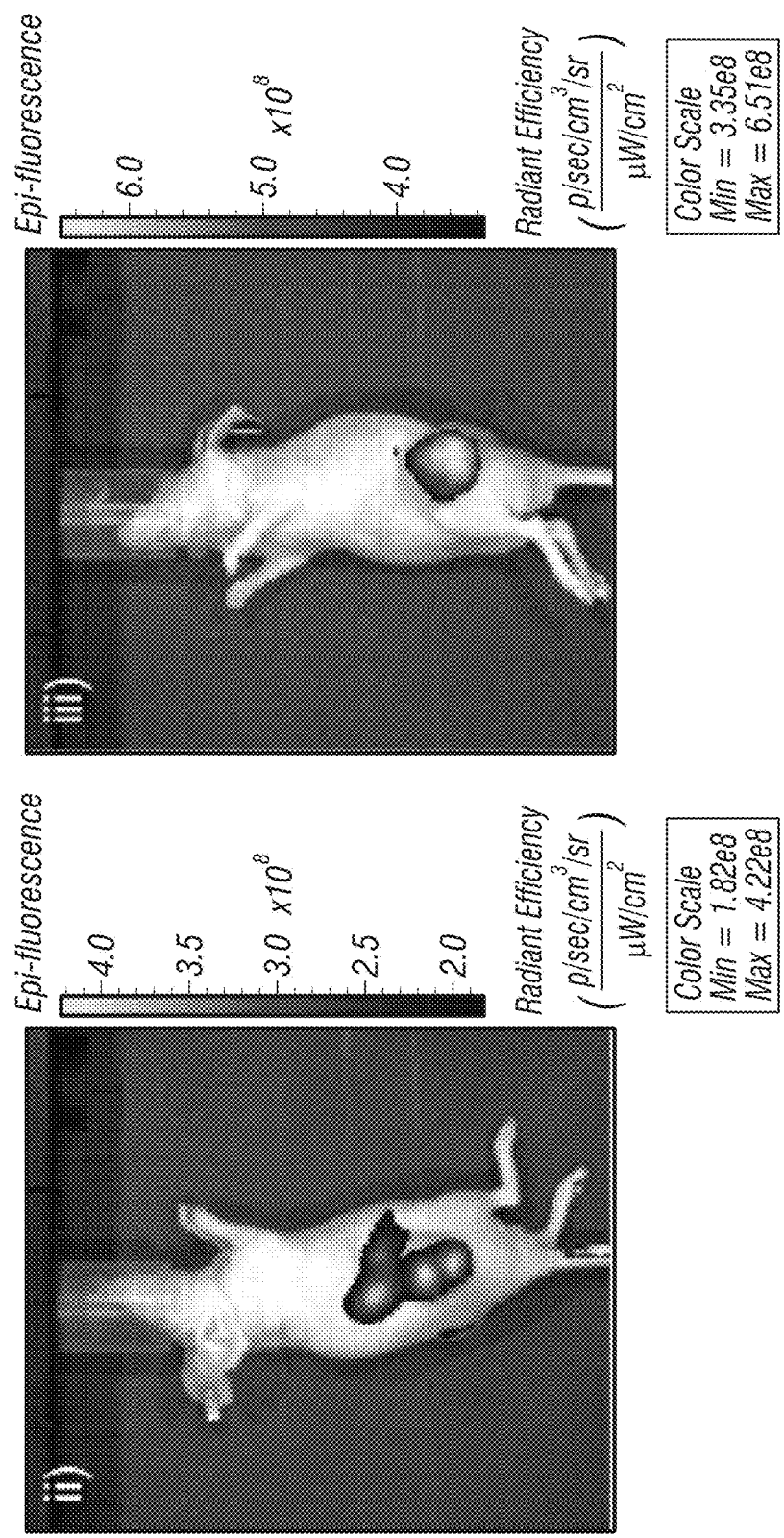
Figure 10B:
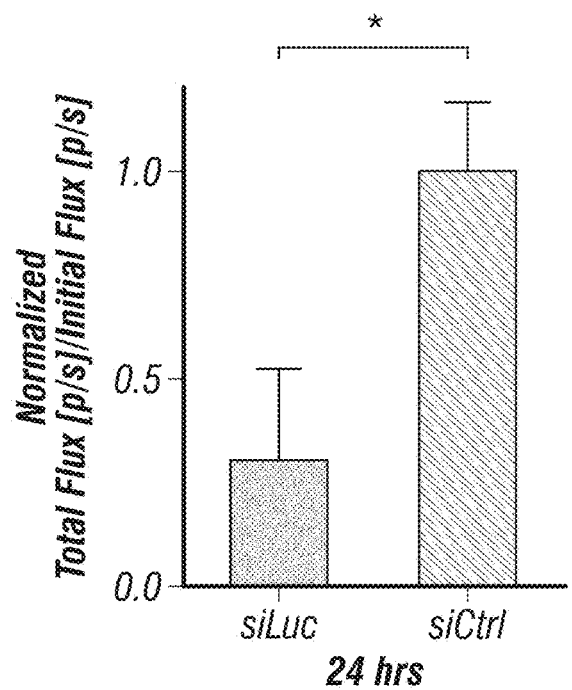
Figure 10C:
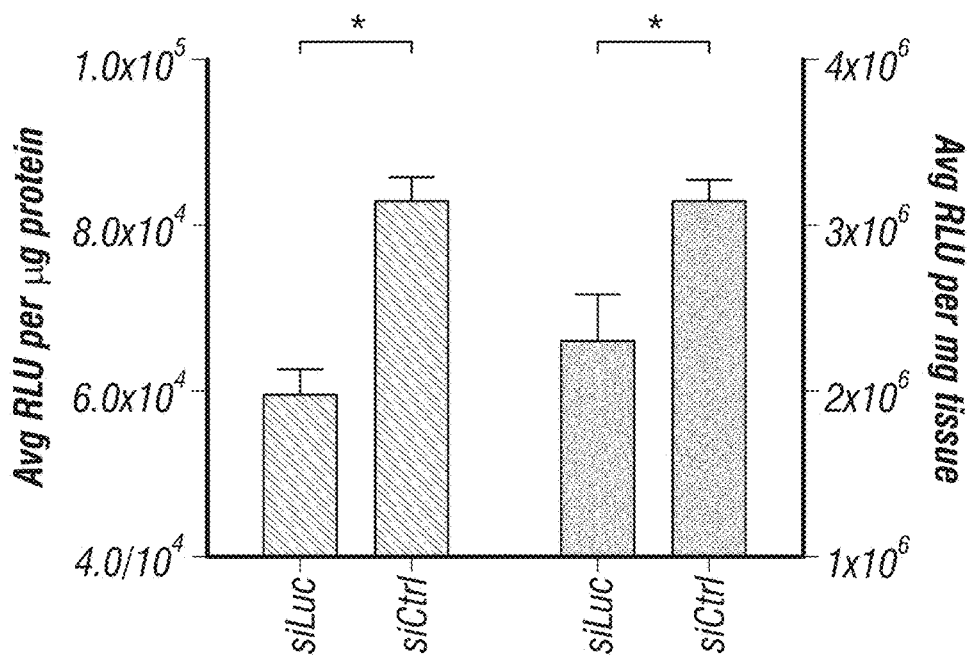

Quantitative luciferase and total protein measurements MDA-MB-231-Luc tumor-bearing mice were administered A1 NPs intratumorally at the concentrations described above for the bioluminescence imaging. On the following day, the NPs were injected again. Two days after second injection, mice were sacrificed and tumor tissues collected, weighed and homogenized in RLB buffer (Promega) using T 25 digital ULTRA-TURRAX (Ika). Tumor homogenates were centrifuged and the supernatant applied in protein concentration and luciferase activity measurements. Luciferase assay reagent (Promega) was added to the supernatant (20 μL) and the luminescence was detected using Infinite 200 PRO micro plate reader (Tecan). Background signals were subtracted. The protein concentrations were determined using the BCA Protein Assay Kit (Pierce) according to the manufacturer's protocol. The luminescence data were calculated as relative light units per milligram of tissue or microgram of proteins. To evaluate statistical significance, student's T tests with the 95% confidence level were conducted. * p<0.1. FIG. 10B: n=4; p=0.0121. FIG. 10C left: n=4; p=0.0300 FIG. 10C right: n=4; p=0.0386.

siRNA retention in tumor The MDA-MB-231-Luc tumor-bearing mice were injected intratumorally with the A1 NPs (A1:cholesterol:DSPC:PEG-lipid=50:35:10:5; polymer: siRNA=20:1 (weight); aqueous:EtOH=3:1 (volume)) NPs with the siRNA concentration of 50 μg/100 μL (siLuc; 20%

Cy5.5-siLuc) in a total volume of 150 μL per mouse distributed between the tumors on both flanks. Two days later, whole body fluorescence imaging was performed on an IVIS Lumina System (Caliper Life Sciences).

Example 2: Synthesis of Polymers and Monomer Components

1. Aminothiol Synthesis

Scheme 1: Synthesis of thiol containing amines

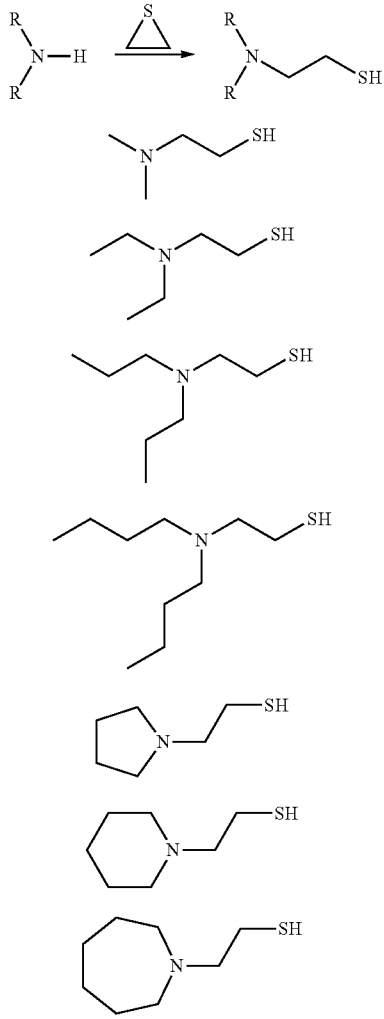

General Procedure for Synthesis of Aminothiols.

For 2-(dimethylamino)ethane-1-thiol (1):

A 250 mL round bottom flask was dried overnight, degassed, and refilled with nitrogen prior to being placed in a liquid nitrogen bath. Then, dimethylamine was released into the flask where it solidified into a white solid. The liquid nitrogen bath was removed, and the solid dimethylamine was weighed to be 10.5 g (0.23 mol). 50 mL dry dichloromethane (DCM) was added and the flask was placed in an ice bath. 18 g ethylene sulfide (0.30 mol) was dissolved in 25 mL dry DCM and added into the flask drop wise. The reaction solution was stirred for 2 hours from 0° C. to room temperature under nitrogen. The solution was concentrated via rotary evaporation at 40° C. Sodium ascorbate was added and filtered to yield 15.6 g (0.15 mol) product (yield: 65%) as a colorless liquid. The structure was verified by NMR and LC-MS.

For 2-(diethylamino)ethane-1-thiol (2), 2-(dipropylamino)ethane-1-thiol (3), 2-(dibutylamino)ethane-1-thiol (4), 2-(pyrrolidin-1-yl)ethane-1-thiol (5), 2-(piperidine-1-yl) ethane-1-thiol (6), and 2-(azepan-1-yl)ethane-1-thiol (7):

The secondary amine (0.1 mol) was dissolved in 100 mL DCM in a pre-dried flask, followed by addition of 12 g ethylene sulfide (0.2 mol) in 50 mL DCM solution. The reaction solution was stirred at room temperature for 2 hours under nitrogen, and then concentrated via rotary evaporation and distilled under vacuum to yield a colorless liquid. The yields (based on secondary amine) for compounds (2-7) were 42%, 40%, 22%, 47%, 54%, 35%, respectively. The structures were verified by NMR and LC-MS.

2-(dimethylamino)ethane-1-thiol (1) $^1$H NMR (500 MHz, CDCl$_3$): δ 2.61 (t, 2H), 2.48 (t, 2H), 2.24 (s, 6H)

2-(diethylamino)ethane-1-thiol (2) $^1$H NMR (500 MHz, CDCl$_3$): δ 2.61 (m, 2H), 2.59 (m, 2H), 2.52 (q, 4H), 1.02 (t, 6H) m/z=133.1

2-(dipropylamino)ethane-1-thiol (3) $^1$H NMR (500 MHz, CDCl$_3$): δ 2.62 (m, 2H), 2.56 (m, 2H), 2.36 (m, 4H), 1.45 (m, 4H), 0.88 (t, 6H). m/z=161.2

2-(dibutylamino)ethane-1-thiol (4) $^1$H NMR (500 MHz, CDCl$_3$): δ 2.60 (m, 2H), 2.58 (m, 2H), 2.41 (t, 4H), 1.41 (m, 4H), 1.31 (m, 4H), 0.91 (t, 6H). m/z=189.2

2-(pyrrolidin-1-yl)ethane-1-thiol (5) $^1$H NMR (500 MHz, CDCl$_3$): δ 2.65 (br, 4H), 2.51 (br, 4H), 1.78 (m, 4H). m/z=131.2

2-(piperidin-1-yl)ethane-1-thiol (6) $^1$H NMR (500 MHz, CDCl$_3$): δ 2.62 (m, 2H), 2.50 (m, 2H), 2.38 (br, 4H), 1.57 (m, 4H), 1.42 (m, 2H). m/z=145.2

2-(azepan-1-yl)ethane-1-thiol (7) $^1$H NMR (500 MHz, CDCl$_3$): δ 2.69 (t, 2H), 2.63 (t, 4H), 2.59 (t, 2H), 1.63 (br, 4H), 1.58 (br. 4H). m/z=159.1

2. Monomer Synthesis

Scheme 2. Synthesis of monomers M1-M13

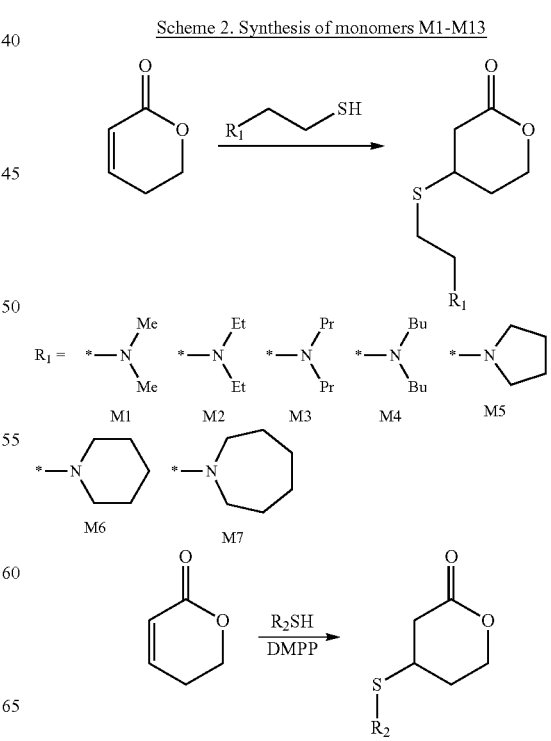

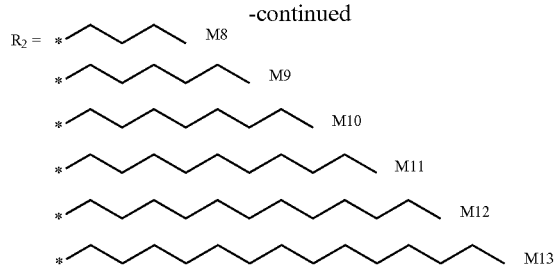

General procedure for synthesis of monomer M1-M7. 5,6-dihydro-2H-pyran-2-one (DPO) reacted with an aminothiol (1-7) at a mole ratio of 1 to 1, and the reaction was stirred at 50° C. for two hours. Complete reactant conversion to product was reached with ~100% yield. The structures were verified by NMR and LC-MS 4-((2-(dimethylamino)ethyl)thio)tetrahydro-2H-pyran-2-one (M1 or N1) $^1$H NMR (500 MHz, CDCl$_3$): δ 4.45 (ddd, 1H), 4.22 (ddd, 1H), 3.20 (m, 1H), 2.88 (ddd, 1H), 2.62 (t, 2H), 2.47 (m, 3H), 2.19 (s, 6H), 2.16 (m, 1H), 1.81 (ddd, 1H). $^{13}$C NMR (500 MHz, CDCl$_3$) δ 169.25, 67.25, 58.95, 45.27, 37.14, 35.92, 29.49, 28.58 [MH]$^+$ m/z=204.1

4-((2-(diethylamino)ethyl)thio)tetrahydro-2H-pyran-2-one (M2 or N2) $^1$H NMR (500 MHz, CDCl$_3$): δ 4.48 (ddd, 1H), 4.25 (ddd, 1H), 3.24 (m, 1H), 2.92 (ddd, 1H), 2.63 (br. 4H), 2.51 (m, 5H), 2.18 (ddd, 1H), 1.85 (ddd, 1H), 0.99 (t, 6H). $^{13}$C NMR (500 MHz, CDCl$_3$) δ 169.28, 67.27, 52.77, 46.92, 37.21, 36.02, 29.58, 28.50, 11.71 [MH]$^+$ m/z=232.2

4-((2-(dipropylamino)ethyl)thio)tetrahydro-2H-pyran-2-one (M3 or N3) $^1$H NMR (500 MHz, CDCl$_3$): δ 4.49 (ddd, 1H), 4.26 (ddd, 1H), 3.25 (m, 1H), 2.92 (ddd, 1H), 2.63 (br, 4H), 2.49 (dd, 1H), 2.36 (m, 4H), 2.17 (ddd, 1H), 1.83 (ddd, 1H), 1.43 (m, 4H), 0.85 (t, 6H). $^{13}$C NMR (500 MHz, CDCl$_3$) δ 169.27, 67.25, 56.15, 54.10, 37.29, 35.99, 29.61, 28.64, 20.30, 11.87. [MH]$^+$ m/z=260.2

4-((2-(dibutylamino)ethyl)thio)tetrahydro-2H-pyran-2-one (M4 or N4) $^1$H NMR (500 MHz, CDCl$_3$): δ 4.50 (ddd, 1H), 4.26 (ddd, 1H), 3.25 (m, 1H), 2.93 (dd, 1H), 2.63 (br, 4H), 2.50 (dd, 1H), 2.40 (t, 4H), 2.19 (m, 1H), 1.82 (m, 1H), 1.38 (m, 4H), 1.28 (m, 4H), 0.89 (t, 6H). $^{13}$C NMR (500 MHz, CDCl$_3$): δ 169.26, 67.24, 54.04, 53.96, 37.25, 36.01, 29.62, 29.27, 28.63, 20.62, 14.07. [ME]$^+$ m/z=288.2

4-((2-(pyrrolidin-1-yl)ethyl)thio)tetrahydro-2H-pyran-2-one (M5 or N5) $^1$H NMR (500 MHz, CDCl$_3$): δ 4.46 (ddd, 1H), 4.23 (ddd, 1H), 3.21 (m, 1H), 2.90 (ddd, 1H), 2.66 (m, 4H), 2.48 (m, 5H), 2.18 (ddd, 1H), 1.84 (ddd, 1H), 1.74 (m, 4H). $^{13}$C NMR (500 MHz, CDCl$_3$): δ 169.21, 67.23, 56.10, 54.05, 37.17, 36.03, 29.63, 29.55, 23.40. [MH]$^+$ m/z=230.1

4-((2-(piperidin-1-yl)ethyl)thio)tetrahydro-2H-pyran-2-one (M6 or N6) $^1$H NMR (500 MHz, CDCl$_3$): δ 4.48 (ddd, 1H), 4.24 (ddd, 1H), 3.24 (m, 1H), 2.91 (ddd, 1H), 2.64 (m, 2H), 2.51 (m, 3H), 2.36 (br, 4H), 2.19 (ddd, 1H), 1.84 (ddd, 1H), 1.54 (m, 4H), 1.40 (m, 2H). $^{13}$C NMR (500 MHz, CDCl$_3$): δ 169.24, 67.25, 59.13, 54.50, 37.21, 36.04, 29.60, 27.90, 25.85, 24.22. [MH]$^+$ m/z=244.1

4-((2-(azepan-1-yl)ethyl)thio)tetrahydro-2H-pyran-2-one (M7 or N7) $^1$H NMR (500 MHz, CDCl$_3$): δ 4.46 (ddd, 1H), 4.24 (ddd, 1H), 3.23 (m, 1H), 2.91 (dd, 1H), 2.63 (m, 2H), 2.50 (dd, 1H), 2.20 (ddd, 1H), 1.84 (ddd, 1H), 1.54 (m, 8H). $^{13}$C NMR (500 MHz, CDCl$_3$): δ 169.28, 67.26, 57.77, 55.29, 37.26, 35.97, 29.62, 28.69, 28.03, 26.97. [ME]$^+$ m/z=258.1

General procedure for synthesis of alkylthiol monomers. 5,6-dihydro-2H-pyran-2-one (DPO) was reacted with an alkylthiol at a mole ratio of 1 to 1.2. Dimethylphenylphosphine (DMPP) (0.5% by mol) was added to the reaction mixture, and the reaction was stirred at room temperature until all the DPO was converted (100%). The reaction mixture was then separated by flash chromatography (with hexane: ethyl acetate=10:09:1) to obtain pure monomers. The structures were verified by NMR and LC-MS.

4-(butylthio)tetrahydro-2H-pyran-2-one (M8 or C4) $^1$H NMR (500 MHz, CDCl$_3$): δ 4.52 (ddd, 1H), 4.29 (ddd, 1H), 3.19 (m, 1H), 2.93 (ddd, 1H), 2.57 (m, 3H), 2.20 (ddd, 1H) 1.85 (ddd, 1H), 1.57 (m, 2H), 1.42 (m, 2H), 0.92 (t, 3H); $^{13}$C NMR (500 MHz, CDCl$_3$) δ 169.42, 67.34, 37.19, 35.73, 31.57, 30.27, 29.49, 22.00, 13.65; [ME]$^+$ m/z=189.1

4-(hexylthio)tetrahydro-2H-pyran-2-one (M9 or C6) $^1$H NMR (500 MHz, CDCl$_3$): δ 4.48 (ddd, 1H), 4.25 (ddd, 1H), 3.17 (m, 1H), 2.90 (ddd, 1H), 2.54 (m, 3H), 2.17 (ddd, 1H), 1.84 (ddd, 1H), 1.54 (m, 2H), 1.36 (m, 2H), 1.25 (m, 4H), 0.85 (t, 3H). $^{13}$C NMR (500 MHz, CDCl$_3$) δ 169.36, 67.30, 37.18, 35.74, 31.33, 30.59, 29.48, 28.54, 22.49, 14.01. [MH]$^+$ m/z=217.2

4-(octylthio)tetrahydro-2H-pyran-2-one (M10 or C8) $^1$H NMR (500 MHz, CDCl$_3$): δ 4.51 (ddd, 1H), 4.28 (ddd, 1H), 3.19 (m, 1H), 2.92 (ddd, 1H), 2.55 (m, 3H), 2.19 (ddd, 1H), 1.87 (ddd, 1H), 1.57 (m, 2H), 1.26 (m, 10H), 0.85 (t, 3H). $^{13}$C NMR δ 169.40, 67.33, 37.20, 35.75, 31.78, 30.61, 29.53, 29.51, 29.15, 29.14, 28.91, 22.64, 14.11; [MH]$^+$ m/z=245.2

4-(decylthio)tetrahydro-2H-pyran-2-one (M11 or C10) $^1$H NMR (500 MHz, CDCl$_3$): δ 4.52 (ddd, 1H), 4.29 (ddd, 1H), 3.19 (m, 1H), 2.93 (ddd, 1H), 2.56 (m, 3H), 2.18 (ddd, 1H), 1.87 (ddd, 1H), 1.57 (m, 2H), 1.24 (m, 14H), 0.86 (t, 3H); $^{13}$C NMR δ 169.38, 67.32, 37.20, 35.76, 31.90, 30.61, 29.53, 29.51, 29.48, 29.29, 29.18, 28.90, 22.67, 14.13; [MH]$^+$ m/z=273.3

4-(dodecylthio)tetrahydro-2H-pyran-2-one (M12 or C12) $^1$H NMR (500 MHz, CDCl$_3$): δ 4.50 (ddd, 1H), 4.27 (ddd, 1H), 3.20 (m, 1H), 2.92 (ddd, 1H), 2.54 (m, 3H), 2.18 (ddd, 1H), 1.87 (ddd, 1H), 1.57 (m, 2H), 1.24 (m, 18H), 0.86 (t, 3H); $^{13}$C NMR δ 169.38, 67.32, 37.20, 35.75, 31.91, 30.61, 29.64, 29.62, 29.58, 29.54, 29.51, 29.49, 29.35, 29.19, 28.91, 22.69, 14.14; [MH]$^+$ m/z=301.4

4-(tetradecylthio)tetrahydro-2H-pyran-2-one (M13 or C14) $^1$H NMR (500 MHz, CDCl$_3$): δ 4.51 (ddd, 1H), 4.29 (ddd, 1H), 3.20 (m, 1H), 2.95 (ddd, 1H), 2.56 (m, 3H), 2.21 (ddd, 1H), 1.88 (ddd, 1H), 1.60 (m, 4H), 1.37 (m, 2H), 1.25 (m, 18H), 0.88 (t, 3H). $^{13}$C NMR 169.35, 67.31, 37.20, 35.76, 31.92, 30.62, 29.68, 29.66, 29.65, 29.64, 29.58, 29.54, 29.52, 29.49, 29.36, 29.18, 28.91, 22.69, 14.13. [MH]$^+$ m/z=329.3

3. Polymer Synthesis

A unique synthetic strategy to rapidly build a library of lipocationic polyesters via anionic ring-opening polymerization was developed. Previous reports highlight the importance of the inclusion of tertiary amines and alkyl chains for effective siRNA delivery (Akincw et al., 2008, Love et al., 2010, Siegwart et al., 2011, Jayaraman et al., 2012, Scholz and Wagner, 2012 and Nelson et al., 2013). However, the synthesis of amine-containing cyclic esters (and polyesters) is not straightforward because amine as nucleophile can hydrolyze esters. The synthesis of functional valerolactones using thiol-Michael addition to commercially available 5,6-dihydro-2H-pyran-2-one (DPO) was described by Kim, et al. (Kim et al., 2012). Unfortunately, the Michael addition of secondary amines to DPO was successful, but the resulting functionalized valerolactones could not be polymerized as the monomers underwent retro-Michael addition upon heating. Thus, a synthetic strategy utilizing thiols was employed to introduce an amine group, such as a tertiary amine. Seven tertiary amine containing aminothiols followed by reacting these aminothiols with DPO at a 1:1 ratio to give the appropriate tertiary amine functionalized valerolactone monomers. Six alkylated valerolactone monomers were also synthesized via a similar strategy and were purified through column chromatography. Utilizing these methods, monomers were synthesized through a single step, which enabled functional monomer/polymer synthesis in gram scale. While some monomers were purification, the high reaction conversion enabled the polymerization to be conducted in one pot from monomer synthesis to polymer synthesis without additional workup or purification leading to increased yield and efficiency. To explore structure-function activity, random copolymers from all monomers were synthesized through anionic ring-opening polymerization using methyl lithium as the initiator. By using methyl lithium, the prepared polymers did not contain any initiator chain end functionality, so that structure-function could be better correlated with the polymer composition. Without being bound by any theory, the mechanism of this reaction is believed to involve the nucleophilic attack of carbonyl carbon on the monomer by methyl anion in the initiator which results in scission of acyl-oxygen bond and the polymerization propagates via alcoholate ion. Polymerization with some conventional ROP catalysts including tin (II) octanoate and other anionic catalysts like alkoxides and organocatalysts (Kim et al., 2012, Tempelaar et al., 2011 and Silvers et al., 2012) were not successful produce the desired polymer. However, Grignard reagents were able to initiate all of the functional valerolactones reported herein to prepare a polymer with functional groups at the chain ends. Homo- and random (co)polymerizations were carried out in bulk in a glovebox and were usually completed within 2 minutes with high conversion (85%-95%). Because of the high conversion rate was achieved, the polymers could be screened for siRNA delivery directly without further purification. Most of the synthesized polymers exhibit similar molecular weight to theoretical molecular weight based on DMF GPC and $^1$H NMR measurements. However, due to limited solubility of polymers with long alkylthiol chains, molecular weight of some of the polymers (marked with "*" in Table 1) were measured in THF GPC. The library consists of different combinations of the two monomer types at three different mole ratios for each combination of the monomers (3:1, 2:2, 1:3). The actual incorporation ratio was similar to the feed ratio which indicates the two types of monomers have similar reactivity under the given initiating condition. Using the approach described herein, both monomer and polymer synthesis are fast and easy, which allowed the rapid construction of a library of 139 functional polyesters.

Figure 2:
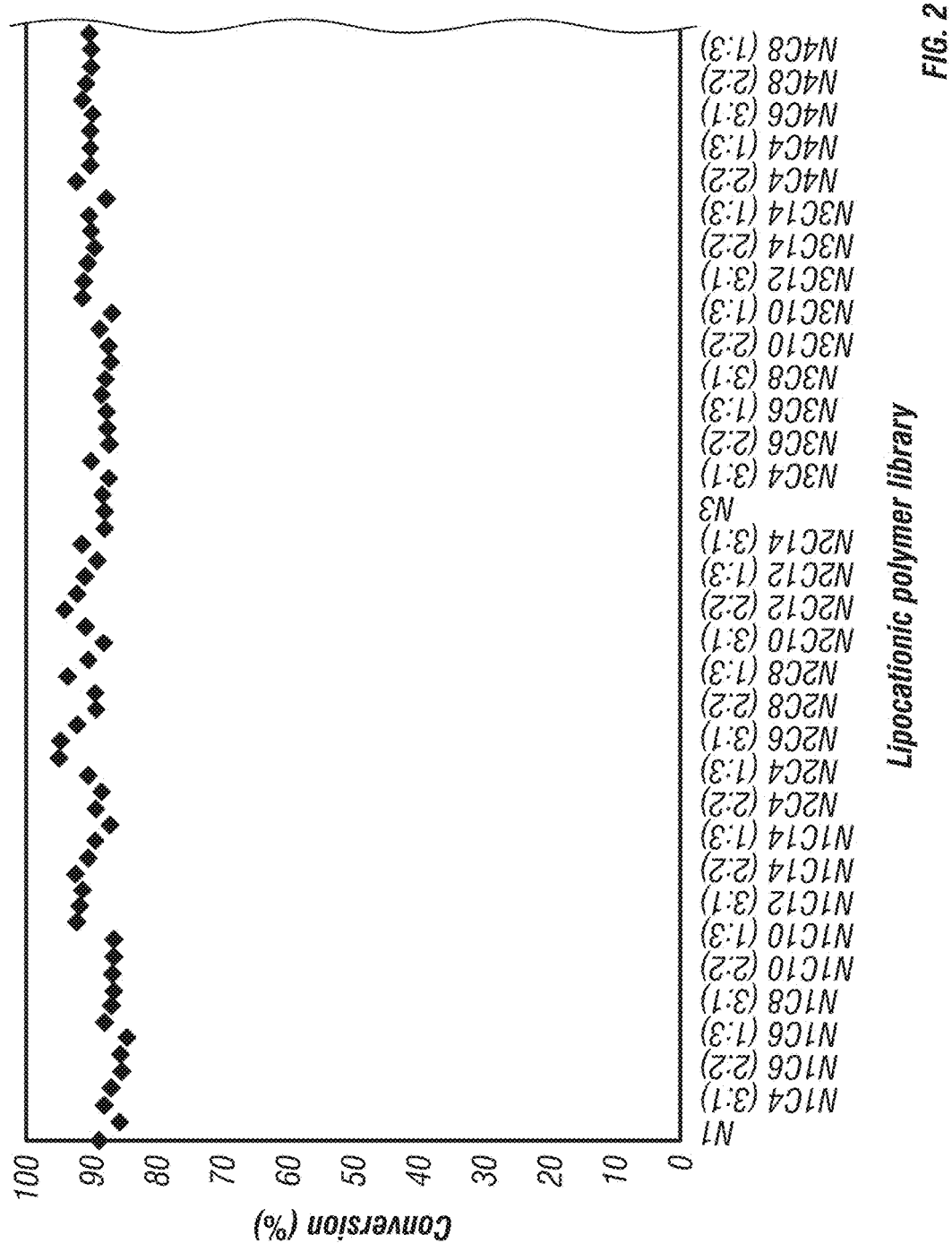
FIG. 2 shows the conversion percentage of the polymerization reaction for each monomer compositions.
Figure 2:
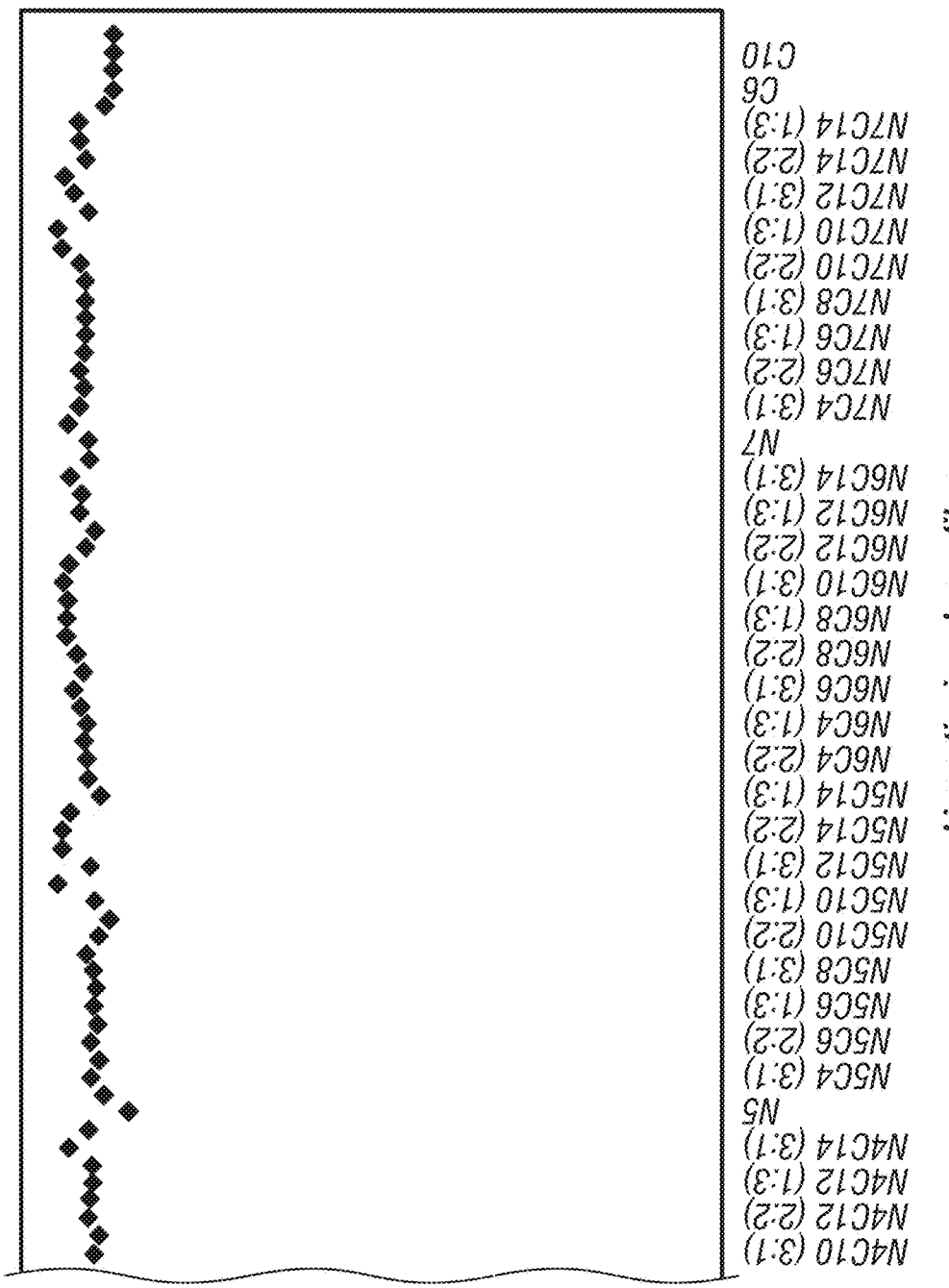
Figure 3:
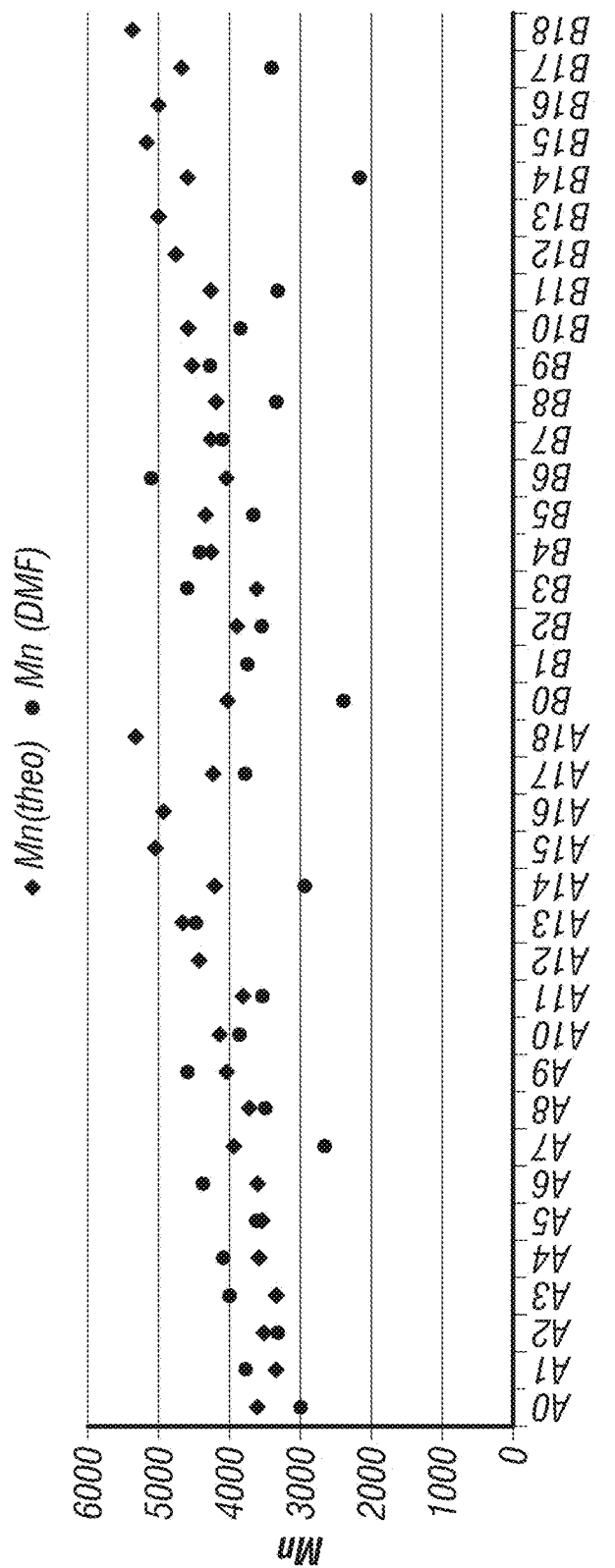
FIG. 3 shows the average molecular weight of the polymer for the composition containing the dimethylamino and diethylamino functional groups.

General procedure for synthesis of polymers: Glass vials with stir bars were dried in the oven for two days and were cooled under vacuum. All the vials were transferred into the glovebox. Two different monomers were added to each vial at a fixed mole ratio. Methyl lithium (5%) was then added into the reaction vial to start the reaction. The polymer synthetic pathway is shown below in Scheme 3 and the components and ratios are shown in FIG. 1. Conversion and average molecular weight (Mn) are shown in Table 1 and FIGS. 2 and 3.

A1, A7 and A9 are described as typical polymerizations.

A1: Synthesis of poly{4-((2-(dimethylamino)ethyl)thio) tetrahydro-2H-pyran-2-one}-r-poly{4-(butylthio)tetrahydro-2H-pyran-2-one}. Glass vials with stir bars were dried in an oven for two days and then cooled under vacuum. All of the vials were transferred into the glove box. Monomers N1 (0.104 g, 5.10×10$^{-4}$ mol) and C4 (0.096 g, 5.10× 10$^{-4}$ mol) were added to each vial at a fixed mole ratio listed below. 32 μL Methyl lithium (1.6 M in ether) was then added into the reaction vial to initiate the reaction. The polymer was collected after 5 minutes. Purified polymer was obtained by dialysis against THF for 4 hours. The polymer was then concentrated and dried via vacuum pump for 24 hours. The polymer was characterized by NMR and GPC (Table 1). $^1$H NMR (500 MHz, CDCl$_3$): δ 4.27 (br, 4H), 3.12 (br, 2H), 2.61 (m, 6H), 2.52 (m, 4H), 2.24 (s, 6H), 1.98 (br, 2H), 1.84 (br, 2H), 1.55 (m, 2H), 1.28 (m, 2H), 0.88 (t, 3H).

A7: Synthesis of poly{4-((2-(dimethylamino)ethyl)thio) tetrahydro-2H-pyran-2-one}-r-poly{4-(octylthio)tetrahydro-2H-pyran-2-one}. Glass vials with stir bars were dried in an oven for two days and then cooled under vacuum. All of the vials were transferred into the glove box. Monomers N1 (0.104 g, 5.10×10$^{-4}$ mol) and C8 (0.125 g, 5.10× 10$^{-4}$ mol) were added to each vial at a fixed mole ratio listed shown below. 32 μL Methyl lithium (1.6 M in ether) was then added into the reaction vial to initiate the reaction. The polymer was collected after 5 minutes. Purified polymer was obtained by dialysis against THF for 4 hours. The polymer was then concentrated and dried via vacuum pump for 24 hours. The polymer was characterized by NMR and GPC (Table 1). $^1$H NMR (500 MHz, CDCl$_3$): δ 4.27 (br, 4H), 3.12 (br, 2H), 2.61 (m, 6H), 2.52 (m, 4H), 2.24 (s, 6H), 1.98 (br, 2H), 1.84 (br, 2H), 1.55 (m, 2H), 1.28 (m, 10H), 0.88 (t, 3H)

A9: Synthesis of poly{4-((2-(dimethylamino)ethyl)thio) tetrahydro-2H-pyran-2-one}-r-poly{4-(octylthio)tetrahydro-2H-pyran-2-one}. Glass vials with stir bars were dried in an oven for two days and then cooled under vacuum. All of the vials were transferred into the glove box. Monomers N1 (0.052 g, 2.55×10$^{-4}$ mol) and C8 (0.187 g, 7.65× 10$^{-4}$ mol) were added to each vial at a fixed mole ratio listed shown below. 32 μl Methyl lithium (1.6 M in ether) was then added into the reaction vial to initiate the reaction. The polymer was collected after 5 minutes. Purified polymer was obtained by dialysis against THF for 4 hours. The polymer was then concentrated and dried via vacuum pump for 24 hours. The polymer was characterized by NMR and GPC (Table 1). $^1$H NMR (500 MHz, CDCl$_3$): δ 4.27 (br, 4H), 3.12 (br, 2H), 2.61 (m, 6H), 2.52 (m, 4H), 2.24 (s, 6H), 1.98 (br, 2H), 1.84 (br, 2H), 1.55 (m, 2H), 1.28 (m, 10H), 0.88 (t, 3H)

All the other polymers were synthesized using an identical procedure with different monomers. The exact moles of monomers used for different copolymers were:

M1:M2 (2:2): 5.10×10$^{-4}$ mol: 5.10×10$^{-4}$ mol

M1:M2 (1:3): 2.55×10$^{-4}$ mol: 7.65×10$^{-4}$ mol

M1:M2 (3:1): 7.65×10$^{-4}$ mol: 2.55×10$^{-4}$ mol

GPC analysis of several of the polymers are shown in FIG. 19A (DMF) and FIG. 19B (THF).

Scheme 3: Polymeric Synthesis

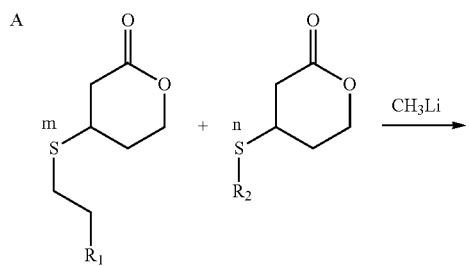

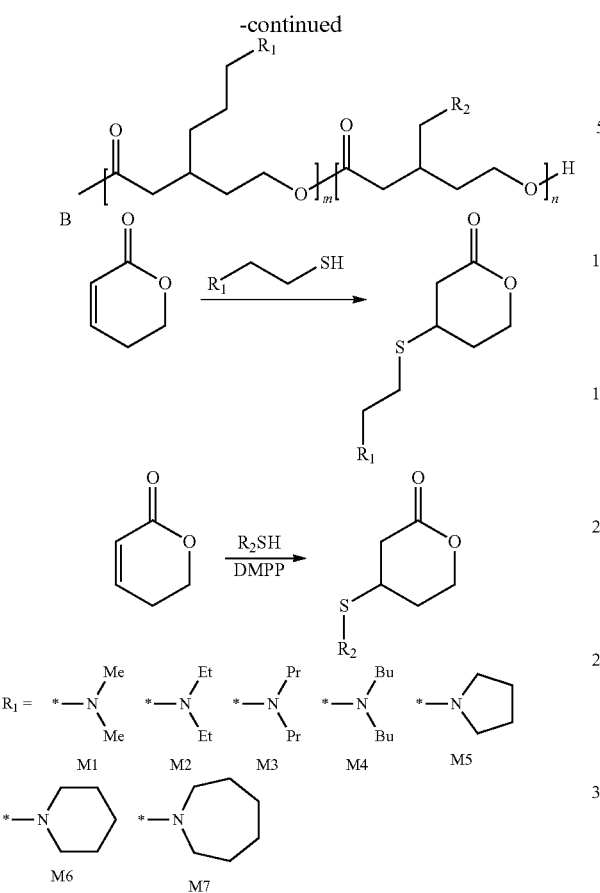

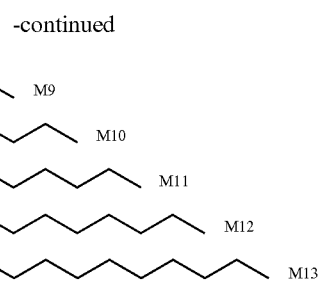

4. Gram Scale Synthesis

A gram scale reaction was carried out for copolymer A6 to examine scalability:

A6: Synthesis of poly{4-((2-(dimethylamino)ethyl)thio)tetrahydro-2H-pyran-2-one}-r-poly{4-(hexylthio)tetrahydro-2H-pyran-2-one}. Monomer N1 (0.25 g, $1.2\times10^{-3}$ mol) and Monomer C6 (0.8 g, $3.6\times10^{-3}$ mol) were added to a flame-dried glass vial. 153 μL Methyl lithium (1.6 M in ether) was then added into the reaction vial to initiate the polymerization. The polymer was collected after 5 minutes and dialyzed against THF for 4 hours. The polymer was then concentrated and dried via vacuum pump for 24 hours. Yield=87.7%. The polymer was characterized via NMR and GPC (FIG. 16). $^1$H NMR (500 MHz, CDCl$_3$): δ 4.27 (br, 4H), 3.12 (br, 2H), 2.61 (m, 6H), 2.52 (m, 4H), 2.24 (s, 6H), 1.98 (br, 2H), 1.84 (br, 2H), 1.55 (m, 2H), 1.28 (m, 6H), 0.88 (t, 3H).

TABLE 1

Polymer Characteristics

| Trial | Monomer 1 | Monomer 2 | M1:M2 | Conversion % | $M_n$ (theo) | $M_n$ (THF) | PDI (THF) | $M_n$ (DMF) | PDI (DMF) |
|---|---|---|---|---|---|---|---|---|---|
| A0 | 1N-SVL | NA | 4:0 | 89.02 | 3616 | | | 3018 | 2.01 |
| A1 | 1N-SVL | 4C-SVL | 2:2 | 85.88 | 3360 | 2340 | 1.65 | 3792 | 2.12 |
| A2 | 1N-SVL | 4C-SVL | 3:1 | 88.17 | 3515 | | | 3332 | 2.06 |
| A3 | 1N-SVL | 4C-SVL | 1:3 | 87.11 | 3342 | 4010 | 1.85 | 4036 | 2.18 |
| A4 | 1N-SVL | 6C-SVL | 2:2 | 85.58 | 3588 | 2687 | 1.62 | 4124 | 2.08 |
| A5 | 1N-SVL | 6C-SVL | 3:1 | 85.93 | 3546 | | | 3618 | 1.86 |
| A6 | 1N-SVL | 6C-SVL | 1:3 | 84.77 | 3609 | 3770 | 1.71 | 4388 | 2.19 |
| A7 | 1N-SVL | 8C-SVL | 2:2 | 88.31 | 3950 | 3315 | 1.80 | 2678 | 1.94 |
| A8 | 1N-SVL | 8C-SVL | 3:1 | 87.22 | 3722 | | | 3510 | 2.00 |
| A9 | 1N-SVL | 8C-SVL | 1:3 | 86.72 | 4057 | 5660 | 1.90 | 4597 | 2.25 |
| A10 | 1N-SVL | 10C-SVL | 2:2 | 87.2 | 4144 | 3760 | 1.70 | 3876 | 2.13 |
| A11 | 1N-SVL | 10C-SVL | 3:1 | 86.60 | 3817 | | | 3556 | 1.96 |
| A12 | 1N-SVL | 10C-SVL | 1:3 | 86.80 | 4425 | 6670 | 1.74 | | |
| A13 | 1N-SVL | 12C-SVL | 2:2 | 92.45 | 4653 | 5010 | 1.70 | 4460 | 2.17 |
| A14 | 1N-SVL | 12C-SVL | 3:1 | 92.12 | 4189 | | | 2922 | 1.88 |
| A15 | 1N-SVL | 12C-SVL | 1:3 | 91.42 | 5045 | 8990 | 1.77 | | |
| A16 | 1N-SVL | 14C-SVL | 2:2 | 92.63 | 4922 | 6164 | 1.59 | | |
| A17 | 1N-SVL | 14C-SVL | 3:1 | 90.55 | 4245 | | | 3777 | 1.32 |
| A18 | 1N-SVL | 14C-SVL | 1:3 | 89.56 | 5319 | 8430 | 1.61 | | |
| B0 | 2N-SVL | NA | 4:0 | 87.27 | 4038 | | | 2392 | 1.74 |
| B1 | 2N-SVL | 4C-SVL | 2:2 | 89.31 | 3746 | 3340 | 1.76 | 3743 | 2.31 |
| B2 | 2N-SVL | 4C-SVL | 3:1 | 88.53 | 3905 | 2258 | 1.78 | 3532 | 2.00 |
| B3 | 2N-SVL | 4C-SVL | 1:3 | 90.47 | 3599 | 5230 | 1.73 | 4590 | 2.04 |
| B4 | 2N-SVL | 6C-SVL | 2:2 | 95.23 | 4261 | 4525 | 1.67 | 4393 | 1.97 |
| B5 | 2N-SVL | 6C-SVL | 3:1 | 94.93 | 4320 | 2480 | 1.72 | 3649 | 2.03 |
| B6 | 2N-SVL | 6C-SVL | 1:3 | 92.21 | 4056 | 7020 | 1.70 | 5105 | 2.09 |
| B7 | 2N-SVL | 8C-SVL | 2:2 | 89.49 | 4255 | 4610 | 1.59 | 4086 | 2.09 |
| B8 | 2N-SVL | 8C-SVL | 3:1 | 89.40 | 4194 | 2571 | 1.70 | 3324 | 2.00 |
| B9 | 2N-SVL | 8C-SVL | 1:3 | 93.67 | 4514 | 7700 | 1.52 | 4276 | 1.99 |
| B10 | 2N-SVL | 10C-SVL | 2:2 | 90.59 | 4561 | 5720 | 1.54 | 3855 | 1.90 |
| B11 | 2N-SVL | 10C-SVL | 3:1 | 88.21 | 4262 | 2960 | 1.63 | 3300 | 1.87 |

TABLE 1-continued

Polymer Characteristics

| Trial | Monomer 1 | Monomer 2 | M1:M2 | Conversion % | $M_n$ (theo) | $M_n$ (THF) | PDI (THF) | $M_n$ (DMF) | PDI (DMF) |
|---|---|---|---|---|---|---|---|---|---|
| B12 | 2N-SVL | 10C-SVL | 1:3 | 90.94 | 4765 | 8250 | 1.55 | | |
| B13 | 2N-SVL | 12C-SVL | 2:2 | 94.11 | 5000 | 6750 | 1.56 | | |
| B14 | 2N-SVL | 12C-SVL | 3:1 | 92.21 | 4581 | 2536 | 1.52 | 2157 | 1.88 |
| B15 | 2N-SVL | 12C-SVL | 1:3 | 91.11 | 5156 | 10280 | 1.52 | | |
| B16 | 2N-SVL | 14C-SVL | 2:2 | 89.24 | 4992 | 7300 | 1.61 | | |
| B17 | 2N-SVL | 14C-SVL | 3:1 | 91.36 | 4667 | 4070 | 1.66 | 3395 | 2.11 |
| B18 | 2N-SVL | 14C-SVL | 1:3 | 87.87 | 5342 | 11220 | 1.71 | | |
| C0 | 3N-SVL | NA | 4:0 | 87.88 | 4559 | 4270 | 1.49 | 3006 | 1.69 |
| C1 | 3N-SVL | 4C-SVL | 2:2 | 88.42 | 3957 | 6680 | 1.55 | 4256 | 1.94 |
| C2 | 3N-SVL | 4C-SVL | 3:1 | 87.48 | 4227 | 5873 | 1.34 | 3938 | 1.82 |
| C3 | 3N-SVL | 4C-SVL | 1:3 | 90.08 | 3710 | 7600 | 1.57 | 4510 | 2.1 |
| C4 | 3N-SVL | 6C-SVL | 2:2 | 87.25 | 4149 | 7623 | 1.48 | 4504 | 1.86 |
| C5 | 3N-SVL | 6C-SVL | 3:1 | 87.5 | 4350 | 6860 | 1.45 | 4150 | 1.81 |
| C6 | 3N-SVL | 6C-SVL | 1:3 | 87.73 | 3982 | 8930 | 1.60 | 5030 | 2.13 |
| C7 | 3N-SVL | 8C-SVL | 2:2 | 88.43 | 4453 | 8160 | 1.48 | 4560 | 1.85 |
| C8 | 3N-SVL | 8C-SVL | 3:1 | 87.83 | 4490 | 7120 | 1.42 | 3910 | 1.80 |
| C9 | 3N-SVL | 8C-SVL | 1:3 | 87.13 | 4321 | 8900 | 1.55 | 4760 | 1.96 |
| C10 | 3N-SVL | 10C-SVL | 2:2 | 87.38 | 4645 | 8510 | 1.50 | 4260 | 1.90 |
| C11 | 3N-SVL | 10C-SVL | 3:1 | 88.62 | 4654 | 6480 | 1.50 | 3770 | 1.85 |
| C12 | 3N-SVL | 10C-SVL | 1:3 | 86.87 | 4673 | 10320 | 1.53 | | |
| C13 | 3N-SVL | 12C-SVL | 2:2 | 91.44 | 5115 | 10360 | 1.65 | | |
| C14 | 3N-SVL | 12C-SVL | 3:1 | 91.00 | 4903 | 8970 | 1.59 | 5320 | 1.99 |
| C15 | 3N-SVL | 12C-SVL | 1:3 | 90.34 | 5239 | 11660 | 1.53 | | |
| C16 | 3N-SVL | 14C-SVL | 2:2 | 89.28 | 5244 | 9540 | 1.66 | | |
| C17 | 3N-SVL | 14C-SVL | 3:1 | 89.85 | 4967 | 8120 | 1.64 | | |
| C18 | 3N-SVL | 14C-SVL | 1:3 | 90.33 | 5618 | 9120 | 1.71 | | |
| D0 | 4N-SVL | NA | 4:0 | 87.37 | 5023 | 3560 | 1.46 | 2410 | 1.55 |
| D1 | 4N-SVL | 4C-SVL | 2:2 | 92.08 | 4379 | 5980 | 1.62 | 3960 | 2.03 |
| D2 | 4N-SVL | 4C-SVL | 3:1 | 90.03 | 4729 | 5183 | 1.53 | 3521 | 1.71 |
| D3 | 4N-SVL | 4C-SVL | 1:3 | 90.23 | 3843 | 6580 | 1.63 | 4530 | 1.93 |
| D4 | 4N-SVL | 6C-SVL | 2:2 | 90.20 | 4542 | 6590 | 1.59 | 4160 | 1.90 |
| D5 | 4N-SVL | 6C-SVL | 3:1 | 89.67 | 4835 | 5720 | 1.62 | 3785 | 1.83 |
| D6 | 4N-SVL | 6C-SVL | 1:3 | 91.31 | 4272 | 8010 | 1.67 | 5030 | 1.48 |
| D7 | 4N-SVL | 8C-SVL | 2:2 | 90.58 | 4815 | 7070 | 1.54 | 4100 | 1.76 |
| D8 | 4N-SVL | 8C-SVL | 3:1 | 89.97 | 4978 | 5810 | 1.55 | 3480 | 1.71 |
| D9 | 4N-SVL | 8C-SVL | 1:3 | 89.78 | 4578 | 8800 | 1.55 | | |
| D10 | 4N-SVL | 10C-SVL | 2:2 | 90.07 | 5041 | 7870 | 1.56 | | |
| D11 | 4N-SVL | 10C-SVL | 3:1 | 89.50 | 5077 | 6270 | 1.59 | | |
| D12 | 4N-SVL | 10C-SVL | 1:3 | 88.67 | 4895 | 9030 | 1.69 | | |
| D13 | 4N-SVL | 12C-SVL | 2:2 | 90.16 | 5296 | 9110 | 1.75 | | |
| D14 | 4N-SVL | 12C-SVL | 3:1 | 90.03 | 5230 | 9630 | 1.54 | | |
| D15 | 4N-SVL | 12C-SVL | 1:3 | 89.63 | 5323 | 9260 | 1.87 | | |
| D16 | 4N-SVL | 14C-SVL | 2:2 | 89.76 | 5524 | 9770 | 1.74 | | |
| D17 | 4N-SVL | 14C-SVL | 3:1 | 92.98 | 5531 | 8270 | 1.68 | | |
| D18 | 4N-SVL | 14C-SVL | 1:3 | 90.17 | 5734 | 9880 | 1.82 | | |
| E0 | 5N-SVL | NA | 4:0 | 84.54 | 3878 | NA | | 2180 | 1.80 |
| E1 | 5N-SVL | 4C-SVL | 2:2 | 87.98 | 3673 | NA | | 3200 | 2.13 |
| E2 | 5N-SVL | 4C-SVL | 3:1 | 89.66 | 3928 | NA | | 2560 | 2.00 |
| E3 | 5N-SVL | 4C-SVL | 1:3 | 88.47 | 3511 | 3652 | 1.90 | 3900 | 2.13 |
| E4 | 5N-SVL | 6C-SVL | 2:2 | 89.88 | 4004 | NA | | 3364 | 2.13 |
| E5 | 5N-SVL | 6C-SVL | 3:1 | 88.99 | 4023 | NA | | 2460 | 2.07 |
| E6 | 5N-SVL | 6C-SVL | 1:3 | 89.62 | 3933 | 5880 | 1.71 | 4670 | 2.11 |
| E7 | 5N-SVL | 8C-SVL | 2:2 | 89.12 | 4220 | 2568 | 1.70 | 3330 | 2.02 |
| E8 | 5N-SVL | 8C-SVL | 3:1 | 89.34 | 4164 | NA | | 2310 | 1.94 |
| E9 | 5N-SVL | 8C-SVL | 1:3 | 90.17 | 4336 | 5750 | 1.65 | 3770 | 1.92 |
| E10 | 5N-SVL | 10C-SVL | 2:2 | 88.46 | 4436 | 3260 | 1.67 | 3770 | 1.91 |
| E11 | 5N-SVL | 10C-SVL | 3:1 | 87.22 | 4187 | NA | | 3380 | 2.11 |
| E12 | 5N-SVL | 10C-SVL | 1:3 | 89.21 | 4665 | 8700 | 1.58 | | |
| E13 | 5N-SVL | 12C-SVL | 2:2 | 94.41 | 4997 | 4190 | 1.61 | | |
| E14 | 5N-SVL | 12C-SVL | 3:1 | 89.80 | 4434 | NA | | 2390 | 1.96 |
| E15 | 5N-SVL | 12C-SVL | 1:3 | 94.03 | 5311 | 11650 | 1.55 | | |
| E16 | 5N-SVL | 14C-SVL | 2:2 | 93.84 | 5230 | 5268 | 1.65 | | |
| E17 | 5N-SVL | 14C-SVL | 3:1 | 92.70 | 4707 | NA | | 2500 | 2.02 |
| E18 | 5N-SVL | 14C-SVL | 1:3 | 88.37 | 5363 | 7010 | 1.67 | | |
| F0 | 6N-SVL | NA | 4:0 | 90.14 | 4387 | NA | | 2810 | 1.85 |
| F1 | 6N-SVL | 4C-SVL | 2:2 | 90.38 | 3900 | 4291 | 1.65 | 1400 | 1.45 |
| F2 | 6N-SVL | 4C-SVL | 3:1 | 90.68 | 4163 | 2740 | 1.71 | 3144 | 1.93 |
| F3 | 6N-SVL | 4C-SVL | 1:3 | 90.43 | 3652 | 5940 | 1.60 | 2564 | 1.82 |
| F4 | 6N-SVL | 6C-SVL | 2:2 | 91.14 | 4188 | 5400 | 1.59 | 3805 | 1.97 |
| F5 | 6N-SVL | 6C-SVL | 3:1 | 92.18 | 4361 | 3440 | 1.64 | 3376 | 1.93 |
| F6 | 6N-SVL | 6C-SVL | 1:3 | 90.85 | 4051 | 8180 | 1.51 | 2740 | 1.85 |
| F7 | 6N-SVL | 8C-SVL | 2:2 | 91.56 | 4464 | 6013 | 1.53 | 4410 | 2.02 |
| F8 | 6N-SVL | 8C-SVL | 3:1 | 93.35 | 4547 | 3765 | 1.69 | 3471 | 1.84 |
| F9 | 6N-SVL | 8C-SVL | 1:3 | 93.05 | 4540 | 8124 | 1.46 | 2860 | 1.84 |
| F10 | 6N-SVL | 10C-SVL | 2:2 | 92.93 | 4791 | 7326 | 1.49 | | |

TABLE 1-continued

Polymer Characteristics

| Trial | Monomer 1 | Monomer 2 | M1:M2 | Conversion % | $M_n$ (theo) | $M_n$ (THF) | PDI (THF) | $M_n$ (DMF) | PDI (DMF) |
|---|---|---|---|---|---|---|---|---|---|
| F11 | 6N-SVL | 10C-SVL | 3:1 | 93.53 | 4687 | 4100 | 1.64 | 4060 | 1.87 |
| F12 | 6N-SVL | 10C-SVL | 1:3 | 92.87 | 4922 | 9680 | 1.52 | | |
| F13 | 6N-SVL | 12C-SVL | 2:2 | 90.40 | 4912 | 8050 | 1.69 | | |
| F14 | 6N-SVL | 12C-SVL | 3:1 | 89.21 | 4593 | 4320 | 1.67 | 2820 | 1.81 |
| F15 | 6N-SVL | 12C-SVL | 1:3 | 91.21 | 5216 | 8880 | 1.69 | | |
| F16 | 6N-SVL | 14C-SVL | 2:2 | 91.00 | 5199 | 6480 | 1.75 | | |
| F17 | 6N-SVL | 14C-SVL | 3:1 | 92.60 | 4897 | 4800 | 1.40 | | |
| F18 | 6N-SVL | 14C-SVL | 1:3 | 89.77 | 5511 | 10897 | 1.70 | | |
| G0 | 7N-SVL | NA | 4:0 | 90.11 | 4639 | NA | | 2840 | 2.26 |
| G1 | 7N-SVL | 4C-SVL | 2:2 | 92.74 | 4131 | 2285 | 1.85 | 2250 | 1.73 |
| G2 | 7N-SVL | 4C-SVL | 3:1 | 91.41 | 4389 | 1614 | 1.91 | 3390 | 2.36 |
| G3 | 7N-SVL | 4C-SVL | 1:3 | 90.75 | 3728 | 5838 | 1.85 | 2610 | 2.14 |
| G4 | 7N-SVL | 6C-SVL | 2:2 | 91.15 | 4316 | 5520 | 1.71 | 4100 | 2.42 |
| G5 | 7N-SVL | 6C-SVL | 3:1 | 90.72 | 4483 | 2950 | 1.76 | 3630 | 2.25 |
| G6 | 7N-SVL | 6C-SVL | 1:3 | 90.39 | 4094 | 7853 | 1.75 | 2730 | 2.06 |
| G7 | 7N-SVL | 8C-SVL | 2:2 | 90.37 | 4532 | 5481 | 1.69 | 4610 | 2.41 |
| G8 | 7N-SVL | 8C-SVL | 3:1 | 90.18 | 4583 | 3170 | 1.71 | 3440 | 2.07 |
| G9 | 7N-SVL | 8C-SVL | 1:3 | 90.47 | 4478 | 8090 | 1.63 | 2540 | 1.92 |
| G10 | 7N-SVL | 10C-SVL | 2:2 | 90.91 | 4814 | 5950 | 1.79 | | |
| G11 | 7N-SVL | 10C-SVL | 3:1 | 93.59 | 4887 | 3930 | 1.77 | 4250 | 2.21 |
| G12 | 7N-SVL | 10C-SVL | 1:3 | 94.34 | 5066 | 8860 | 1.70 | | |
| G13 | 7N-SVL | 12C-SVL | 2:2 | 90.20 | 5027 | 6670 | 1.76 | | |
| G14 | 7N-SVL | 12C-SVL | 3:1 | 92.03 | 4931 | 4072 | 1.77 | | |
| G15 | 7N-SVL | 12C-SVL | 1:3 | 93.26 | 5399 | 8367 | 1.68 | | |
| G16 | 7N-SVL | 14C-SVL | 2:2 | 90.37 | 5290 | 7052 | 1.71 | | |
| G17 | 7N-SVL | 14C-SVL | 3:1 | 91.17 | 5013 | 3412 | 1.60 | | |
| G18 | 7N-SVL | 14C-SVL | 1:3 | 91.48 | 5680 | 8628 | 1.67 | | |
| C4* | NA | 4C-SVL | 0:4 | 87.60 | 3310 | | | 2360 | 1.74 |
| C6* | NA | 6C-SVL | 0:4 | 86.39 | 3732 | | | 2600 | 1.92 |
| C8* | NA | 8C-SVL | 0:4 | 86.3 | 4215 | | | 3350 | 1.69 |
| C10* | NA | 10C-SVL | 0:4 | 86.3 | 4696 | | | 2750 | 1.31 |
| C12* | NA | 12C-SVL | 0:4 | 86.4 | 5178 | | | 2860 | 1.53 |
| C14* | NA | 14C-SVL | 0:4 | 34.6 | 2247 | | | 1510 | 1.21 |

Example 3: Synthesis and Characterization of Polymers Nanoparticles

Figure 4A:
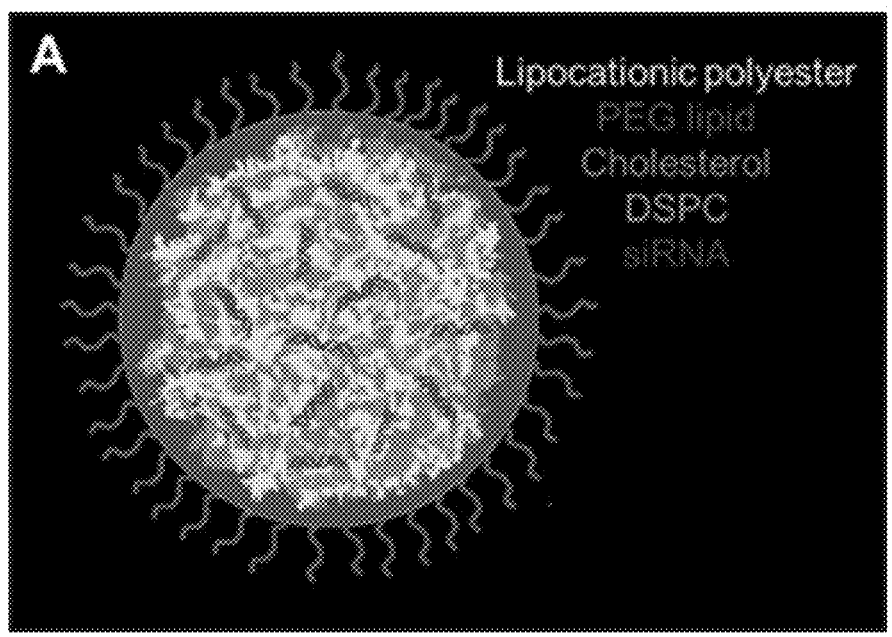
FIGS. 4A-4D show (FIG. 4A) Representative scheme of polymeric nanoparticle composition.
Figure 4B:
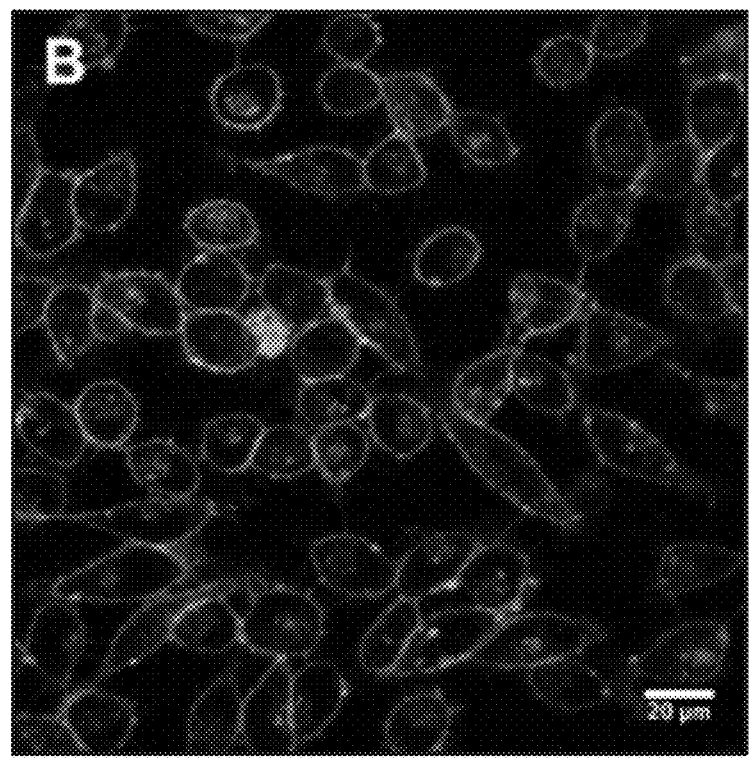
Figure 4C:
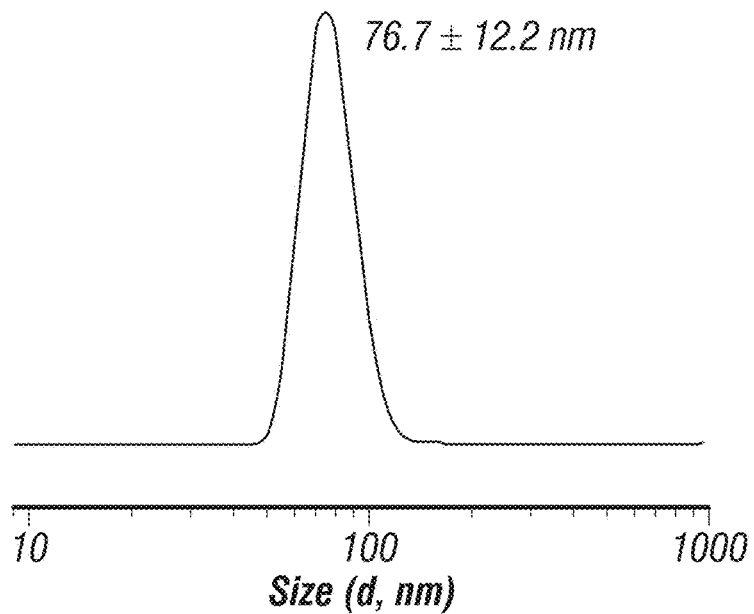
Figure 4D:
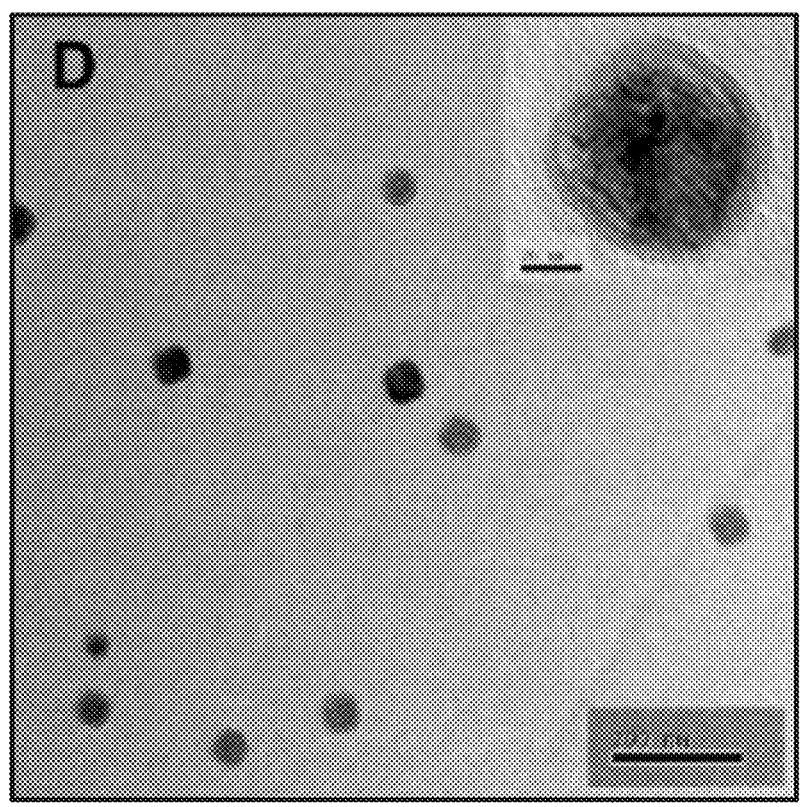
Figure 13:
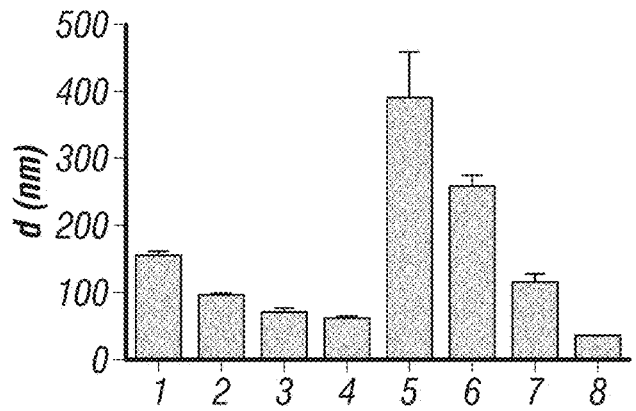
FIG. 13 shows the nanoparticle size can be controlled by mixing rations and conditions. DLS results for A7 NPs with different ratio of components (n=5) (mean±SEM). Within groups of fixed polymer:siRNA (wt) ratios, the size decreased when increasing the PEG-lipid amount. NPs were prepared using the NanoAssemblr. Ethanol solutions of polymers, DSPC, cholesterol, and PEG lipid were rapidly combined with acidic solutions of siRNA. The ratio of aqueous:EtOH was 3:1 (volume) and the flow rate was 12 mL/minute.
Figure 14:
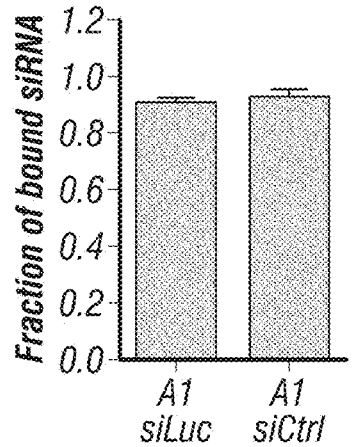
FIG. 14 shows the siRNA binding results for NPs used in in vivo experiments (siLuc and siControl). A1 NPs (A1.

To date, the most efficacious materials for siRNA delivery have been lipid nanoparticles composed of a cationic or ionizable lipid, DSPC, cholesterol, and lipid poly(ethylene glycol) (PEG) as shown in FIG. 4A. (Akincw et al., 2008, Love et al., 2010, Jayaraman et al., 2012, Coelho et al., 2013, Zimmermann et al., 2006 and Semple et al., 2010). These components reduce aggregation and provide enhanced nanoparticle stability at physiological conditions. With the formulation of polymer:DSPC:Cholesterol:PEG lipid=50:10:35:5 (by mole), the polymer nanoparticles had an average diameter of 100 nm as measured in PBS by dynamic light scattering. Nanoparticles with tunable size range from 35 nm to 300 nm could be prepared by adjusting the mixing conditions and the formulation components. The morphology of the most efficacious polymer was also studied using electron microscopy. An average diameter of 70 nm was observed, in agreement with DLS results. As can be seen in FIG. 4B, the nanoparticle exhibits spherical morphology on TEM. With this composition, for example, a less dense particle shell was observed which probably mainly consists of PEG lipid, while a more textured and electron dense core was observed which probably consists of polymer, siRNA and the other components in the formulation. The concentration of the therapeutic nucleic acid was varied as well as the relative proportions of the delivery components to determine its effect on the nanoparticle size. A graph of the effect on size of the compositions shown in Table 2 is shown in FIG. 13. Furthermore, these compositions were studied with different siRNA and showed similar binding of the siRNA (FIG. 14). Finally, repetitions of the same compositions show similar sizes as shown in FIG. 15.

TABLE 2

Composition Effects of Size of Nanoparticle

| Trial | Total Delivery Component:siRNA (wt) | A7:cholesterol:DSPC:PEG-lipid (mol) | d (nm) |
|---|---|---|---|
| 1 | 7:1 | 50:38.5:10:1.5 | 154 |
| 2 | 7:1 | 50:35:10:5 | 95 |
| 3 | 15:1 | 50:35:10:5 | 69 |
| 4 | 20:1 | 50:35:10:5 | 62 |
| 5 | 20:1 | 70:15:10:5 | 387 |
| 6 | 25:1 | 50:35:10:5 | 255 |
| 7 | 25:1 | 50:30:10:10 | 114 |
| 8 | 30:1 | 50:30:10:10 | 36 |

Example 4: Polyester-Mediated siRNA Delivery In Vitro

Figure 5:
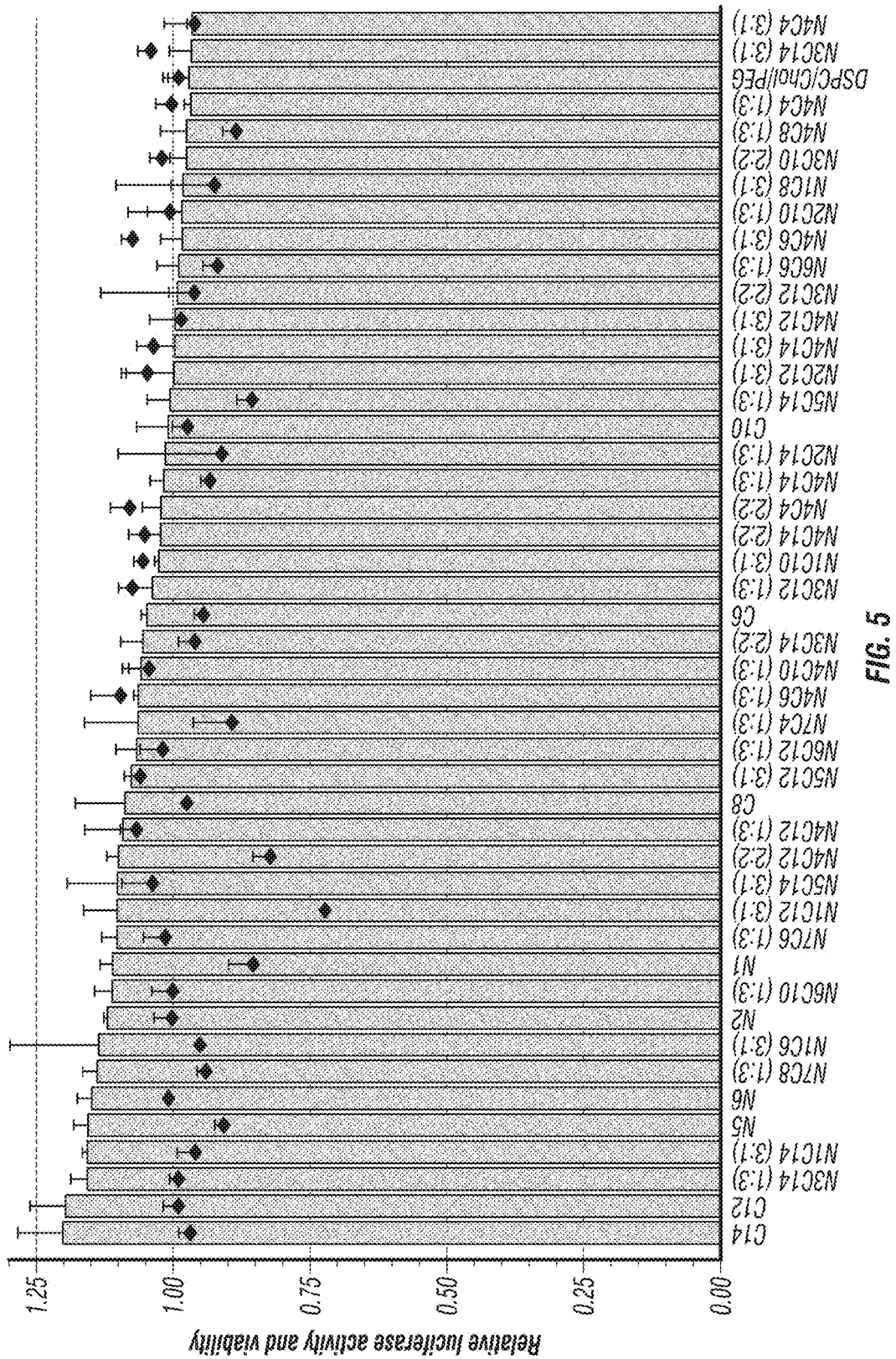
FIG. 5 shows the relative in vitro luciferase activity (bar graph) in luciferase expressing HeLa cells for each nanoparticle composition comprising a polymer with one of the specific monomer combination and a luciferase inhibiting siRNA. Additionally, the graph also shows cellular viability when treated with each nanoparticle (point markers).
Figure 5:
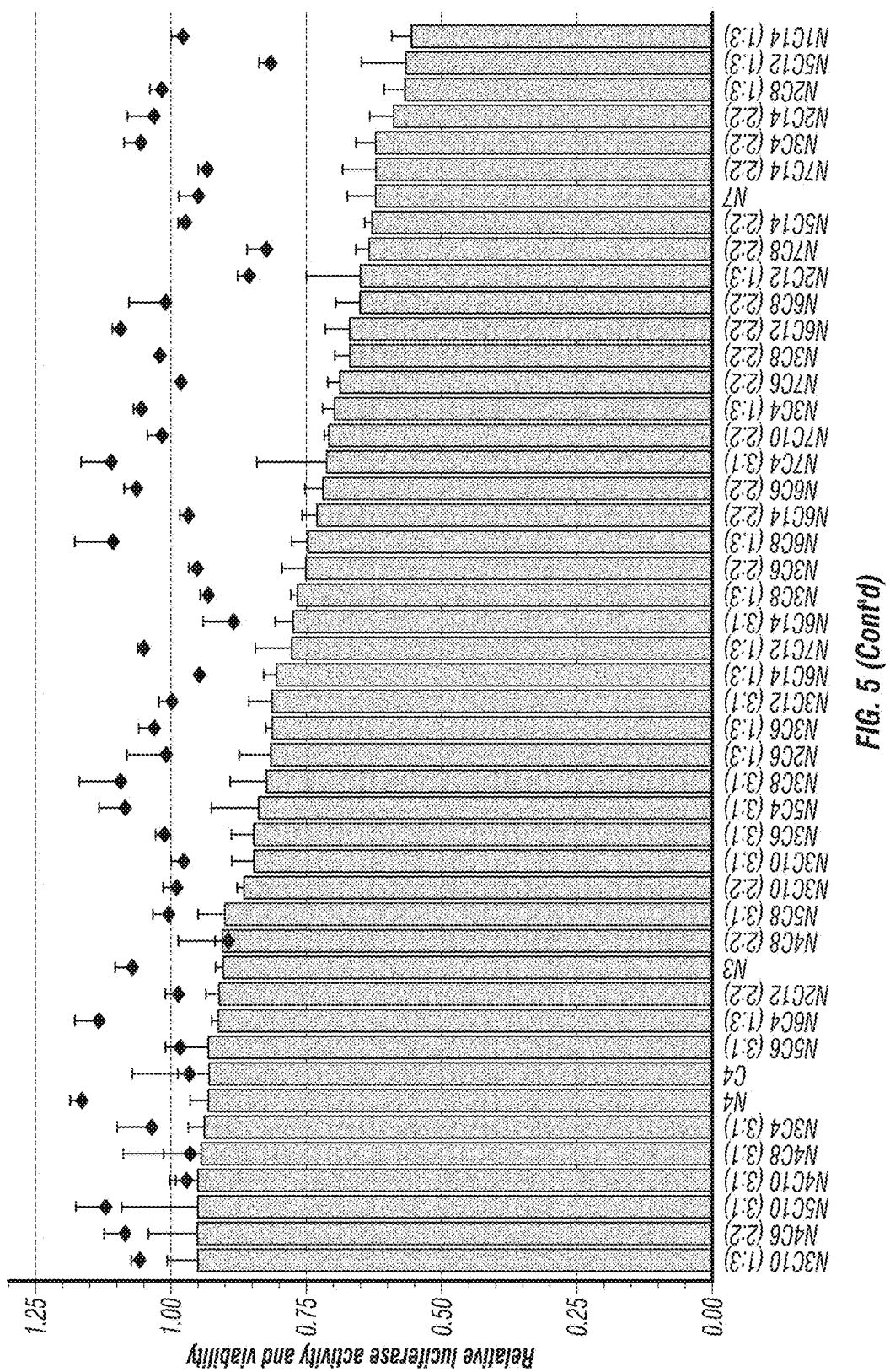
Figure 5:
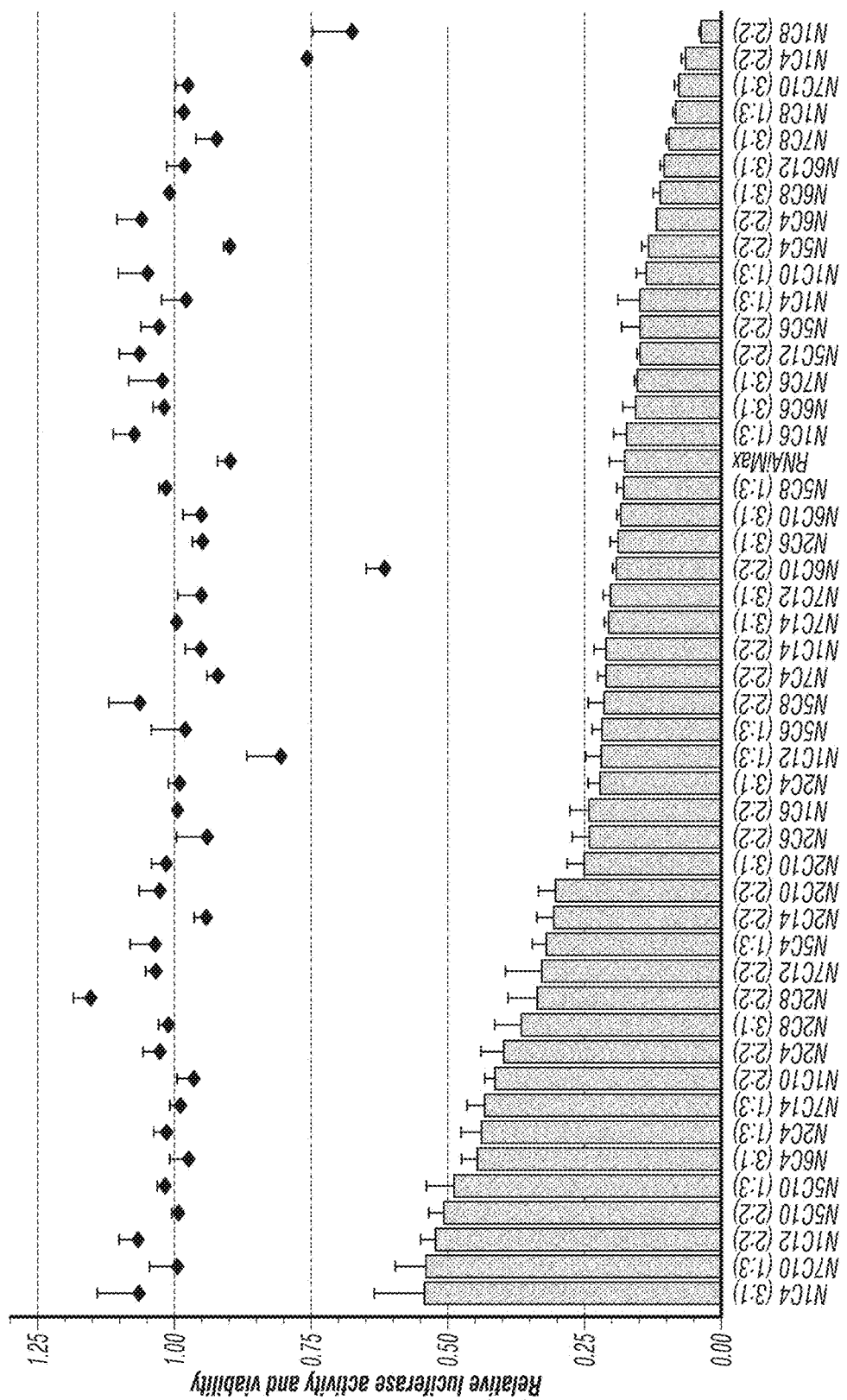

The lipocationic polyester library was screened in vitro in luciferase-expressing Hela cells with the aid of a Tecan fluid-handling robot. Polymers were diluted and mixed with helper compounds in ethanol at a mol ratio of polymer:DSPC:Cholesterol:PEG lipid=50:10:38:2. Nanoparticles were then formed by mixing with siLuc in pH 4.2 citrate buffer at a mol ratio of 100:1 (polymer:siRNA), diluted with PBS to raise the pH, and added to growing cells. The One Glo+Tox assay was used to evaluate cytotoxicity and delivery efficiency. RNAiMax (Invitrogen) and untreated cells were used as a positive and negative control, respectively, for cellular transfection. High-throughput screening of the polyester library indicates that the efficacy of the material could be modulated by incorporating different hydrophobic moieties at different monomer feeding ratios. As shown in FIG. 5, cytotoxicity assay indicates no evidence of adverse effects while 15% of the polymer library exhibit more than 80% knockdown efficiency. 6 polymers enabled>90% silencing at a dose of 30 nM. Delivery using only DSPC, cholesterol, and lipid PEG did not exhibit significant silencing at this dose. Interestingly, the delivery efficiency strongly correlated with chemical structure. A heat map (FIG. 6) organized by feeding ratio of the aminothiol monomer vs. alkylthiol monomer elucidated trends related to hydrophobicity and pKa. For polymers containing the dimethylamine group (M1), additional hydrophobic content is required to promote nanoparticle stability at pH 7.4 and enable delivery. When the hydrophobicity was increased (going to diethylamine (M2) and dipropylamine (M3)), less additional hydrophobic content from the alkyl comonomers was required to give a high delivery efficiency. Polymers made with dibutylamine (M4) showed little activity, likely due to steric hindrance that minimized electrostatic interactions, and possibly due to the further increase in hydrophobicity and pKa. For monomers containing cyclic amine side chains, a similar trend existed, analogous to M1 and M2, where more hydrophobic co-monomer was needed to give better delivery efficiency. These data suggest an optimized combination of amine group and hydrophobic co-monomer ratio could greatly enhance the delivery activity of the nanoparticle.

To investigate in vitro efficacy at low doses of siRNA, a dose response was conducted for top performing 12 polymers (FIG. 7). siRNA and polymer containing nanoparticles were incubated with cells at doses between 6.25 ng to 100 ng (siRNA). With the radio of polymer: siRNA held constant at 23:1 (wt:wt). Dose dependent silencing was observed for all the polymers tested. Five polymers were identified which facilitates greater than 60% silencing at an siRNA dosage of 25 ng per well while two polymers showing greater than 70% silencing at a dosage of 6.25 ng per well. In contrast, RNAiMax was not as effective in silencing luciferase expression head-to-head at the same doses.

Figure 9:
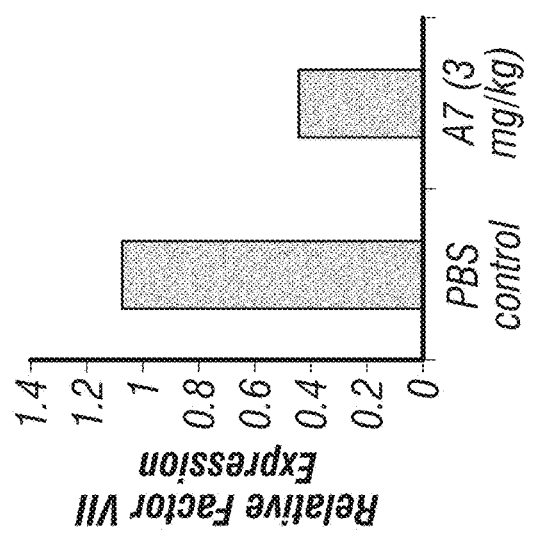
FIG. 9 shows the expression of Factor VII in liver hepatocytes when treated with a nanoparticle containing polymer A7 and a siRNA against Factor VII.

Microscopy. 10,000 HeLa cells/well were plated in chambered glass coverslips and allowed to grow for 1 day. Cells were then exposed to 100 ng NPs containing Cy5.5-labeled siRNA (Sigma-Aldrich) for 24 hours. The cells were washed with PBS, DAPI stained, and imaged using a confocal microscope (FIG. 9).

In vivo delivery of siRNA to Hepatocytes in Mice. To explore the performance of the nanoparticles in vivo, delivery to hepatocytes was examined in vivo. Results indicate that A7 enables 65% gene silencing in hepatocytes at a dose of 3 mg/kg (FIG. 9).

Figure 11:
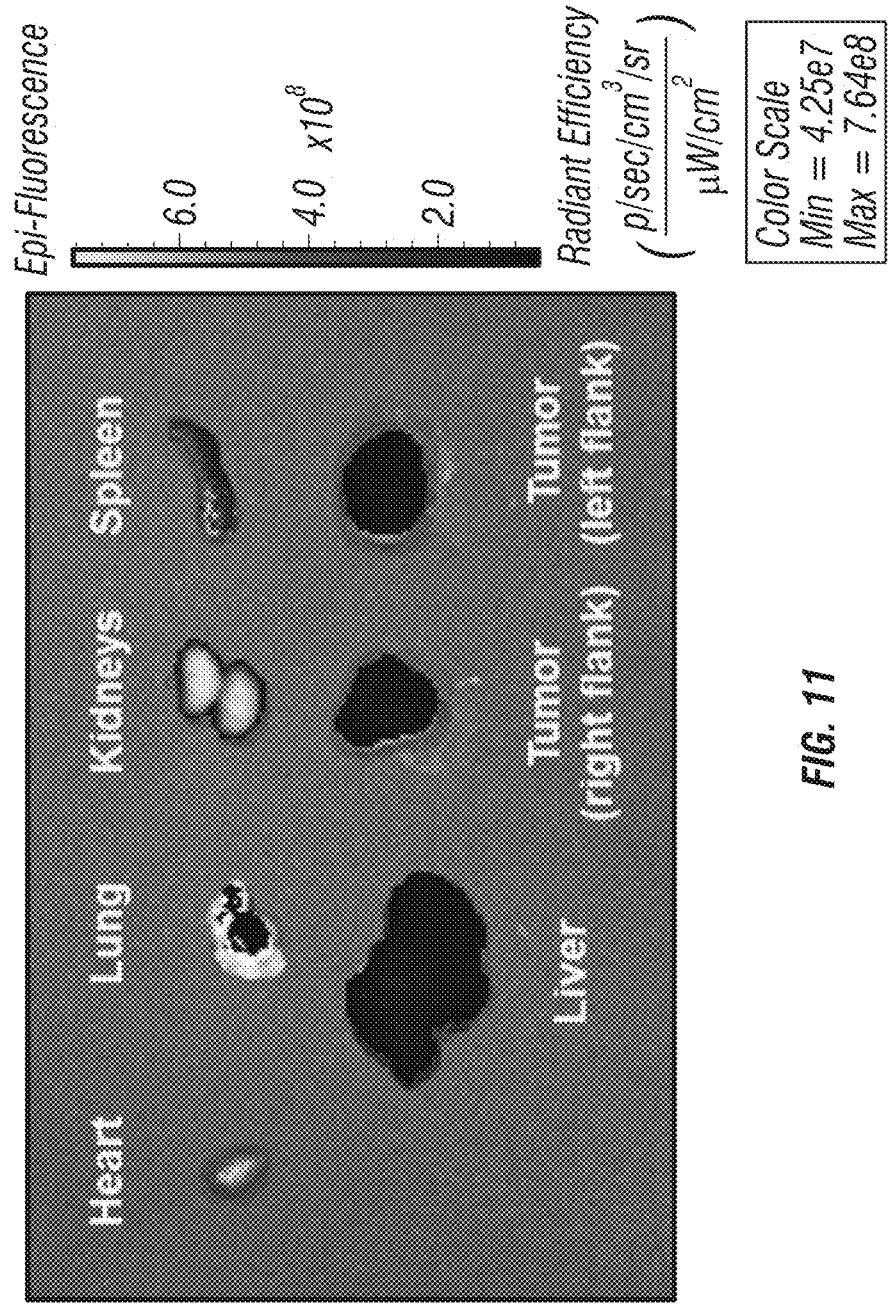
FIG. 11 shows the organ distribution of siRNA-containing polymeric NPs 2.5 hours after IV injection. The MDA-MB-231 tumor-bearing mice were injected intravenously at a siRNA dose of 2.5 mg/kg. A1 NPs (A1:cholesterol:DSPC:PEG-lipid=50:35:10:5; polymer:siRNA=20:1 (weight); aqueous:EtOH=3:1 (volume)).

Delivery of siRNA to tumors. The ability of lipocationic polyester NPs to localize and deliver siRNA to tumors was evaluated. A single dose of 2.5 mg/kg siRNA (1.25 mg/kg siLuc+1.25 mg/kg Cy5.5-siLuc) was delivered via intravenous (IV) tail vein injection to nude mice bearing MDA-MB-231-Luc xenograft tumors in both flanks. After 2.5 hours, remarkably high tumor accumulation of A1 NPs was measured (FIG. 10A). Fluorescence signals from the liver and kidneys were also visualized. Ex vivo imaging of harvested organs confirmed effective tumor uptake (FIG. 11). Moreover, luciferase activity in the tumors was greatly reduced after intratumoral (IT) injection of 2.5 mg/kg siLuc.

Figure 12A:
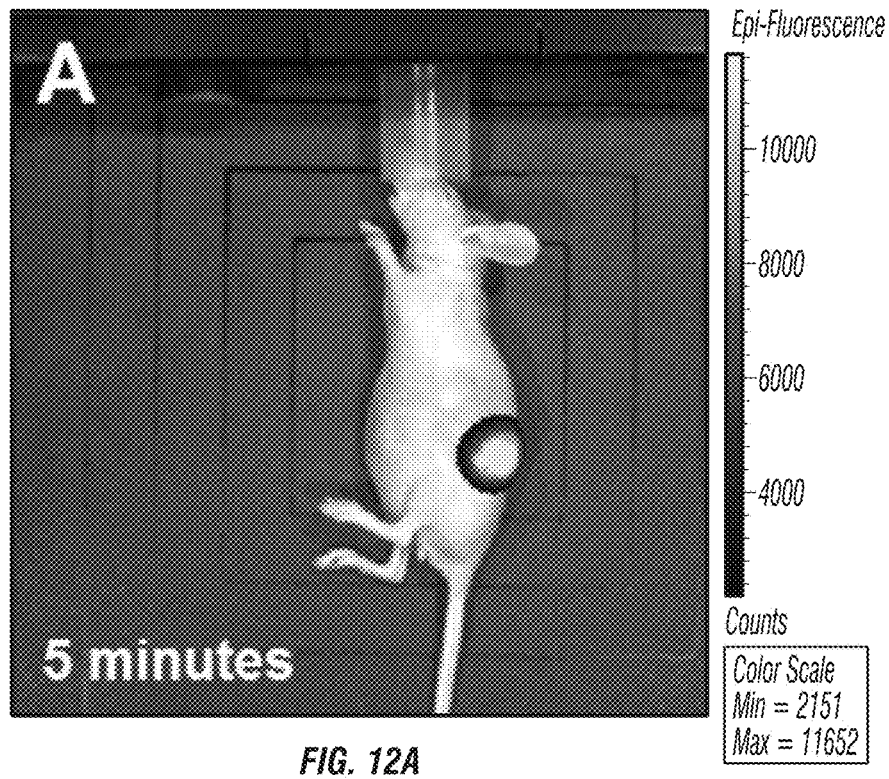
FIGS. 12A & 12B shows the tumor retention of siRNA-containing polymeric NPs 5 minutes (FIG. 12A) and 48 hours (FIG. 12B) after IT injection. The MDA-MB-231 tumor-bearing mice were injected intratumorally at a siRNA dose of 2.5 mg/kg.=50:35:10:5; polymer:siRNA=20:1 (weight); aqueous:EtOH=3:1 (volume).
Figure 12B:
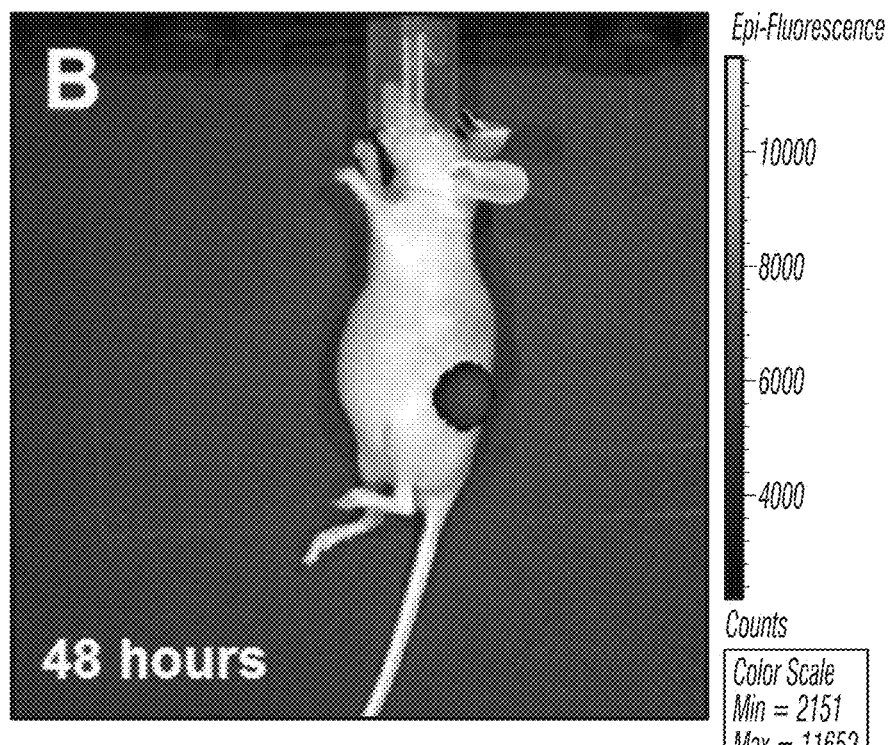

Luciferase was quantified by bioluminescence (FIG. 10B) and by tissue homogenization on total protein and tissue levels (FIG. 10C). Tumor reduction can be seen after 48 hours relative to tumor size after 5 minutes (FIG. 12).

Synthetic Scale-Up Conditions. A gram scale reaction was carried out for copolymer A6 to examine scalability:

A6: Synthesis of poly{4-((2-(dimethylamino)ethyl)thio) tetrahydro-2H-pyran-2-one}-r-poly{4-(hexylthio)tetrahydro-2H-pyran-2-one}. Monomer N1 (0.25 g, $1.2 \times 10^{-3}$ mol) and Monomer C6 (0.8 g, $3.6 \times 10^{-3}$ mol) were added to a flame-dried glass vial. 153 µL Methyl lithium (1.6 M in ether) was then added into the reaction vial to initiate the polymerization. The polymer was collected after 5 minutes and dialyzed against THF for 4 hours. The polymer was then concentrated and dried via vacuum pump for 24 hours. Yield=87.7%. The polymer was characterized via NMR and GPC (FIG. 16A). $^1$H NMR (500 MHz, CDCl$_3$): δ 4.27 (br, 4H), 3.12 (br, 2H), 2.61 (m, 6H), 2.52 (m, 4H), 2.24 (s, 6H), 1.98 (br, 2H), 1.84 (br, 2H), 1.55 (m, 2H), 1.28 (m, 6H), 0.88 (t, 3H).

Degradation of the Polymer Delivery Components. The degradation of the polymeric components was measured by measurement of polymer after exposure to 1M HCl (aq.) for 24 hours. Two representative copolymers are shown in FIG. 17 and Table 3.

TABLE 3

Degradation of Polymer after 24 hours in 1M HCl (aq.).

| Polymer | Initial $M_n$ (GPC) | Initial $M_w$ (GPC) | Initial PDI (GPC) | After 24 hrs $M_n$ (GPC) | After 24 hrs $M_w$ (GPC) | After 24 hrs PDI (GPC) |
|---------|---------------------|---------------------|-------------------|--------------------------|--------------------------|------------------------|
| C7      | 4000                | 5900                | 1.5               | 1700                     | 2800                     | 1.6                    |
| B9      | 4200                | 8600                | 2.1               | 2500                     | 5400                     | 2.2                    |

Synthetic Studies of Polymerization Initiator. A variety of different polymerization initiators and reaction conditions were studied for the preparation of the polymers described herein. Grignard reagents are also able to initiate polymerization. Various conditions were attempted, and are summarized below in Table 4.

TABLE 4

Study of Polymerization Initiators

| Mon | M:I ratio | Initiator       | Solvent | T    | Conv. (%) | $M_n$ (GPC) | PDI  |
|-----|-----------|-----------------|---------|------|-----------|-------------|------|
| N1  | 20:1      | $C_{12}H_{25}$MgBr | bulk    | r.t. | 68.3      | 4,680       | 1.66 |
| N2  | 10:1      | CH$_3$MgBr      | THF     | r.t. | 17.5      | 2,470       | 1.56 |
| N2  | 20:1      | CH$_3$MgBr      | bulk    | r.t. | 78.11     | 5,740       | 1.58 |
| N2  | 20:1      | CH$_3$MgBr      | toluene | r.t. | 26.5      | 3,580       | 1.64 |
| N2  | 20:1      | CH$_3$MgBr      | THF     | −78  | 28.82     | 3,720       | 1.86 |
| N2  | 20:1      | CH$_3$MgBr      | bulk    | r.t. | 59.0      | 7,200       | 1.39 |
| N2  | 20:1      | CH$_3$MgBr      | toluene | r.t. | 23.0      | 3,820       | 1.41 |
| N2  | 20:1      | CH$_3$MgBr      | THF     | r.t. | 25.3      | 5,550       | 1.54 |
| N3  | 20:1      | CH$_3$MgBr      | bulk    | r.t. | 59.0      | 4,730       | 1.46 |
| N4  | 20:1      | CH$_3$MgBr      | bulk    | r.t. | 73.6      | 6,480       | 1.33 |
| N4  | 20:1      | CH$_3$MgBr      | bulk    | r.t. | 82.3      | 4,280       | 1.27 |
| N5  | 20:1      | CH$_3$MgBr      | bulk    | r.t. | 66.7      | 3,110       | 1.44 |

TABLE 4-continued

Study of Polymerization Initiators

| Mon | M:I ratio | Initiator | Solvent | T | Conv. (%) | $M_n$ (GPC) | PDI |
|---|---|---|---|---|---|---|---|
| N6 | 20:1 | CH$_3$MgBr | bulk | r.t. | 60.9 | 3,180 | 1.43 |
| C8 | 20:1 | CH$_3$MgBr | bulk | r.t. | 84.19 | 5,700 | 1.37 |
| C8 | 20:1 | CH$_3$MgBr | toluene | r.t. | 16.32 | 2,620 | 1.43 |
| N1 + C8 | 10:10:1 | CH$_3$MgBr | bulk | r.t. | 84.02 | 7,100 | 1.51 |
| N1 + C8 | 15:5:1 | CH$_3$MgBr | bulk | r.t. | 74.45 | 4,600 | 1.46 |
| N1 + C8 | 5:15:1 | CH$_3$MgBr | bulk | r.t. | 81.1 | 8,590 | 1.40 |

Measurement of pKa of Polymers through pH titration. The selected copolymer (15 mg) was first dissolved in 100 µL THF and transferred into 20 mL deionized and purified water with 90 µL 1.0 M HCl (aq.). The pH titration was carried out by adding 5 µL of 1M NaOH solution (aq.) under stirring. The pH increase in the range of 2 to 12 was monitored as a function of total added volume of NaOH ($V_{NaOH}$). The pH values were measured using a Mettler Toledo pH meter with a microelectrode.

To further explore activity trends, pH titrations were performed to measure the pKa of a polymer series that displayed a clear siRNA delivery efficacy trend. Within the C8 (2:2) group, polymers A7 (2:2), B7 (2:2), C7 (2:2), and D7 (2:2) were analyzed. The pKa decreased from N1 to N4 and is shown in FIG. 18.

All of the compositions and methods disclosed and claimed herein can be made and executed without undue experimentation in light of the present disclosure. While the compositions and methods of this disclosure have been described in terms of certain embodiments, it will be apparent to those of skill in the art that variations may be applied to the compositions and methods and in the steps or in the sequence of steps of the methods described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references, to the extent that they provide exemplary procedural or other details supplementary to those set forth herein, are specifically incorporated herein by reference.

Jerome and Lecomte, Advanced Drug Delivery Reviews: 60, 1056, 2008.
Pounder and Dove, A. Polym Chem-Uk: 1, 260, 2010.
Tian et al., Prog Polym Sci: 37, 237, 2012.
Whitehead et al., D. NAT REV DRUG DISCOV: 8, 129, 2009.
Lee et al., Journal of Controlled Release: 152, 152, 2011.
Parmar et al., Bioconjugate Chem: 25, 896, 2014.
Tan et al., Small: 7, 841, 2011.
Albertsson and Varma, Adv Polym Sci: 157, 1, 2002.
Akincw et al., Nat Biotechnol: 26, 561, 2008.
Love et al., Natl Acad Sci USA: 107, 1864, 2010.
Siegwart et al., Natl Acad Sci USA: 108, 12996, 2011.
Jayaraman et al., Angew Chem Int Edit: 51, 8529, 2012.
Scholz and Wagner, E. Journal of Controlled Release: 161, 554, 2012.
Nelson et al., C. L. ACS Nano: 7, 8870, 2013.
Lynn and Langer, R. Journal of the American Chemical Society: 122, 10761, 2000.
Zugates et al., Journal of the American Chemical Society: 128, 12726, 2006.
Green et al., ACCOUNTS CHEM RES: 41, 749, 2008.
Davis et al., Nature (London, U. K.): 464, 1067, 2010.
Philipp et al., Bioconjugate Chem: 20, 2055, 2009.
Schroeder et al., Journal of Controlled Release: 160, 172, 2012.
Dahlman et al., Nat Nanotechnol 2014.
Kim et al., ACS Macro Letters: 1, 845, 2012.
Coelho et al., New Engl J Med: 369, 819, 2013.
Kanasty et al., Nat Mater: 12, 967, 2013.
Tempelaar et al., Macromolecules, 44, 2084, 2011.
Silvers et al., Polym Sci Pol Chem; 50, 3517, 2012.
Zimmermann et al., Nature: 441, 111, 2006.
Semple et al., Nat Biotechnol: 28, 172, 2010.
Hao et al., Current Organic Chemistry: 17, 930-942, 2013.

What is claimed is:

1. A method of silencing gene expression comprising contacting a composition comprising a nucleic acid and a polymer of the formula:

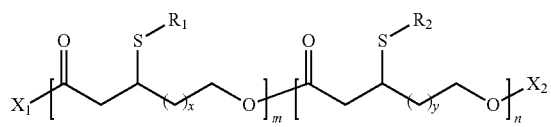

(I)

wherein:
  $X_1$ is alkyl$_{(C \leq 18)}$ or substituted alkyl$_{(C \leq 18)}$;
  $X_2$ is hydrogen, alkyl$_{(C \leq 18)}$, or substituted alkyl$_{(C \leq 18)}$;
  $R_1$ is -A-Z;
  wherein:
    A is an alkanediyl$_{(C \leq 18)}$ or substituted alkanediyl$_{(C \leq 18)}$;
    Z is —NR$_3$R$_4$;
    wherein:
      $R_3$ and $R_4$ are each independently selected from hydrogen, alkyl$_{(C \leq 18)}$, substituted alkyl$_{(C \leq 18)}$; or $R_3$ and $R_4$ are taken together and are alkanediyl$_{(C \leq 18)}$ or substituted alkanediyl$_{(C \leq 18)}$;
  $R_2$ is alkyl$_{(C \leq 24)}$, alkenyl$_{(C \leq 24)}$, substituted alkyl$_{(C \leq 24)}$, or substituted alkenyl$_{(C \leq 24)}$;
  x and y are each independently 0, 1, 2, 3, 4, or 5;
  m and n are each independently an integer between 0 and 250, provided that at least one of m and n is greater than 1; and
  the repeating units defined by m and n are randomly distributed throughout the polymer;
or a pharmaceutically acceptable salt thereof;
with a cell comprising said gene.

2. The method of claim 1, wherein the cell is contacted in vitro.

3. The method of claim 1, wherein the cell is contacted in vivo.

4. The method of claim 1, wherein the composition further comprises a steroid or steroid derivative.

5. The method of claim 1, wherein the composition further comprises a phospholipid.

6. The method of claim 1, wherein the composition further comprises a PEG lipid.

7. The method of claim 1, wherein the nucleic acid is a short (small) interfering RNA (siRNA), a microRNA (miRNA), a messenger RNA (mRNA), a cluster regularly interspaced short palindromic repeats (CRISPR), a plasmid DNA (pDNA), a double stranded DNA (dsDNA), a single stranded DNA (ssDNA), a single stranded RNA (ssRNA), a double stranded RNA (dsRNA), a locked nucleic acid (LNA), a peptide nucleic acid (PNA), a miRNA mimic, or a anti-miRNA.

8. The method of claim 7, wherein the nucleic acid is a siRNA.

9. A method of treating or preventing a disease or disorder comprising administering to a patient in need thereof a therapeutically effective amount of a composition comprising a polymer of the formula:

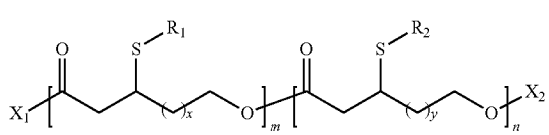

(I)

wherein:
  $X_1$ is alkyl$_{(C \leq 18)}$ or substituted alkyl$_{(C \leq 18)}$;
  $X_2$ is hydrogen, alkyl$_{(C \leq 18)}$, or substituted alkyl$_{(C \leq 18)}$;
  $R_1$ is -A-Z;
  wherein:
    A is an alkanediyl$_{(C \leq 18)}$ or substituted alkanediyl$_{(C \leq 18)}$;
    Z is —NR$_3$R$_4$;
    wherein:
      $R_3$ and $R_4$ are each independently selected from hydrogen, alkyl$_{(C \leq 18)}$, substituted alkyl$_{(C \leq 18)}$; or $R_3$ and $R_4$ are taken together and are alkanediyl$_{(C \leq 18)}$ or substituted alkanediyl$_{(C \leq 18)}$;
  $R_2$ is alkyl$_{(C \leq 24)}$, alkenyl$_{(C \leq 24)}$, substituted alkyl$_{(C \leq 24)}$, or substituted alkenyl$_{(C \leq 24)}$;
  x and y are each independently 0, 1, 2, 3, 4, or 5;
  m and n are each independently an integer between 0 and 250, provided that at least one of m and n is greater than 1; and
  the repeating units defined by m and n are randomly distributed throughout the polymer;
or a pharmaceutically acceptable salt thereof; and
a therapeutic nucleic acid for the disease or disorder.

10. The method of claim 9, wherein the disease or disorder is a disease or disorder associated with an overexpression of one or more genes.

11. The method of claim 9, wherein the composition is administered once.

12. The method of claim 9, wherein the composition is administered two or more times.

13. The method of claim 9, wherein the composition is administered intravenously.

14. The method of claim 9, wherein the nucleic acid is a short (small) interfering RNA (siRNA), a microRNA (miRNA), a messenger RNA (mRNA), a cluster regularly interspaced short palindromic repeats (CRISPR), a plasmid DNA (pDNA), a double stranded DNA (dsDNA), a single stranded DNA (ssDNA), a single stranded RNA (ssRNA), a double stranded RNA (dsRNA), a locked nucleic acid (LNA), a peptide nucleic acid (PNA), a miRNA mimic, or a anti-miRNA.

15. The method of claim 9, wherein the composition further comprises a steroid or steroid derivative.

16. The method of claim 9, wherein the composition further comprises a phospholipid.

17. The method of claim 9, wherein the composition further comprises a PEG lipid.

18. The method of claim 9, wherein the composition comprises a ratio of polymer to nucleic acid from about 5:1 to about 500:1.

19. A method of preparing a polymer of the formula:

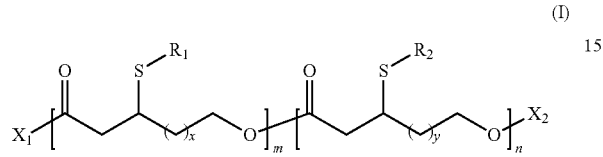

(I)

wherein:
X$_1$ and X$_2$ are independently selected from hydrogen, alkyl$_{(C\le12)}$, or substituted alkyl$_{(C\le12)}$;
R$_1$ is -A-Z;
wherein:
A is an alkanediyl$_{(C\le12)}$ or substituted alkanediyl$_{(C\le12)}$;
Z is —NR$_3$R$_4$;
wherein:
R$_3$ and R$_4$ are each independently selected from hydrogen, alkyl$_{(C\le12)}$, substituted alkyl$_{(C\le12)}$; or R$_3$ and R$_4$ are taken together and are alkanediyl$_{(C\le12)}$ or substituted alkanediyl$_{(C\le12)}$;
R$_2$ is alkyl$_{(C\le24)}$, alkenyl$_{(C\le24)}$, substituted alkyl$_{(C\le24)}$, or substituted alkenyl$_{(C\le24)}$;
x and y are each independently 0, 1, 2, 3, 4, or 5; and
m and n are each independently an integer between 0 and 250, provided that at least one of m and n is greater than 1; and
the repeating units defined by m and n are randomly distributed throughout the polymer;
comprising reacting a first monomer of the formula:

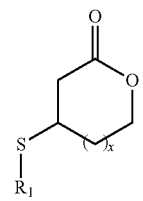

(II)

wherein: R$_1$ is -A-Z;
wherein:
A is an alkanediyl$_{(C\le12)}$ or substituted alkanediyl$_{(C\le12)}$;
Z is —NR$_3$R$_4$;
wherein:
R$_3$ and R$_4$ are each independently selected from hydrogen, alkyl$_{(C\le12)}$, substituted alkyl$_{(C\le12)}$; or R$_3$ and R$_4$ are taken together and are alkanediyl$_{(C\le12)}$ or substituted alkanediyl$_{(C\le12)}$;
x is 0, 1, 2, 3, 4, or 5;
with a second monomer of the formula:

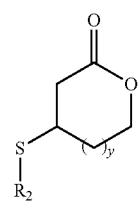

(III)

wherein:
R$_2$ is alkyl$_{(C\le24)}$, alkenyl$_{(C\le24)}$, substituted alkyl$_{(C\le24)}$, or substituted alkenyl$_{(C\le24)}$; and
y is 0, 1, 2, 3, 4, or 5;
in the presence of a base.

20. The method of claim 19, wherein the base is an alkyllithium reagent or a Grignard reagent.

* * * * *